US012735449B2

(12) United States Patent
Zhao et al.

(10) Patent No.: US 12,735,449 B2
(45) Date of Patent: Sep. 15, 2026

(54) ALPHA-CARBONYL ALKENYL ESTER PREPARATION METHOD THEREFOR AND APPLICATION THEREOF

(71) Applicant: JIANGXI NORMAL UNIVERSITY, Nanchang (CN)

(72) Inventors: Junfeng Zhao, Nanchang (CN); Zhengning Wang, Nanchang (CN); Xuewei Wang, Nanchang (CN)

(73) Assignee: JIANGXI NORMAL UNIVERSITY, Nanchang (CN)

( * ) Notice: Subject to any disclaimer, the term of this patent is extended or adjusted under 35 U.S.C. 154(b) by 1060 days.

(21) Appl. No.: 17/801,514

(22) PCT Filed: Aug. 19, 2020

(86) PCT No.: PCT/CN2020/110103
§ 371 (c)(1),
(2) Date: Aug. 22, 2022

(87) PCT Pub. No.: WO2021/169199
PCT Pub. Date: Sep. 2, 2021

(65) Prior Publication Data

US 2023/0242572 A1 Aug. 3, 2023

(30) Foreign Application Priority Data

Feb. 24, 2020 (CN) ........................ 202010112801.2

(51) Int. Cl.

| | |
|---|---|
| ***C07C 67/00*** | (2006.01) |
| ***C07C 67/08*** | (2006.01) |
| ***C07C 69/145*** | (2006.01) |
| ***C07C 69/606*** | (2006.01) |
| ***C07C 69/618*** | (2006.01) |
| ***C07C 69/753*** | (2006.01) |
| ***C07C 69/78*** | (2006.01) |
| ***C07C 227/18*** | (2006.01) |
| ***C07C 229/22*** | (2006.01) |
| ***C07C 231/12*** | (2006.01) |
| ***C07C 231/14*** | (2006.01) |
| ***C07C 233/05*** | (2006.01) |
| ***C07C 233/09*** | (2006.01) |
| ***C07C 233/11*** | (2006.01) |
| ***C07C 277/08*** | (2006.01) |
| ***C07C 279/24*** | (2006.01) |
| ***C07D 207/16*** | (2006.01) |
| ***C07D 209/20*** | (2006.01) |
| ***C07D 231/56*** | (2006.01) |
| ***C07D 233/64*** | (2006.01) |
| ***C07D 295/185*** | (2006.01) |
| ***C07D 307/68*** | (2006.01) |

(Continued)

(52) U.S. Cl.
CPC .............. *C07K 1/064* (2013.01); *C07C 67/08* (2013.01); *C07C 69/145* (2013.01); *C07C 69/606* (2013.01); *C07C 69/618* (2013.01); *C07C 69/753* (2013.01); *C07C 69/78* (2013.01); *C07C 227/18* (2013.01); *C07C 229/22* (2013.01); *C07C 231/12* (2013.01); *C07C 231/14* (2013.01); *C07C 233/05* (2013.01); *C07C 233/09* (2013.01); *C07C 233/11* (2013.01); *C07C 277/08* (2013.01); *C07C 279/24* (2013.01); *C07D 207/16* (2013.01); *C07D 209/20* (2013.01); *C07D 231/56* (2013.01); *C07D 233/64* (2013.01); *C07D 295/185* (2013.01); *C07D 307/68* (2013.01); *C07D 333/70* (2013.01); *C07K 1/22* (2013.01); *C07K 5/06043* (2013.01); *C07K 5/06052* (2013.01); *C07K 5/0606* (2013.01); *C07K 5/06069* (2013.01); *C07K 5/06078* (2013.01); *C07K 7/06* (2013.01)

(58) Field of Classification Search
CPC ....... C07K 1/064; C07C 67/08; C07C 69/145; C07C 69/606; C07C 69/618; C07C 69/753; C07C 69/78; C07C 227/18; C07C 229/22; C07C 231/12; C07C 231/14; C07C 233/05; C07C 233/09; C07C 233/11; C07C 277/08; C07C 279/24; C07D 207/16; C07D 209/20; C07D 231/56
See application file for complete search history.

(56) References Cited

PUBLICATIONS

Von Markus Neuenschwander, Hans-Peter Fahrni, and Ulrich Lienhard, "<< Push-Pull>>-Acetylene als Hilfsmittel zur Synthese von Peptiden," Helvetica Chimica Acta., vol. 61, No. 7, pp. 2437-2451 (1978). (Cited in ISR of PCT/CN2020/110103 dated Oct. 29, 2020).

(Continued)

*Primary Examiner* — Jeanette M Lieb
(74) *Attorney, Agent, or Firm* — Rankin, Hill & Clark LLP

(57) ABSTRACT

There is provided an α-carbonyl alkenyl ester and a preparation method therefor, and the α-carbonyl alkenyl ester is further used to react with a primary or secondary amine to prepare an amide. The two reactions are combined to develop an amide bond and peptide bond formation method that directly use carboxylic acids and amines as starting materials and allenones as a condensing reagent. The α-carbonyl alkenyl ester corresponding to an α-amino acid serves as a peptide synthesis building block and is used in solid phase peptide synthesis. The method is carried out under mild reaction conditions, simple to operate, and has a high yield. Compared with existing amide bond condensation reagents, the allenones have the advantages of being simple to prepare, having good stability, a low molecular weight, not racemizing when activating α-chiral carboxylic acids, and is a novel amide bond and peptide bond condensing reagent.

18 Claims, 4 Drawing Sheets

Specification includes a Sequence Listing.

(51) Int. Cl.

| | |
|---|---|
| ***C07D 333/70*** | (2006.01) |
| ***C07K 1/06*** | (2006.01) |
| ***C07K 1/22*** | (2006.01) |
| ***C07K 5/062*** | (2006.01) |
| ***C07K 5/065*** | (2006.01) |
| ***C07K 7/06*** | (2006.01) |

(56) References Cited

PUBLICATIONS

A. Stephen K. Hashmi, Jan W. Bats, Ji-Hyun Choi, and Lothar Schwarz, "Isomerizations on Silica Gel: Synthesis of Allenyl Ketones and the First Nazarov Cyclizations of Vinyl Allenyl Ketones," Tetrahedron Letters, vol. 39, No. 41, pp. 7491-7494 (1998). (Cited in ISR of PCT/CN2020/110103 dated Oct. 29, 2020).

John Larkin, Michael G. Murray, and Derek C. Nonhebel, "Enol Benzoates of B-Diketones," Journal of the Chemical Society, Perkin Transactions 1: Organic and Bio-Organic Chemistry, vol. 4, pp. 380-383 (1976). (Cited in ISR of PCT/CN2020/110103 dated Oct. 29, 2020).

Malcolm W. Moon, Larry T. Bell, and David M. Webster, "Acylation of Selected Pyrroles and Tertiary Amides," Journal of Organic Chemistry, vol. 39, No. 3, pp. 315-318 (1974). (Cited in ISR of PCT/CN2020/110103 dated Oct. 29, 2020).

R.B. Woodward and D.J. Woodman, "Stable Enol Esters from N-t-Butyl-5-methylisoxazolium Perchlorate," Journal of the American Chemical Society, vol. 90, No. 5, pp. 1371-1372 (1968). (Cited in ISR of PCT/CN2020/110103 dated Oct. 29, 2020).

International Search Report (English and Chinese) and Written Opinion of PCT/CN2020/110103 dated Oct. 29, 2020, 13 pages.

ALPHA-CARBONYL ALKENYL ESTER PREPARATION METHOD THEREFOR AND APPLICATION THEREOF

FIELD OF THE INVENTION

The invention belongs to the technical field of organic synthetic chemistry, relates to an activated ester, in particular to α-carbonyl alkenyl esters and their preparation methods and applications.

BACKGROUND OF THE INVENTION

Amide bonds exit widely in nature and are basic structural units of proteins. These ubiquitous structural units are found in polymers, drugs, fertilizers, materials and other fine chemicals. Because of the importance of amide bond structures, chemists have developed a series of methods to construct amide bonds. Traditional methods include condensation of acids and amines mediated by a condensation reagent, aminolysis of esters, or forming amide bonds by use of activated carboxylic acid derivatives (such as acyl chloride and anhydride). So far, activated ester method is also one of the methods to generate amide bonds. In this method, the carboxylic acid is first formed into an activated ester intermediate, and then the activated ester intermediate is subjected to an aminolysis reaction with an amine to generate the corresponding amide. To date, thousands of condensation reagents have been developed to activate carboxylic acids. They include carbodiimides, phosphoniums, uronium salts, alkynamides, etc. (Valeur, E. Chem. Soc. Rev. 2009, 38, 606-631). These condensation reagents have been used in various reaction environments, and some of them have been industrialized. But in this field, there are still some problems to be solved. Low coupling efficiency, racemization of reactants, and a large amount of waste after the reaction have hindered the development of amide bond formation reactions, especially peptide bond formation reactions. On the contrary, although there are still so many problems in the field of constructing amide bonds, the market demand for peptides is increasing day by day. Peptide and protein drugs are widely favored in academia and drug research and development, which make the research and development of polypeptide drugs become a hot field of new drug research and development. Although the raw material amino acids of polypeptides are very cheap, the price of polypeptide products are very high. This situation is mainly due to the cost of peptide synthesis, so the development of a kind of green, mild and efficient condensation reagents that are not easy to racemize is still an urgent need in the field of polypeptide synthesis.

As a very excellent 1,4-addition reaction receptor, allenones can undergo a 1,4-addition reaction with various nucleophiles to obtain the corresponding addition products. For example, amines, thiols, alcohols, etc. can conduct a Michael addition reaction with allenones to obtain enamines, enol ethers, and alkenyl thioethers (Hashmi, A. S. K. In Modern Allene Chemistry; Wiley: Verlag GmbH & Co. KGaA, Weinheim, 2004; pp 659-667). However, the 1,4-addition reaction between carboxylic acids and allenones has hardly been reported. The inventors of the present application found that carboxylic acids can react with allenones via a 1,4-addition reaction to obtain corresponding α-carbonyl alkenyl esters, which are relatively active, can undergo an efficient aminolysis reaction with primary or secondary amines to obtain corresponding amides. The aminolysis reaction in this step is fast, no additional catalysts and additives are required, and α-racemization of chiral carboxylic acids during activation and aminolysis can be well inhibited. By combining these two reactions, we have developed a new method of amide bond formation mediated by condensation reagent allenones using carboxylic acid and amine as raw materials. As a condensation reagent, allenones have the advantages of simple preparation, low molecular weight, high activation efficiency, and no racemization in activation of α-chiral carboxylic acids. At the same time, the reaction conditions are mild and the operation is simple. Its by-product benzoyl acetone also has important value in synthesis, which conforms to the direction of green chemistry in modern chemistry and has excellent atomic economy.

SUMMARY OF THE INVENTION

The present invention provides an α-carbonyl alkenyl ester and a synthesis method thereof, and the compound is also used to react with a primary or secondary amine to prepare an amide, thereby developing a method for the amide bond and peptide bond formation using a carboxylic acid and an amine as the starting materials and allenones as condensing reagents. The α-carbonyl alkenyl ester derived from α-amino acid is used as a polypeptide synthesis building block in the solid-phase synthesis of polypeptides. The method has mild reaction conditions, simple operation and high yield. Compared with the existing amide bond condensation reagents, allenones have the advantages of simple preparation, good stability, small molecular weight, no racemization when activating α-chiral carboxylic acid, etc., which are in line with the direction of green chemistry in modern chemistry, and have excellent atom economy and are a new type of amide bond and peptide bond condensation reagent.

In the present application, hydrocarbyl includes saturated or unsaturated straight chains or branched chains or cyclic hydrocarbon. The hydrocarbon optionally contains heteroatoms such as oxygen, sulfur or nitrogen. When the hydrocarbyl contains a cyclic ring, the cyclic ring can be a carbon ring or a heterocyclic ring, and the heterocyclic ring is, for example, a heterocyclic alkyl ring or a heteroaryl ring. In the present application, the hydrocarbyl is preferably alkyl, alkenyl, alkynyl, cycloalkyl, aryl or heteroaryl.

In the present application, for example, hydrocarbyl includes alkyl, cycloalkyl, heterocyclic alkyl, alkenyl, alkynyl, aryl, heteroaryl, alkyl aryl, alkyl heteroaryl, alkenylaryl, alkynyl aryl, alkenyl heteroaryl, alkynyl heteroaryl, arylalkyl, heteroarylalkyl, arylcycloalkyl, arylalkenyl, arylalkynyl, heteroarylalkenyl, or heteroarylalkynyl.

In the present application, "substituted by a substituent(s)" refers to being substituted by one or more (such as 1, 2, 3 or 4) substituents.

In the present application, the "hydrocarbyl" or "alkyl" in the protected amino hydrocarbyl (or alkyl) and the protected polypeptide chain hydrocarbon (or alkyl) may also be referred to as "hydrocarbylene" or "alkylene".

In the present application, for a protected amino group or a protected polypeptide chain, the protecting group is a commonly used protecting group in the art for protecting an amino group, an amino acid or a polypeptide chain. For example, the protecting group is selected from one or more of fluorenemethoxycarbonyl (Fmoc), benzyloxycarbonyl (Cbz), or tert-butoxycarbonyl (Boc), allyloxycarbonyl (Alloc), acetyl (Ac), methyl (Me), ethyl (Et), tert-butyl (tBu), trityl (Trt) or benzyl (Bn).

Preferably, the protecting group of the N-terminal amino group of the main chain is selected from one of fluorenemethoxycarbonyl (Fmoc), benzyloxycarbonyl (Cbz), tert-butoxycarbonyl (Boc), allyloxycarbonyl (Alloc), acetyl (Ac).

Preferably, the protecting group of the side chain amino functional group is selected from one or more of fluorenemethoxycarbonyl (Fmoc), benzyloxycarbonyl (Cbz), tert-butoxycarbonyl (Boc), allyloxycarbonyl (Alloc), acetyl (Ac), methyl (Me), ethyl (Et), tert-butyl (tBu), trityl (Trt) and benzyl (Bn).

For example, the protected amino C1-C20 hydrocarbyl can be derived from amino acids (ie, amino acid residues without carboxyl).

According to the first embodiment of the present invention, there is provided an α-carbonyl alkenyl ester having the general formula (I):

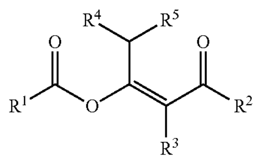

(I)

wherein $R^1$ is selected from one of C1-C24 hydrocarbyl (preferably C1-C18 hydrocarbyl), C1-C24 hydrocarbyl (preferably C1-C18 hydrocarbyl) substituted by a substituent(s), protected α-amino C1-C20 hydrocarbyl (preferably C2-C10 hydrocarbyl), protected β-amino C2-C20 hydrocarbyl (preferably C3-C10 hydrocarbyl), protected γ-amino C3-C20 hydrocarbyl (preferably C4-C10 hydrocarbyl), and protected polypeptide chain C1-C20 hydrocarbyl (preferably C2-C15 hydrocarbyl);

$R^2$ is selected from one of aryl, aryl substituted by a substituent(s), heteroaryl and heteroaryl substituted by a substituent(s);

$R^3$, $R^4$ and $R^5$ are the same or different, and are each independently selected from one of H, C1-C18 hydrocarbyl (preferably C1-C12 hydrocarbyl), C1-C18 hydrocarbyl (preferably C1-C12 hydrocarbyl) substituted by a substituent(s), C1-C16 acyl, cyano, halogen or C1-C16 hydrocarbyloxy-carbonyl (preferably C2-C12 hydrocarbyloxy-carbonyl).

Preferably, $R^3$, $R^4$ and $R^5$ are each independently selected from one of H, C1-C18 alkyl (preferably C1-C12 alkyl, more preferably C1-C6 alkyl), C1-C18 alkyl (preferably C1-C12 alkyl, more preferably C1-C6 alkyl) substituted by a substituent(s), C1-C16 acyl, cyano, halogen or C1-C16 alkoxy-carbonyl.

Preferably, for $R^1$, $R^3$, $R^4$ and $R^5$, the substituent(s) is C1-C8 hydrocarbyloxy, C1-C8 halohydrocarbyloxy, C1-C8 hydrocarbylthio, C1-C8 halo hydrocarbylthio, C1-C8 acyl, C1-C8 haloacyl, C1-C8 acyloxy, C1-C8 haloacyloxy, halogen, nitro and/or cyano. Here, the hydrocarbyl is preferably an alkyl or an alkenyl.

Preferably, for $R^2$, the substituent(s) is C1-C8 hydrocarbyl, C1-C8 halohydrocarbyl, C1-C8 hydrocarbyloxy, C1-C8 halohydrocarbyloxy, C1-C8 hydrocarbylthio, C1-C8 halo hydrocarbylthio, C1-C8 acyl, C1-C8 haloacyl, C1-C8 acyloxy, C1-C8 haloacyloxy, halogen, nitro and/or cyano. Here, the hydrocarbyl is preferably an alkyl or an alkenyl.

Preferably, $R^2$ is selected from one of C6-C24 aryl, C6-C24 aryl substituted by a substituent(s), C4-C24 heteroaryl, and C4-C24 heteroaryl substituted by a substituent(s).

Preferably, in formula (I), $R^1$ is selected from one of C1-C20 alkyl, C3-C8 cycloalkyl, C2-C22 alkenyl, C2-C22 alkynyl, C6-C20 aryl, C4-C20 heterocycloalkyl, C4-C20 heteroaryl, protected α-amino C1-C20 alkyl, protected β-amino C2-C20 alkyl, protected γ-amino C3-C20 alkyl, protected polypeptide chain C1-C20 alkyl.

More preferably, for $R^1$, the above-mentioned C1-C24 hydrocarbyl is selected from one of C1-C18 alkyl, C3-C8 cycloalkyl, C3-C8 heterocycloalky, C2-C18 alkenyl, C2-C18 alkynyl, C6-C18 aryl, C4-C18 heteroaryl, C7-C18 alkyl aryl, C5-C18 alkyl heteroaryl, C8-C18 alkenyl aryl, C8-C18 alkynyl aryl, C6-C18 alkenyl heteroaryl, C6-C18 alkynyl heteroaryl, C7-C18 arylalkyl, C5-C18 heteroarylalkyl, C9-C18 arylcycloalkyl, C8-C18 arylalkenyl, C8-C18 arylalkynyl, C6-C18 heteroaryl-alkenyl, or C6-C18 heteroarylalkynyl.

Preferably, $R^1$ is selected from one of C1-C18 alkyl, C3-C8 cycloalkyl, C2-C18 alkenyl, C2-C18 alkynyl, C6-C18 aryl, C3-C8 heterocyclyl, C4-C18 heteroaryl, protected α-amino C1-C20 hydrocarbyl (preferably C2-C10 hydrocarbyl), protected β-amino C2-C20 hydrocarbyl (preferably C3-C10 hydrocarbyl), protected γ-amino C3-C20 hydrocarbyl (preferably C4-C10 hydrocarbyl), and protected polypeptide chain C1-C20 hydrocarbyl (preferably C2-C15 hydrocarbyl).

In the present application, the hydrocarbyl mentioned here is preferably an alkyl or an alkenyl, or an alkylene or an alkenylene. Preferably, $R^1$ is selected from one of protected α-amino C1-C20 alkyl (such as C2-C10 alkyl), protected β-amino C1-C20 alkyl (such as C3-C10 alkyl), protected γ-amino C1-C20 alkyl (such as C4-C10 alkyl) and protected polypeptide chain C1-C20 alkyl(such as C2-C15 alkyl).

In the present application, "protected polypeptide chain C1-C20 hydrocarbyl" may also refer to: protected polypeptide chain acyl C1-C20 hydrocarbyl or protected polypeptide chain acyloxy C1-C20 hydrocarbyl.

Further preferably, $R^1$ is selected from one of C1-C5 alkyl, C1-C6 alkoxy-phenyl, phenyl-C1-C6 alkyl, phenyl-C2-C6 alkenyl, C2-C6 alkenyl, C2-C6 alkynyl, phenyl-C2-C6 alkenyl, phenyl-C2-C6 alkynyl, protected α-amino C2-C10 alkyl, protected β-amino C3-C10 alkyl, protected γ-amino C4-C10 alkyl, protected polypeptide chain C2-C15 alkyl.

Preferably, $R^1$ is selected from one of methyl, ethyl, propyl, isopropyl, butyl, tert-butyl, cyclopentyl, cyclohexyl, butenyl, adamantyl, vinyl, 1-propenyl, 2-propenyl, 1-butenyl, 2-butenyl, 3-butenyl, ethynyl, 1-propynyl, 2-propynyl, 1-butynyl, 2-butynyl, 3-butynyl, phenylethynyl, phenyl, naphthyl, anthracenyl, phenanthryl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, pyrrolyl, indolyl, indolylmethyl, indazolyl, furyl, benzofuranyl, thienyl, benzothienyl, styryl, phenylethynyl, benzyl, 11-hydroxyundecyl, pentadecyl, protected α-amino C2-C10 alkyl, protected β-amino C3-C10 alkyl, protected γ-amino C4-C10 alkyl, and protected polypeptide chain C2-C15 alkyl.

Preferably, $R^2$ is selected from one of phenyl, 4-fluorophenyl, 4-chlorophenyl, 4-bromophenyl, 4-methylphenyl, 4-methoxyphenyl, 2-methylphenyl, 2-methoxyphenyl, 3,5-dimethoxyphenyl, 3-nitrophenyl, 4-nitrophenyl, 2,4-dinitrophenyl, 3,5-dinitrophenyl, pentafluorophenyl, 4-trifluoromethylphenyl, 3,5-dichlorophenyl, 1-naphthyl, 2-naphthyl, furanyl and thienyl.

Preferably, $R^3$, $R^4$, $R^5$ are the same or different from each other, and are each independently selected from one of H, methyl, formyl, acetyl, propionyl, butyryl, cyano, methoxycarbonyl, ethoxycarbonyl, tert-butoxycarbonyl and benzyloxycarbonyl.

Preferably, $R^1$ is not unsubstituted or substituted phenyl or pyridyl.

Preferably, the compound having the general formula (I) is selected from one of the following compounds:

(E)-4-oxo-4-phenylbut-2-en-2-yl acetate:

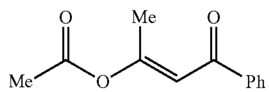 [SMILES: CC(=O)O/C(C)=C/C(=O)c1ccccc1]

(E)-4-oxo-4-phenylbut-2-en-2-yl (3r,5r,7r)-adamantane-1-carboxylate:

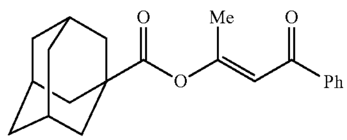 [SMILES: C/C(=C\C(=O)c1ccccc1)OC(=O)C12CC3CC(CC(C3)C1)C2]

(E)-4-oxo-4-phenylbut-2-en-2-yl 4-chlorobenzoate:

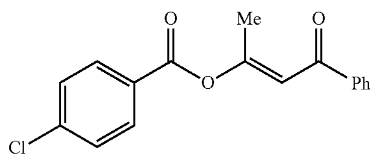 [SMILES: C/C(=C\C(=O)c1ccccc1)OC(=O)c1ccc(Cl)cc1]

(E)-4-oxo-4-phenylbut-2-en-2-yl furan-2-carboxylate:

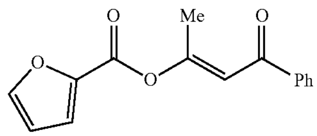 [SMILES: C/C(=C\C(=O)c1ccccc1)OC(=O)c1ccco1]

(E)-4-oxo-4-phenylbut-2-en-2-yl 1-methyl-1H-indazole-3-carboxylate:

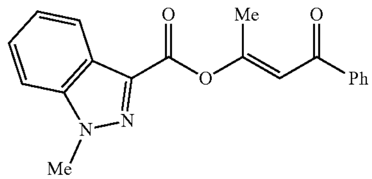 [SMILES: C/C(=C\C(=O)c1ccccc1)OC(=O)c1nn(C)c2ccccc12]

(E)-4-oxo-4-phenylbut-2-en-2-yl benzo[b]thiophene-2-carboxylate:

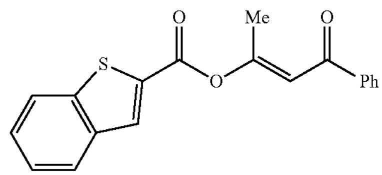 [SMILES: C/C(=C\C(=O)c1ccccc1)OC(=O)c1cc2ccccc2s1]

(E)-4-oxo-4-phenylbut-2-en-2-yl cinnamate:

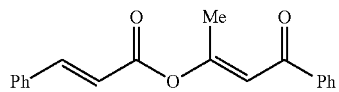 [SMILES: C/C(=C\C(=O)c1ccccc1)OC(=O)/C=C/c1ccccc1]

(E)-4-oxo-4-phenylbut-2-en-2-yl propiolate:

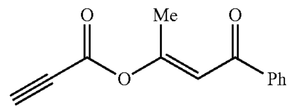 [SMILES: C#CC(=O)O/C(C)=C/C(=O)c1ccccc1]

(E)-4-oxo-4-phenylbut-2-en-2-yl 3-phenylpropiolate:

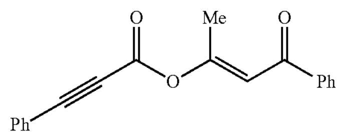 [SMILES: C/C(=C\C(=O)c1ccccc1)OC(=O)C#Cc1ccccc1]

(E)-4-oxo-4-phenylbut-2-en-2-yl 2-phenylacetate:

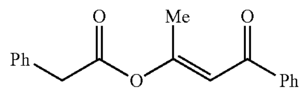 [SMILES: C/C(=C\C(=O)c1ccccc1)OC(=O)Cc1ccccc1]

(E)-4-oxo-4-phenylbut-2-en-2-yl 4-methoxybenzoate:

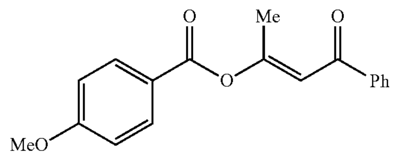 [SMILES: COc1ccc(C(=O)O/C(C)=C/C(=O)c2ccccc2)cc1]

(E)-4-(4-fluorophenyl)-4-oxobut-2-en-2-yl 4-methoxybenzoate:

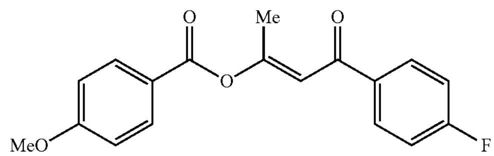 [SMILES: COc1ccc(C(=O)O/C(C)=C/C(=O)c2ccc(F)cc2)cc1]

(E)-4-(4-chlorophenyl)-4-oxobut-2-en-2-yl 4-methoxybenzoate:

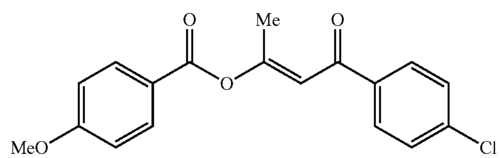 [SMILES: COc1ccc(C(=O)O/C(C)=C/C(=O)c2ccc(Cl)cc2)cc1]

(E)-4-(4-bromophenyl)-4-oxobut-2-en-2-yl 4-methoxybenzoate:

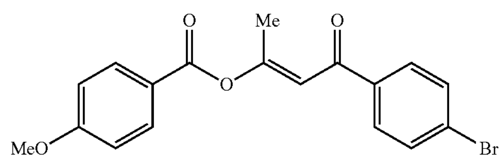

(E)-4-(4-nitrophenyl)-4-oxobut-2-en-2-yl 4-methoxybenzoate:

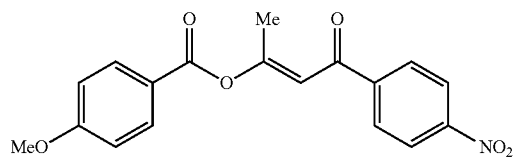 [SMILES: COc1ccc(C(=O)O/C(C)=C/C(=O)c2ccc([N+](=O)[O-])cc2)cc1]

(E)-4-(2-nitrophenyl)-4-oxobut-2-en-2-yl 4-methoxybenzoate:

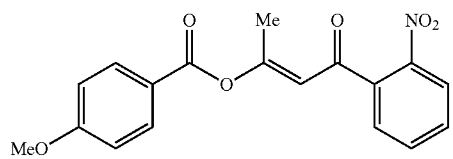 [SMILES: COc1ccc(C(=O)O/C(C)=C/C(=O)c2ccccc2[N+](=O)[O-])cc1]

(E)-4-(3,5-dimethoxyphenyl)-4-oxobut-2-en-2-yl 4-methoxybenzoate:

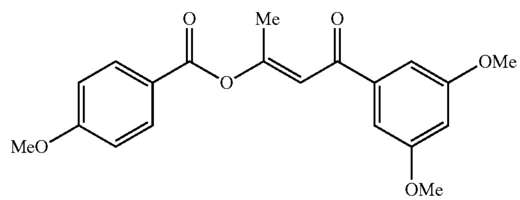 [SMILES: COc1ccc(C(=O)O/C(C)=C/C(=O)c2cc(OC)cc(OC)c2)cc1]

(E)-4-oxo-5-phenylpent-2-en-2-yl 4-methoxybenzoate:

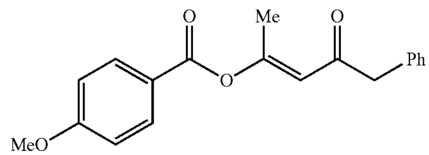 [SMILES: COc1ccc(C(=O)O/C(C)=C/C(=O)Cc2ccccc2)cc1]

(E)-4-(4-methoxyphenyl)-4-oxobut-2-en-2-yl 4-methoxybenzoate:

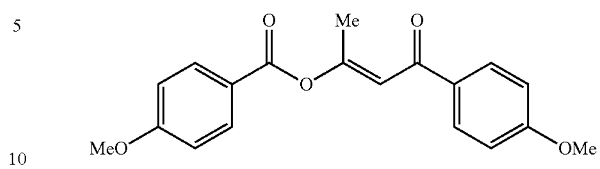

(E)-4-(furan-2-yl)-4-oxobut-2-en-2-yl 4-methoxybenzoate:

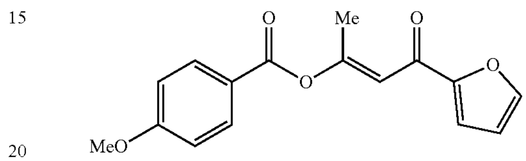

(E)-4-oxo-4-(thiophen-2-yl)but-2-en-2-yl 4-methoxybenzoate:

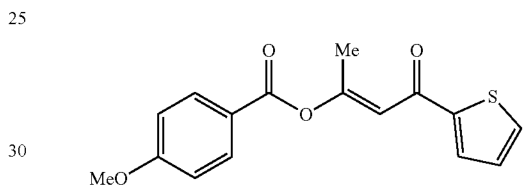

(E)-3-methyl-4-oxo-4-phenylbut-2-en-2-yl 4-methoxybenzoate:

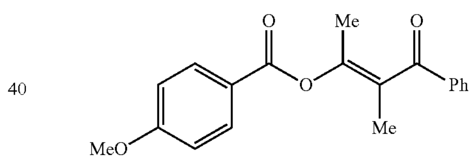

(E)-4-oxo-4-(perfluorophenyl)but-2-en-2-yl 4-methoxybenzoate:

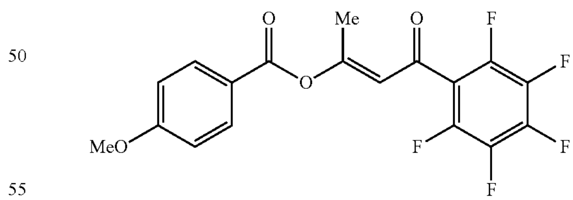

(E)-1-oxo-1-phenylpent-2-en-3-yl 4-methoxybenzoate:

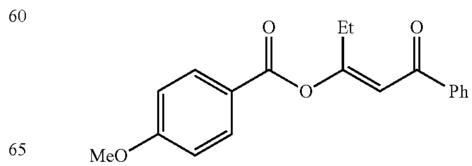

(E)-4-oxo-4-phenylbut-2-en-2-yl 3-((((9H-fluoren-9-yl) methoxy)carbonyl)amino)propanoate:

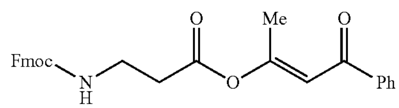

(E)-4-oxo-4-phenylbut-2-en-2-yl (((9H-fluoren-9-yl) methoxy)carbonyl)-L-alaninate:

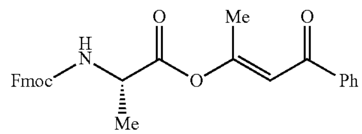

(E)-4-oxo-4-phenylbut-2-en-2-yl ((benzyloxy)carbonyl)-L-alaninate:

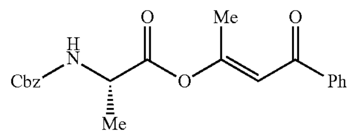 [SMILES: C/C(=C\C(=O)c1ccccc1)OC(=O)[C@H](C)NC(=O)OCc1ccccc1]

(E)-4-oxo-4-phenylbut-2-en-2-yl ((benzyloxy)carbonyl)-L-serinate:

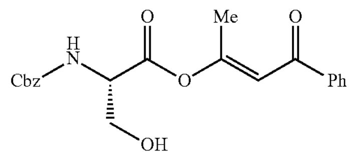 [SMILES: C/C(=C\C(=O)c1ccccc1)OC(=O)[C@H](CO)NC(=O)OCc1ccccc1]

(E)-4-oxo-4-phenylbut-2-en-2-yl (((9H-fluoren-9-yl) methoxy)carbonyl)-L-threoninate:

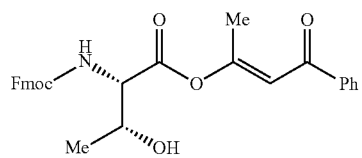

(E)-4-oxo-4-phenylbut-2-en-2-yl (((9H-fluoren-9-yl) methoxy)carbonyl)-L-tryptophanate:

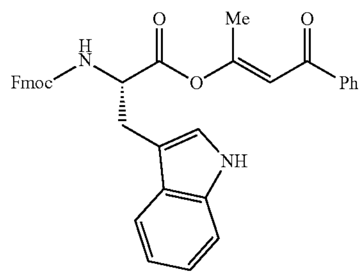

(E)-4-oxo-4-phenylbut-2-en-2-yl (tert-butoxycarbonyl)-L-threoninate:

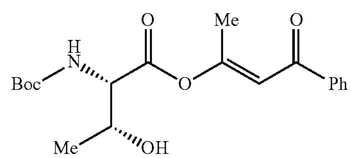 [SMILES: C/C(=C\C(=O)c1ccccc1)OC(=O)[C@@H](NC(=O)OC(C)(C)C)[C@@H](C)O]

(E)-4-oxo-4-phenylbut-2-en-2-yl (tert-butoxycarbonyl)-L-phenylalaninate:

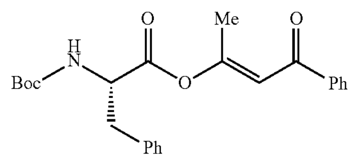 [SMILES: C/C(=C\C(=O)c1ccccc1)OC(=O)[C@H](Cc1ccccc1)NC(=O)OC(C)(C)C]

(E)-4-oxo-4-phenylbut-2-en-2-yl (((9H-fluoren-9-yl) methoxy)carbonyl)-L-leucinate:

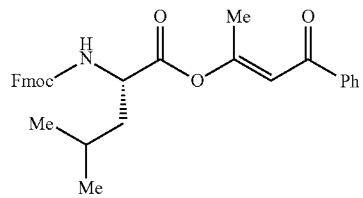

(E)-4-oxo-4-phenylbut-2-en-2-yl (((9H-fluoren-9-yl) methoxy)carbonyl)glycinate:

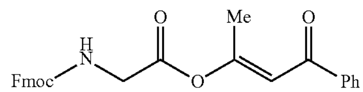

(E)-4-(tert-butyl)1-(4-oxo-4-phenylbut-2-en-2-yl) (((9H-fluoren-9-yl)methoxy)carbonyl)-L-aspartate:

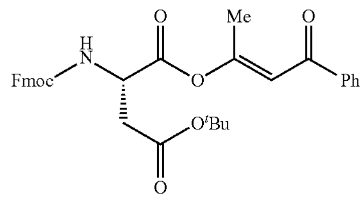

(E)-4-oxo-4-phenylbut-2-en-2-yl N-(((9H-fluoren-9-yl) methoxy)carbonyl)-S-trityl-L-cysteinate:

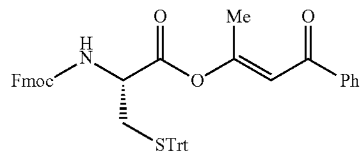

(E)-4-oxo-4-phenylbut-2-en-2-yl(S)-2-((((9H-fluoren-9-yl)methoxy)carbonyl)amino)-2-phenylacetate:

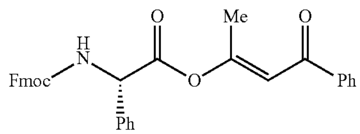

(E)-4-oxo-4-phenylbut-2-en-2-yl (((9H-fluoren-9-yl)methoxy)carbonyl)-L-methioninate:

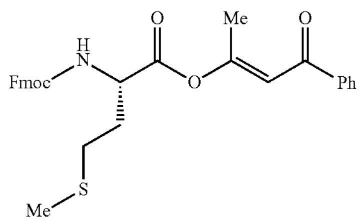

(E)-4-oxo-4-phenylbut-2-en-2-yl $N^2$-(((9H-fluoren-9-yl)methoxy)carbonyl)-$N^6$-(tert-butoxycarbonyl)-L-lysinate:

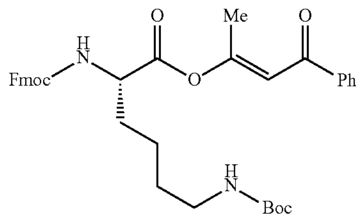

(E)-4-oxo-4-phenylbut-2-en-2-yl $N^2$-(((9H-fluoren-9-yl)methoxy)carbonyl)-$N^4$-trityl-L-asparaginate:

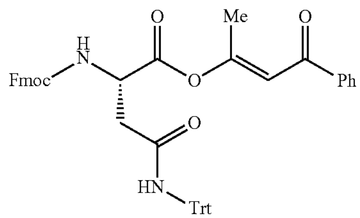

(E)-4-oxo-4-phenylbut-2-en-2-yl (((9H-fluoren-9-yl)methoxy)carbonyl)-L-isoleucinate:

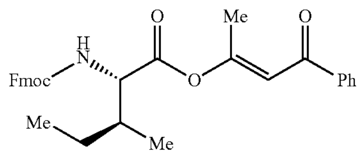

tert-butyl (S,E)-4-(2-((((9H-fluoren-9-yl)methoxy)carbonyl)amino)-3-oxo-3-((4-oxo-4-phenylbut-2-en-2-yl)oxy)propyl)-1H-imidazole-1-carboxylate:

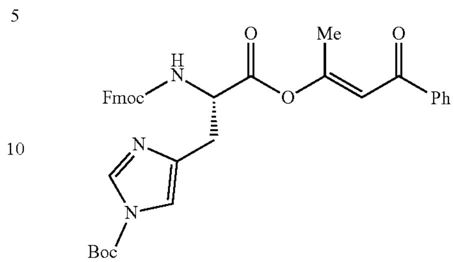

(E)-4-oxo-4-phenylbut-2-en-2-yl (S)-2-((((9H-fluoren-9-yl)methoxy)carbonyl)amino)-3-(4-(tert-butoxy)phenyl)propanoate:

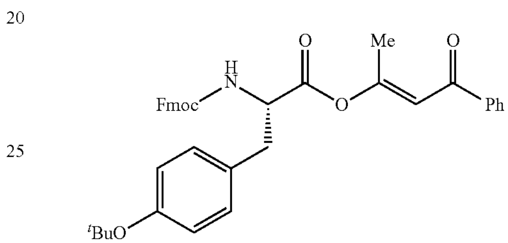

(E)-1-((9H-fluoren-9-yl)methyl) 2-(4-oxo-4-phenylbut-2-en-2-yl) (S)-pyrrolidine-1,2-dicarboxylate:

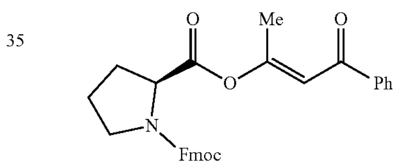

(E)-4-oxo-4-phenylbut-2-en-2-yl $N^2$-(((9H-fluoren-9-yl)methoxy)carbonyl)-$N^5$-trityl-L-glutaminate:

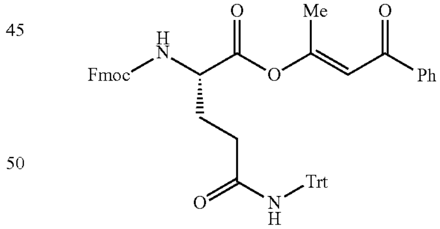

(E)-4-oxo-4-phenylbut-2-en-2-yl (Z)—$N^{\omega}$,$N^{\omega'}$-bis((benzyloxy)carbonyl)-$N^2$-(tert-butoxycarbonyl)-L-argininate:

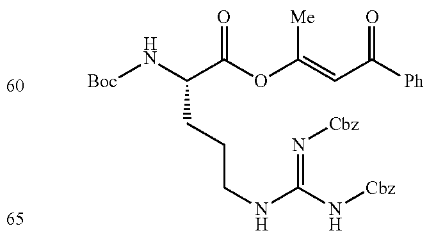

(E)-4-oxo-4-phenylbut-2-en-2-yl (((9H-fluoren-9-yl)methoxy)carbonyl)-L-alanyl-L-phenylalaninate:

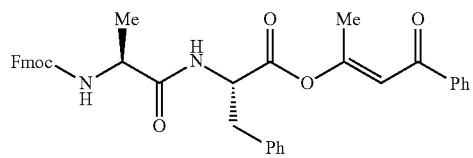

(E)-4-oxo-4-phenylbut-2-en-2-yl ((benzyloxy)carbonyl)-L-valyl-L-phenylalaninate:

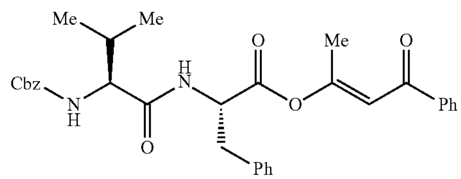 [SMILES: C/C(=C\C(=O)c1ccccc1)OC(=O)[C@H](Cc1ccccc1)NC(=O)[C@@H](NC(=O)OCc1ccccc1)C(C)C]

(E)-4-oxo-4-phenylbut-2-en-2-yl N-(((benzyloxy)carbonyl)-L-leucyl)-O-(tert-butyl)-L-serinate:

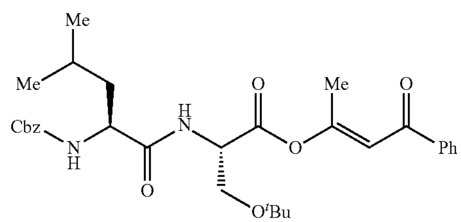 [SMILES: C/C(=C\C(=O)c1ccccc1)OC(=O)[C@H](COC(C)(C)C)NC(=O)[C@H](CC(C)C)NC(=O)OCc1ccccc1]

According to a second embodiment of the present invention, there is provided a method for preparing an α-carbonyl alkenyl ester having the general formula (I) or a method for preparing an α-carbonyl alkenyl ester having the general formula (I) according to the first embodiment:

(I)

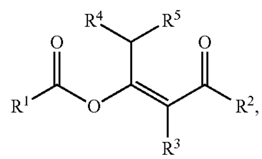

comprising:

A) reacting an allenone having the general formula (II) with a carboxylic acid having the general formula (III) in a solvent to afford the target compound:

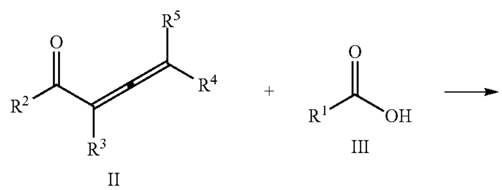

II III

-continued

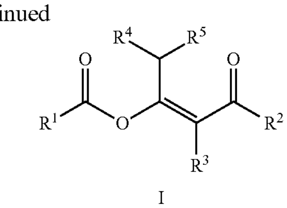

I wherein $R^1$ is selected from one of C1-C24 hydrocarbyl (preferably C1-C18 hydrocarbyl), C1-C24 hydrocarbyl (preferably C1-C18 hydrocarbyl) substituted by a substituent(s), protected α-amino C1-C20 hydrocarbyl (preferably C2-C10 hydrocarbyl), protected β-amino C2-C20 hydrocarbyl (preferably C3-C10 hydrocarbyl), protected γ-amino C3-C20 hydrocarbyl (preferably C4-C10 hydrocarbyl), and protected polypeptide chain C1-C20 hydrocarbyl (preferably C2-C15 hydrocarbyl);

$R^2$ is selected from one of C1-C24 hydrocarbyl (preferably C1-C18 hydrocarbyl), and C1-C24 hydrocarbyl (preferably C1-C18 hydrocarbyl) substituted with a substituent(s); and $R^3$, $R^4$ and $R^5$ are the same or different, and are each independently selected from one of H, C1-C18 hydrocarbyl (preferably C1-C12 hydrocarbyl), C1-C18 hydrocarbyl (preferably C1-C12 hydrocarbyl) substituted by a substituent(s), C1-C16 acyl, cyano, halogen or C1-C16 hydrocarbyloxy-carbonyl (preferably C2-C12 hydrocarbyloxy-carbonyl).

Preferably, $R^3$, $R^4$ and $R^5$ are each independently selected from one of H, C1-C18 alkyl (preferably C1-C12 alkyl, more preferably C1-C6 alkyl), C1-C18 alkyl (preferably C1-C12 alkyl, more preferably C1-C6 alkyl) substituted by a substituent(s), C1-C16 acyl, cyano, halogen or C1-C16 alkoxy-carbonyl. Here, the hydrocarbyl is preferably alkyl or alkenyl.

Preferably, for $R^1$, $R^3$, $R^4$ and $R^5$, the substituent(s) is selected from C1-C8 hydrocarbyloxy, C1-C8 halohydrocarbyloxy, C1-C8 hydrocarbylthio, C1-C8 halo hydrocarbylthio, C1-C8 acyl, C1-C8 haloacyl, C1-C8 acyloxy, C1-C8 haloacyloxy, halogen, nitro and/or cyano. Here, the hydrocarbyl is preferably an alkyl or an alkenyl.

Preferably, for $R^2$, the substituent(s) is selected from C1-C8 hydrocarbyl, C1-C8 halohydrocarbyl, C1-C8 hydrocarbyloxy, C1-C8 halohydrocarbyloxy, C1-C8 hydrocarbylthio, C1-C8 halo hydrocarbylthio, C1-C8 acyl, C1-C8 haloacyl, C1-C8 acyloxy, C1-C8 haloacyloxy, halogen, nitro and/or cyano. Here, the hydrocarbyl is preferably an alkyl or an alkenyl.

Preferably, $R^1$ is selected from one of C1-C20 alkyl, C3-C8 cycloalkyl, C2-C22 alkenyl, C2-C22 alkynyl, C6-C20 aryl, C4-C20 heterocycloalkyl, C4-C20 heteroaryl, protected α-amino C1-C20 alkyl, protected β-amino C2-C20 alkyl, protected γ-amino C3-C20 alkyl, protected polypeptide chain C1-C20 alkyl.

More preferably, for $R^1$ or $R^2$, the above-mentioned C1-C24 hydrocarbyl is selected from C1-C18 alkyl, C3-C8 cycloalkyl, C3-C8 heterocycloalkyl, C2-C18 alkenyl, C2-C18 alkynyl, C6-C18 aryl, C4-C18 heteroaryl, C7-C18 alkyl aryl, C5-C18 alkyl heteroaryl, C8-C18 alkenyl aryl, C8-C18 alkynyl aryl, C6-C18 alkenylheteroaryl, C6-C18 alkynylheteroaryl, C7-C18 aryl alkyl, C5-C18 heteroarylalkyl, C9-C18 aryl cycloalkyl, C8-C18 arylalkenyl, C8-C18 aryl alkynyl, C6-C18 heteroaryl-alkenyl, or C6-C18 heteroarylalkynyl.

Preferably, $R^1$ is selected from one of C1-C18 alkyl, C3-C8 cycloalkyl, C2-C18 alkenyl, C2-C18 alkynyl, C6-C18 aryl, C3-C8 heterocyclyl, C4-C18 heteroaryl, protected α-amino C1-C20 hydrocarbyl (preferably C2-C10 hydrocarbyl), protected β-amino C2-C20 hydrocarbyl (preferably C3-C10 hydrocarbyl), protected γ-amino C3-C20 hydrocarbyl (preferably C4-C10 hydrocarbyl), and protected polypeptide chain C1-C20 hydrocarbyl (preferably C2-C15 hydrocarbyl).

In the present application, the hydrocarbyl mentioned here is preferably an alkyl or an alkenyl, or an alkylene or an alkenylene. Preferably, $R^1$ is selected from one of protected α-amino C1-C20 alkyl (such as C2-C10 alkyl), protected β-amino C2-C20 alkyl (such as C3-C10 alkyl), protected γ-amino C3-C20 alkyl (such as C4-C10 alkyl groups) and protected polypeptide chain C1-C20 alkyl (such as C2-C15 alkyl).

Further preferably, $R^1$ is selected from one of C1-C5 alkyl, C1-C6 alkoxy-phenyl, phenyl-C1-C6 alkyl, phenyl-C2-C6 alkenyl, C2-C6 alkenyl, C2-C6 alkynyl, phenyl-C2-C6 alkenyl, phenyl-C2-C6 alkynyl, protected α-amino C2-C10 alkyl, protected β-amino C3-C10 alkyl, protected γ-amino C4-C10 alkyl, protected polypeptide chain C2-C15 alkyl.

Preferably: $R^2$ is selected from one of C6-C24 aryl, C6-C24 aryl substituted by a substituent(s), C4-C24 heteroaryl, C4-C24 heteroaryl substituted by a substituent(s); or, $R^2$ is selected from C1-C5 alkyl, C1-C6 alkoxy-phenyl, phenyl-C1-C6 alkyl, phenyl-C2-C6 alkenyl, C2-C6 alkenyl, C2-C6 alkynyl, phenyl-C2-C6 alkenyl, or phenyl-C2-C6 alkynyl.

Preferably, $R^1$ is selected from one of methyl, ethyl, propyl, isopropyl, butyl, tert-butyl, cyclopentyl, cyclohexyl, butenyl, adamantyl, vinyl, 1-propenyl, 2-propenyl, 1-butenyl, 2-butenyl, 3-butenyl, ethynyl, 1-propynyl, 2-propynyl, 1-butynyl, 2-butynyl, 3-butynyl, phenylethynyl, phenyl, naphthyl, anthracenyl, phenanthryl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, pyrrolyl, indolyl, indolylmethyl, indazolyl, furyl, benzofuranyl, thienyl, benzothienyl, styryl, phenylethynyl, benzyl, 11-hydroxyundecyl, pentadecyl, protected α-amino C2-C10 alkyl, protected β-amino C3-C10 alkyl, protected γ-amino C4-C10 alkyl, and protected polypeptide chain C2-C15 alkyl.

Preferably, $R^2$ is selected from one of methyl, ethyl, propyl, isopropyl, butyl, tert-butyl, cyclopentyl, cyclohexyl, phenyl, 4-fluorophenyl, 4-chlorophenyl, 4-bromophenyl, 4-methylphenyl, 4-methoxyphenyl, 2-methylphenyl, 2-methoxyphenyl, 3,5-dimethoxyphenyl, 3-nitrophenyl, 4-nitrophenyl, 2,4-dinitrophenyl, 3,5-dinitrophenyl, pentafluorophenyl, 4-trifluoromethylphenyl, 3,5-dichlorophenyl, 1-naphthyl, 2-naphthyl, furanyl and thienyl.

Preferably, $R^3$, $R^4$, $R^5$ are the same or different from each other, and are each independently selected from one of H, methyl, formyl, acetyl, propionyl, butyryl, cyano, methoxycarbonyl, ethoxycarbonyl, tert-butoxycarbonyl and benzyloxycarbonyl.

Preferably, $R^1$ is not unsubstituted or substituted phenyl or pyridyl.

Preferably, in step A), the molar ratio of the allenone having the general formula (II) to the carboxylic acid having the general formula (III) is 1:1-2, preferably 1:1-1.5, more preferably 1:1-1.2.

Preferably, the solvent is an organic solvent, preferably an aprotic organic solvent. Preferably, the aprotic organic solvent is selected from one or more of dichloromethane, chloroform, 1,2-dichloroethane, acetonitrile, tetrahydrofuran, water, diethyl ether and toluene, preferably one or more of dichloromethane, chloroform and 1,2-dichloroethane. More preferably, the solvent is 1,2-dichloroethane.

Preferably, the molar ratio of the amount of the aprotic organic solvent to the amount of the allenone represented by formula II is 70-170:1, preferably 90-150:1, more preferably 110-130:1.

Preferably, step A) is specifically as follows: adding the allenone of the general formula (II) and the solvent together into a reactor in proportion, and then adding the carboxylic acid of the general formula (III), reacting at 0-100° C. (preferably 20-60° C., more preferably 30-50° C.) with stirring for 0.5-320 h (preferably 1-240 h, more preferably 5-180 h), using TLC (Thin Layer Chromatography) to monitor the end of the reaction, and obtaining the α-carbonyl alkenyl ester having the general formula (I) by column chromatography after the reaction.

According to the third embodiment of the present invention, there is provided the use of the α-carbonyl alkenyl ester having the general formula (I) described in the first embodiment or prepared by the method described in the second embodiment as amidation reagents, in particular, provides a method for preparing amides having the general formula (V) using them as intermediates, comprising the following steps:

B) reacting the α-carbonyl alkenyl ester of the general formula (I) with the compound (ammonia or organic amine) of the general formula (IV) in a solvent, and optionally separating the reaction product, to obtain the target compound (V):

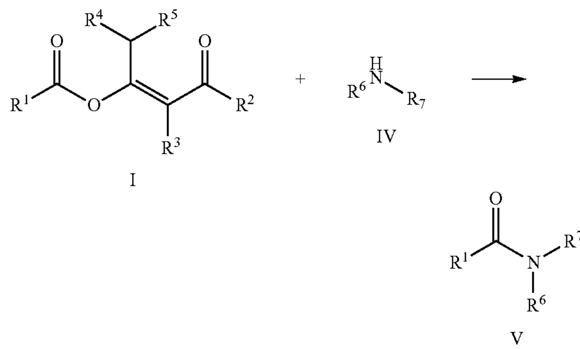

I IV V wherein the respective definitions of $R^1$, $R^2$, $R^3$, $R^4$ or $R^5$ (also including their preferred definitions) are the same as the definitions of the corresponding groups $R^1$, $R^2$, $R^3$, $R^4$ or $R^5$ in the first embodiment described above (also including their preferred definitions), or the same as the definitions for the corresponding groups $R^1$, $R^2$, $R^3$, $R^4$ or $R^5$ in the second embodiment above (also including their preferred definitions).

$R^6$ and $R^7$ are each independently selected from one of H, amino, C1-C24 hydrocarbyl (e.g. C1-C18 hydrocarbyl, such as C1-C12 hydrocarbyl), C1-C24 hydrocarbyl substituted by a substituent(s) (e.g. C1-C18 hydrocarbyl, such as C2-C12 hydrocarbyl), or amino oligomers or amino polymers with primary and/or secondary amine group(s) (e.g. degree of polymerization between 2-1000, preferably between 3-500, preferably between 4-200, preferably between 5-100, more preferably between 6-20); or, $R^6$ and $R^7$ together with the N atom to which they are attached form a C3-C24 cyclic ring (e.g. C3-C18 cyclic ring such as substituted or unsubstituted piperidine or piperazine rings). Preferably, for $R^6$ and $R^7$, the substituents are selected from C1-C8 hydrocarbyl, C1-C8 halohydrocarbyl, C1-C8 hydrocarbyloxy, C1-C8 halohydrocarbyloxy, C1-C8 hydrocarbylthio, C1-C8 halohydrocarbylthio, C1-C8 acyl, C1-C8 haloacyl, C1-C8 acyloxy, C1-C8 haloacyloxy, amino, hydroxyl, carboxyl, mercapto, halogen, nitro and/or cyano. The hydrocarbyl mentioned here is preferably an alkyl, a cycloalkyl, an alkenyl, an alkynyl, a heterocyclic, an aryl, a heterocyclic aryl, for example, the hydrocarbyloxy is preferably an alkoxy or a cycloalkyloxy. Preferably, the amino oligomer comprises a polypeptide chain. The amino polymers include proteins or polyamines.

Generally, $R^6$ and $R^7$ are not both amino.

Preferably, $R^6$ and $R^7$ are each independently selected from one of H, amino, methyl, ethyl, propyl, isopropyl, butyl, tert-butyl, cyclopentyl, cyclohexyl, cycloheptyl, cyclooctyl, cyclobutanediyl, cyclopentanediyl, cyclohexanediyl, cycloheptanediyl, cyclooctanediyl, hydroxyethylphenyl, phenyl, ethylphenyl, phenethyl, naphthyl, 3-indoleethyl, α-acyl C1-C20 alkyl, β-acyl C2-C20 alkyl, γ-acyl C3-C20 alkyl, polypeptide chain C1-C20 alkyl or polypeptide chain C1-C20 alkenyl.

In the present application, "optionally" means performed or not performed.

The compound of the general formula (IV) mentioned above is a compound with at least one N—H bond. Generally, the compounds having general formula (IV) are: ammonia; hydrazine; C1-C50 organic amines containing primary and/or secondary amines (i.e., organic amine compounds with at least one N—H bond, preferably C1-C32 organic amines or amino acids, more preferably C1-C24 organic amines, more preferably C1-C12 organic amines); or, amino oligomers or amino polymers (including polypeptides or proteins or polyamines) with primary and/or secondary amine group(s) (for example, the degree of polymerization is between 2-1000, preferably between 3-500, preferably between 4-200, preferably between 5-100, more preferably between 6-20). In the present application, the α-carbonyl alkenyl ester having the general formula (I) is used as the acylating reagent having the general formula (IV).

Preferably, the organic amines (OA), that is, organic amine compounds having at least one N—H bond, are those selected from the following:

amino acids;

C1-C24 hydrocarbylamines (primary amines) such as methylamine, ethylamine, propylamine, butylamine, pentylamine, hexylamine, heptylamine, octylamine, nonylamine, decylamine, dodecylamine, behenylamines, unsubstituted or substituted (such as halogen-substituted) anilines, methyl cyclohexyl amine, or N-methylbenzylamines, etc.;

di(C1-C16 hydrocarbyl) amines (secondary amines, i.e. monoamines with one secondary amino group), such as dimethylamine, diethylamine, bis(dodecyl)amine, or bis(hexadecyl)amine, etc.;

C2-C14 hydrocarbylene diamines (wherein the two amino groups are each independently primary or secondary amino group) optionally substituted with hydroxy on the C2-C14 hydrocarbylene, such as ethylenediamine, N-methylethylene diamine, N,N'-dimethylethylenediamine, 1,3-propanediamine, N-methyl, N'-ethyl-1,3-propanediamine, butanediamine (including various isomers such as 1,2 or 1,3- or 1,4-butanediamine), 3,6-dihydroxydecanediamine, dodecanediamine, p- or m-phenylenediamine, 3,3'-dichloro-4,4'-diphenylmethanediamine (MOCA), or piperazine, etc.;

C4-C16 polyalkylene polyamines optionally substituted with hydroxy on the C4-C16 hydrocarbylene group, such as diethylenetriamine, triethylenetetramine, tetraethylenepentamine, pentaethylenehexamine amine, dipropylenetriamine, tripropylenetetramine, tris(2-hydroxy-1,3-propylene)tetramine or tetrakis(2-hydroxy-1,3-propylene)pentamine; etc.;

C3-C18 organic triamines optionally substituted with hydroxyl having three primary amino groups or C5-C18 organic tetraamines optionally substituted with hydroxyl having four primary amino groups, such as 1,3,5-triamino-cyclohexane, 1,3,5-tris(aminoethyl)-cyclohexane, 1,3,5-tris(aminopropyl)-1,3,5-hexahydrotriazine, 1,3,5-tris(methylaminopropyl)-1,3,5-hexahydrotriazine, or, melamine, pentaerythrityl tetramine, etc.; or C2-C10 alcohol amines, such as monoethanolamine, diethanolamine, monopropanolamine, dipropanolamine, monoisopropanolamine, diisopropanolamine, monobutanolamine, or dibutanolamine, etc.

Preferably, in step B), the molar ratio of the α-carbonyl alkenyl ester having the general formula (I) to the compound having the general formula (IV) is 1:1-2, preferably 1:1:1-1.5, more preferably 1:1-1.2.

Preferably, the solvent is an organic solvent, preferably an aprotic organic solvent.

Preferably, the aprotic organic solvent is one or more of tetrahydrofuran, dimethyl sulfoxide, N,N-dimethylformamide and acetonitrile. Preference is given to dimethyl sulfoxide and/or N,N-dimethylformamide. More preferably, it is N,N-dimethylformamide.

Preferably, the molar ratio of the amount of the aprotic organic solvent to the amount of the compound shown in the general formula (I) is 30-180:1, preferably 50-150:1, more preferably 80-120:1.

Preferably, step B) comprises following steps: adding the α-carbonyl alkenyl ester having the general formula (I) and the solvent together in a proportion to a reactor, and then adding the compound having the general formula (IV), reacting at −40~100° C. (preferably 0~60° C., more preferably 30~50° C.) with stirring for 0.05-24 h (preferably 0.5-15 h, more preferably 1-10 h), using TLC to monitor the completion of the reaction, and obtaining the amide having the general formula (V) by column chromatography after the completion of the reaction.

According to a fourth embodiment of the present invention, there is provided a method for preparing an amide having the general formula (V), comprising:

C) reacting an allenone compound having the general formula (II) with a carboxylic acid having the general formula (III) in a first solvent, optionally separating the reaction mixture, and then obtaining the α-carbonyl alkenyl ester; and D) reacting the α-carbonyl alkenyl ester prepared in step C) with a compound having the general formula (IV) in a second solvent, optionally separating the reaction mixture, to obtain the amide compound having the general formula (V):

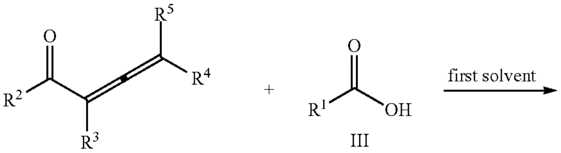

II
III

-continued

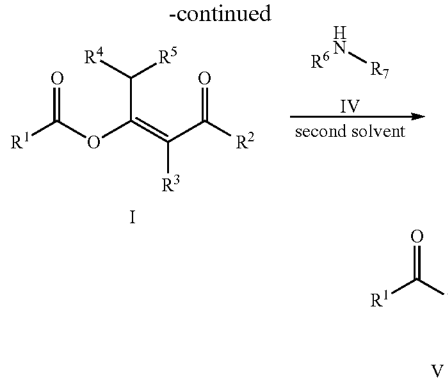

I

V wherein the respective definitions of $R^1$, $R^2$, $R^3$, $R^4$ or $R^5$ (also including their preferred definitions) are the same as the definitions of the corresponding groups $R^1$, $R^2$, $R^3$, $R^4$ or $R^5$ in the first embodiment described above (also including their preferred definitions), or the same as the definitions for the corresponding groups $R^1$, $R^2$, $R^3$, $R^4$ or $R^5$ in the second embodiment above (also including their preferred definitions);

the respective definitions of $R^6$ or $R^7$ (also including their preferred definitions) are the same as those of the corresponding groups $R^6$ or $R^7$ in the third embodiment above (also including their preferred definitions).

The compound having the general formula (IV) above is the same compound having at least one N—H bond as in the third embodiment above.

The first solvent and the second solvent may be the same or different.

Preferably, the first solvent is an organic solvent, preferably an aprotic organic solvent.

Preferably, the first solvent is selected from one or more of dichloromethane, trichloromethane, 1,2-dichloroethane, acetonitrile, tetrahydrofuran, water, diethyl ether and toluene, preferably one or more of dichloromethane, trichloromethane and 1,2-dichloroethane. More preferably, the first solvent is 1,2-dichloroethane.

Preferably, the second solvent is an organic solvent, preferably an aprotic organic solvent.

Preferably, the second solvent is selected from one or more of tetrahydrofuran, dimethyl sulfoxide, N,N-dimethylformamide, and acetonitrile. Preference is given to dimethyl sulfoxide and/or N,N-dimethylformamide. More preferably, the second solvent is N,N-dimethylformamide.

According to a fifth embodiment of the present invention, there is provided the use of the α-carbonyl alkenyl ester having the general formula (I) described in the first embodiment or prepared by the method described in the second embodiment, especially as amidation reagents for amino acids or polypeptide chains. The α-carbonyl alkenyl ester having the general formula (I) is applied in the method for solid-phase synthesis of polypeptide chain, and the method mainly comprises the following steps:

1) coupling a resin solid phase carrier with the terminal amino acid of a target polypeptide chain sequence or an α-carbonyl alkenyl ester corresponding to the terminal amino acid of a target polypeptide chain sequence in a solvent in the presence of a base or a catalyst to obtain PG-AA-resin;
2) according to the sequence of the target polypeptide chain to be synthesized, sequentially adding an α-carbonyl alkenyl ester corresponding to the amino acids of the sequence and the catalyst, and coupling in a solvent to obtain the PG-AA-AA-resin;
3) deprotecting and cleaving the PG-AA-AA-resin, and removing the side chain protecting group and the resin to obtain crude peptide;
4) purifying and freeze-drying to obtain the target polypeptide chain;

wherein PG refers to the protective group at the end of the main chain of the polypeptide chain on the solid phase carrier, and AA refers to a single amino acid residue on the main chain of the polypeptide chain on the solid phase carrier.

Preferably, the protective group at the end of the main chain of the polypeptide chain on the solid support in step 1) is selected from one or more of fluorene methoxycarbonyl (Fmoc), benzyloxycarbonyl (Cbz), tert-butoxycarbonyl (Boc), allyloxy carbonyl (Alloc), acetyl (Ac), methyl (Me), ethyl (Et), tert-butyl (tBu), trityl (Trt) or benzyl (Bn). Preferably, the protecting group is selected from one of fluorenemethoxycarbonyl (Fmoc) or tert-butoxycarbonyl (Boc), preferably fluorenemethoxycarbonyl (Fmoc).

Preferably, the main chain protecting group protecting the terminal amino group on the main chain is selected from one of fluorenemethoxycarbonyl (Fmoc), benzyloxycarbonyl (Cbz), tert-butoxycarbonyl (Boc), allyloxycarbonyl (Alloc), and acetyl (Ac).

Preferably, the side chain protecting group protecting the amine functional group on the side chain is selected from one or more of fluorenemethoxycarbonyl (Fmoc), benzyloxycarbonyl (Cbz), tert-butoxycarbonyl (Boc), allyloxycarbonyl (Alloc), acetyl group (Ac), methyl group (Me), ethyl group (Et), tert-butyl group (tBu), trityl group (Trt) and benzyl group (Bn).

Preferably, the resin solid phase carrier in step 1) is selected from one of Marrifield resin, Wang resin, 2-CTC resin, and MBHA resin.

Preferably, the α-carbonyl alkenyl ester is selected from one or more of those having the general formula (I) and wherein $R^1$ is a protected α-aminoalkyl, a protected β-aminoalkyl, a protected γ-aminoalkyl, or a protected polypeptide chain alkyl. Preferably, $R^1$ is a protected α-amino C1-C20 hydrocarbyl (preferably a C2-C10 hydrocarbyl), a protected β-amino C2-C20 hydrocarbyl (preferably a C3-C10 hydrocarbyl), a protected γ-amino C3-C20 hydrocarbyl (preferably C4-C10 hydrocarbyl), a protected polypeptide chain C1-C20 hydrocarbyl (preferably C2-C15 hydrocarbyl). The hydrocarbyl group mentioned here is preferably an alkyl, an alkenyl or a cycloalkyl.

Preferably, in step 1) and step 2), the catalyst is selected from one of HOAt (1-hydroxy-7-azobenzotriazole), HOBt (1-hydroxybenzotriazole), HOOBt (3-hydroxy-1,2,3-benzotriazin-4(3H)-one), HOSu (N-hydroxysuccinimide), COMU ((1-Cyano-2-ethoxy-2-oxoethylidenaminooxy)dimethyl amino-morpholino-carbenium hexafluorophosphate) and HOPHT (N-hydroxyphthalimide), preferably HOAt (1-hydroxy-7-azobenzotriazole) or HOBt (1-hydroxybenzotriazole), more preferably HOBt (1-hydroxybenzotriazole).

Preferably, in step 1), the base is selected from one or more of 4-dimethylaminopyridine, pyridine, N-methylimidazole, N,N-diisopropylethylamine (DIEA), preferably it is N,N-diisopropylethylamine (DIEA).

Preferably, step 2) also includes:

201) using a deprotection reagent to remove the protecting group PG on the PG-AA-resin to obtain H-AA-resin;

wherein, when the protective group at the end of the main chain of the polypeptide chain on the solid carrier is Fmoc (fluorene methoxycarbonyl), the deprotection reagent is N,N-dimethylformamide solution of piperidine, and its addition amount is 1-100 times, preferably 2-80 times, more preferably 3-50 times the molar amount of PG-AA-resin; when the protective group at the end of the main chain of the polypeptide chain on the solid carrier is Boc (tert-butoxycarbonyl), the deprotection reagent is dichloromethane solution of trifluoroacetic acid, and its addition amount is 1-100 times, preferably 2-80 times, more preferably 3-50 times the molar amount of PG-AA-resin;

202) in the presence of a catalyst, adding α-carbonyl alkenyl ester corresponding to PG-AA-OH, and coupling in a solvent to obtain PG-AA-AA-resin;

203) according to the sequence of the target peptide chain, sequentially repeating step 201) and step 202) to carry out coupling and deprotecting process to extend the peptide chain.

Preferably, in step 1), the amount of the catalyst used is 0.3-10 times, preferably 1-5 times, more preferably 1-3 times the molar amount of the resin used as the solid support.

Preferably, the amount of the base used is 1-10 times, preferably 1-6 times, more preferably 1-3 times the molar amount of the PG-AA-resin.

Preferably, in step 201), the amount of the deprotection reagent added is 1-100 times, preferably 2-80 times, more preferably 3-50 times the molar amount of the PG-AA-resin.

Preferably, in step 202), the amount of the α-carbonyl alkenyl ester is 1-10 times, preferably 1-6 times, more preferably 1-3 times the molar amount of the PG-AA-resin.

Preferably, the amount of the catalyst used is 0.3-10 times, preferably 0.5-5 times, more preferably 1-3 times the molar amount of the PG-AA-resin.

Preferably, the solvent is an organic solvent, preferably an aprotic organic solvent.

Preferably, the aprotic organic solvent is selected from one or two of N,N-dimethylformamide (DMF) and dimethylsulfoxide (DMSO), preferably N,N-dimethylformamide Amide (DMF).

Preferably, the mass ratio of the amount of the solvent to the amount of the PG-AA-resin is 10-300:1, preferably 20-200:1, more preferably 30-100:1.

Preferably, in step 4), the purification is carried out by reversed high performance liquid chromatography, the chromatography column is a C18 reversed silica gel column, and the mobile phase is water and acetonitrile.

Preferably, the polypeptide cleavage resin is cleaved with a cleavage cocktail (for example, the cleavage cocktail is trifluoroacetic acid:triisopropylsilane:water=95:2.5:2.5 or the cleavage solution is trifluoroacetic acid:ethanedithiol: triisopropyl silane:water=92.5:2.5:2.5:2.5).

In the present invention, the resin solid phase carrier and the terminal amino acid of the target polypeptide chain sequence or the α-carbonyl alkenyl ester corresponding to the terminal amino acid are coupled in a solvent in the presence of a base or a catalyst to obtain PG-AA-resin: when a resin solid phase carrier (such as 2-CTC resin) is reacted with the terminal amino acid of the target polypeptide chain sequence, the reaction is preferably carried out in a condition with the presence of a base (the base is selected from one or more of 4-dimethylaminopyridine, pyridine, N-methylimidazole, N,N-diisopropylethylamine (DIEA), preferably N,N-diisopropyl ethylamine (DIEA)). When a resin solid phase carrier (such as MBHA resin) is reacted with an α-carbonyl alkenyl ester corresponding to the terminal amino acid of the target polypeptide chain sequence, the reaction is preferably carried out in condition with the presence of a catalyst (the catalyst is selected from one or more of HOAt (1-hydroxy-7-azobenzotriazole), HOBt (1-hydroxybenzotriazole), HOOBt (3-hydroxy-1,2,3-benzotriazin-4(3H)-one), HOSu (N-hydroxysuccinimide), COMU ((1-Cyano-2-ethoxy-2-oxoethylidenaminooxy)dimethyl-amino-morpholino-carbenium hexafluorophosphate), HOPHT (N-hydroxyphthalimide). If other resin solid-phase carrier (such as Wang resin) is selected, it can also optionally use more suitable condensation reagents, according to different combinations of the resinsolid-phase carrier and the terminal amino acid of the target polypeptide chain sequence or α-carbonyl alkenyl esters corresponding to the end amino acid.

In the present invention, the protection in the protected α-aminoalkyl, protected β-aminoalkyl, protected γ-aminoalkyl and polypeptide chain alkyl refers to protecting the terminal amino group on the main chain, the group protecting the terminal amino group on the main chain is the main chain protecting group, and the main chain protecting group protecting the terminal amino group on the main chain is selected from one of Fmoc (fluorenemethoxycarbonyl), Cbz (benzyloxycarbonyl), Boc (tert-butoxycarbonyl), Alloc (allyloxycarbonyl), and Ac (acetyl). The purpose of protecting the terminal amino group on the main chain is to avoid the influence on the terminal amino group in the reaction of synthesizing the compound with the general formula (I) using the compound with the general formula (II) and the compound with the general formula (III).

Further, protected α-aminoalkyl, protected β-aminoalkyl, protected γ-aminoalkyl and polypeptide chain alkyl can protect the terminal amino group on the main chain and also protect the functional group on the side chain, and the functional group to be protected on the side chain is selected from one or more of hydroxyl, sulfhydryl, amino, primary amido, and carboxyl groups, and the group that protects the functional group on the side chain is the side chain protecting group, the side chain protecting group protecting the functional group on the side chain is selected from one or more of Fmoc (fluorenemethoxycarbonyl), Cbz (benzyloxycarbonyl), Boc (tert-butoxycarbonyl), Alloc (allyloxycarbonyl)), Ac (acetyl), Me (methyl), Et (ethyl), tBu (tert-butyl), Trt (trityl), Bn (benzyl). The carboxylic acids with a main chain protecting group or with both a main chain protecting group and a side chain protecting group can be obtained through synthesis or direct purchase. The purpose of protecting the terminal amino group on the main chain and the functional group on the side chain is to protect the terminal amino group and the functional group on the side chain from the influence of the reaction process of synthesizing the compound represented by the general formula (I) using the compound represented by the general formula (II) and the compound represented by the general formula (III) (for example, the groups will react with each other or prevent the progress of the target reaction, etc.).

In the present invention, the α-carbonyl alkenyl esters are used as intermediates in the preparation of the amides with the general formula (V). Without additives and catalysts, the "one pot two-step" method can also be used to obtain the compound shown in formula V:

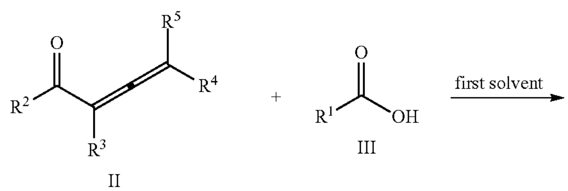

II III

-continued

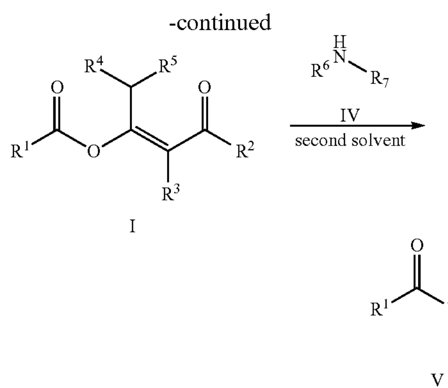

I

V wherein, the definitions of $R^1$, $R^2$, $R^3$, $R^4$, $R^5$, $R^6$ and $R^7$ (including their preferred definitions) are same as those in the fourth embodiment above.

Further, the present invention can also directly use the compound shown in formula II and the compound shown in formula III as raw materials, and by mediating of the compound shown in formula I, synthesize amide bond and peptide bond by a "one-pot two-step" method. Compared with the above-mentioned "one-pot, one-step" reaction (which needs to conduct two times), the operation is simpler, and the intermediate shown in the formula I does not need to be separated and purified. After removing the reaction solvent in the first step, the aprotic organic solvent and the compound of formula IV are added to complete the reaction.

The specific steps of the "one-pot, two-step" method are as follows: the compound having the general formula (II) and a first solvent (the first solvent is an organic solvent, the organic solvent is an aprotic organic solvent, the aprotic organic solvent is selected from dichloromethane, trichloromethane, 1,2-dichloroethane, acetonitrile, tetrahydrofuran, water, diethyl ether or toluene, preferably dichloromethane, trichloromethane or 1,2-dichloroethane, more preferably 1,2-dichloroethane. The molar ratio of the amount of the aprotic organic solvent to the amount of the allenone compound shown in formula II is 70-170:1, preferably 90-150:1, more preferably 110-130:1) are added into a reactor in proportion, and then the carboxylic acid having the general formula (III) is added, the reaction is carried out at 0-100° C. (preferably 20-60° C., more preferably 30-50° C.) under stirring for 0.5-320 h (preferably 1-240 h, more preferably 5-180 h). TLC is used to monitor the end of the reaction, and the reaction solvent is removed (preferably by vacuum) after the end of the reaction. Then a second solvent (the second solvent is an organic solvent, the organic solvent is an aprotic organic solvent, the aprotic organic solvent is selected from one or more of tetrahydrofuran, dimethyl sulfoxide, N,N-dimethylformamide and acetonitrile, preferably dimethyl sulfoxide and/or N,N-dimethylformamide, more preferably N,N-dimethylformamide. The molar ratio of the amount of the aprotic organic solvent to the amount of the compound shown in formula I is 30-180:1 (preferably 50-150:1, more preferably 80-120:1) and the compound with general formula (IV) are added to the reaction system and reacted for 0.05-24 h (preferably 0.5-15 h, more preferably 1-10 h) at −40~100° C. (preferably 0~60° C., more preferably 30~50° C.) under stirring, and the end of the reaction is monitored by TLC. After the reaction is completed, water (preferably deionized water) is added to the reaction system, and then the resulting liquid is extracted with ethyl acetate for 1-5 times (preferably 2-3 times). The organic layers are then combined, and the organic layers are washed with water (preferably deionized water) 1-5 times (preferably 2-3 times). Finally, after drying (preferably with anhydrous magnesium sulfate) and recrystallization, an amide having the general formula (V) is obtained.

In the present invention, the inventors found through research that carboxylic acids can carry out 1,4-addition react with alkenones to obtain corresponding α-carbonyl alkenyl esters, which are relatively active, can undergo an efficient aminolysis reaction with primary or secondary amines to obtain corresponding amides. Moreover, because the aminolysis reaction in this step is fast, the reaction can occur without additional catalysts and additives, and the racemization of α-chiral carboxylic acids during the activation process can be well inhibited. As a kind of condensation reagent, alkenones have the advantages of simple preparation, low molecular weight and no racemization in activation of α-chiral carboxylic acids. At the same time, the reaction conditions are mild and the operation is simple. Its by-product benzoyl acetone also has important value in synthesis, which conforms to the direction of green chemistry in modern chemistry and has excellent atomic economy. Therefore, it will be a new, efficient and practical method to synthesize the amide bond and peptide bond by using alkenones.

Compared with the prior art, the beneficial technical effects possessed by the present invention are as follows:

1. The present invention provides a method for synthesizing α-carbonyl alkenyl esters, and the compounds are also used to react with primary or secondary amines to prepare amides, thereby developing an amide bond and peptide bond formation method using carboxylic acids and amines as starting materials and allenones as condensing reagents. The α-carbonyl alkenyl esters of amino acids are used as polypeptide synthesis building blocks in solid-phase synthesis of polypeptides.
2. The method has advantages of mild reaction conditions, simple operation and high yield. Compared with the existing amide bond condensation reagents, allenones have the advantages of simple preparation, good stability, small molecular weight, no racemization when activating α-chiral carboxylic acids, etc., which is in line with the direction of green chemistry in modern chemistry, with excellent atom economy. It is a new type of amide bond and peptide bond condensation reagent.

DETAILED DESCRIPTION OF THE INVENTION

Figure 1:
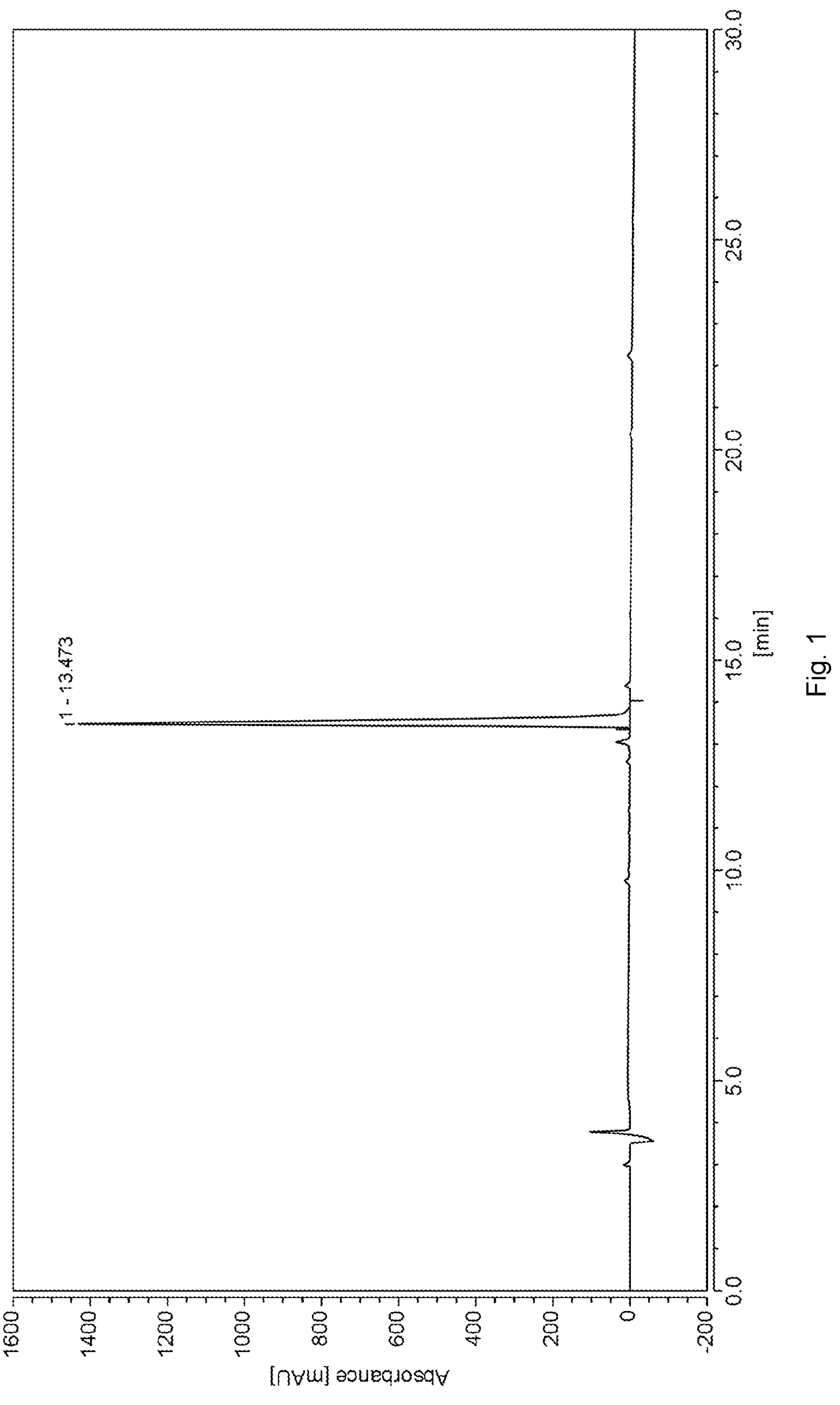
FIG. 1 is HPLC chart of leucine enkephalin crude product.

The technical solutions of the present invention are illustrated below with examples, and the claimed scope of the present invention includes but is not limited to the following embodiments.

Preparation Example 1

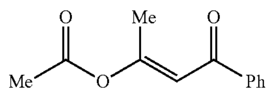

In a clean 4 mL reaction vial, allenone (0.20 mmol) and 2 mL of 1,2-dichloroethane (DCE) were added, followed by acetic acid (0.22 mmol); the reaction was then carried out at room temperature for 8 h under stirring, TLC is used to monitor the end of the reaction; after the completion of the reaction, the pure product was obtained by column chromatography as a colorless oily liquid with a yield of 93%.

$^1$H NMR (400 MHz, $CDCl_3$) δ 7.92 (d, J=7.1 Hz, 2H), 7.55 (t, J=7.4 Hz, 1H), 7.46 (t, J=7.6 Hz, 2H), 6.79 (s, 1H), 2.41 (s, 3H), 2.23 (s, 3H).

$^{13}$C NMR (100 MHz, $CDCl_3$) δ 190.4, 168.2, 163.7, 138.7, 132.8, 128.6, 128.1, 113.6, 21.3, 19.0 ppm. HRMS m/z (ESI) calcd for $C_{12}H_{12}NaO_3$ $(M+Na)^+$: 227.0679, found: 227.0685.

Preparation Example 2

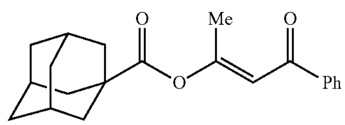 [SMILES: C/C(=C\C(=O)c1ccccc1)OC(=O)C12CC3CC(CC(C3)C1)C2]

In a clean 4 mL reaction vial, allenone (0.20 mmol) and 2 mL of 1,2-dichloroethane (DCE) were added, followed by adamantanecarboxylic acid (0.22 mmol); then the reaction was carried out at room temperature for 9 h under stirring, TLC is used to monitor the completion of the reaction; after the reaction, the pure product was obtained by column chromatography as a colorless oily liquid with a yield of 87%.

$^1$H NMR (400 MHz, $CDCl_3$) δ 7.92 (d, J=7.0 Hz, 2H), 7.54 (t, J=7.3 Hz, 1H), 7.45 (t, J=7.5 Hz, 2H), 6.74 (s, 1H), 2.38 (s, 3H), 2.08 (s, 3H), 1.99 (d, J=2.9 Hz, 6H), 1.86-1.68 (m, 6H).

$^{13}$C NMR (100 MHz, $CDCl_3$) δ 190.4, 175.1, 164.5, 138.8, 132.7, 128.5, 128.1, 113.3, 41.2, 38.6, 36.4, 27.8, 19.0 ppm.

HRMS m/z (ESI) calcd for $C_{21}H_{25}O_3$ $(M+H)^+$: 325.1798, found: 325.1830.

Preparation Example 3

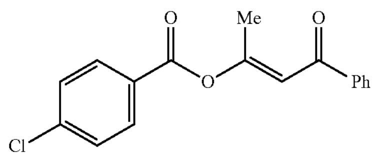 [SMILES: C/C(=C\C(=O)c1ccccc1)OC(=O)c1ccc(Cl)cc1]

In a clean 4 mL reaction vial were added allenone (0.20 mmol) and 2 mL of 1,2-dichloroethane (DCE), followed by 4-chlorobenzoic acid (0.22 mmol); then the reaction was stirred at room temperature for 12 h, using TLC to monitor the end of the reaction; after the end of the reaction, the pure product obtained by column chromatography was a colorless oily liquid with a yield of 93%.

$^1$H NMR (400 MHz, $CDCl_3$) δ 8.05 (d, J=8.6 Hz, 2H), 7.95 (d, J=7.0 Hz, 2H), 7.55 (t, J=7.3 Hz, 1H), 7.51-7.41 (m, 4H), 6.93 (s, 1H), 2.52 (s, 3H).

$^{13}$C NMR (100 MHz, $CDCl_3$) δ 190.2, 163.7, 163.2, 140.5, 138.6, 132.9, 131.5, 129.1, 128.6, 128.2, 127.6, 114.0, 19.0 ppm.

HRMS m/z (ESI) calcd for $C_{17}H_{14}ClO_3$ $(M+H)^+$: 301.0626, found: 301.0598.

Preparation Example 4

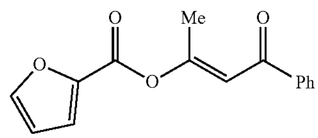 [SMILES: C/C(=C\C(=O)c1ccccc1)OC(=O)c1ccco1]

In a clean 4 mL reaction vial were added allenone (0.20 mmol) and 2 mL of 1,2-dichloroethane (DCE), followed by 2-furoic acid (0.22 mmol); then the reaction was stirred at room temperature for 8 h, using TLC to monitor the end of the reaction; after the completion of the reaction, the pure product was obtained by column chromatography as a colorless oily liquid with a yield of 87%.

$^1$H NMR (400 MHz, $CDCl_3$) δ 7.94 (d, J=7.1 Hz, 2H), 7.67 (dd, J=1.8, 0.9 Hz, 1H), 7.55 (t, J=7.4 Hz, 1H), 7.46 (t, J=7.5 Hz, 2H), 7.34 (dd, J=3.5, 0.8 Hz, 1H), 6.95 (s, 1H), 6.59 (dd, J=3.5, 1.8 Hz, 1H), 2.51 (s, 3H).

$^{13}$C NMR (100 MHz, $CDCl_3$) δ 190.2, 163.1, 155.7, 147.4, 143.6, 138.6, 132.9, 128.6, 128.2, 119.9, 113.9, 112.3, 18.9 ppm.

HRMS m/z (ESI) calcd for $C_{15}H_{12}NaO_4$ $(M+Na)^+$: 279.0628, found: 279.0637.

Preparation Example 5

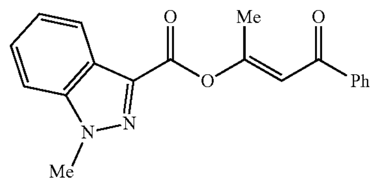 [SMILES: C/C(=C\C(=O)c1ccccc1)OC(=O)c1nn(C)c2ccccc12]

To a clean 4 mL reaction vial were added allenone (0.20 mmol) and 2 mL of 1,2-dichloroethane (DCE), followed by 1-methylindazole-3-carboxylic acid (0.22 mmol); then the reaction was stirred at room temperature for 28 h, and the completion of the reaction was monitored by TLC; after the reaction, the pure product was obtained by column chromatography as a light yellow oily liquid with a yield of 90%.

$^1$H NMR (400 MHz, $CDCl_3$) δ 8.24 (d, J=8.2 Hz, 1H), 7.97 (d, J=7.2 Hz, 2H), 7.61-7.42 (m, 5H), 7.43-7.33 (m, 1H), 7.03 (s, 1H), 4.23 (s, 3H), 2.62 (s, 3H).

$^{13}$C NMR (100 MHz, $CDCl_3$) δ 190.3, 163.9, 159.8, 141.2, 138.7, 133.5, 132.9, 128.6, 128.2, 127.3, 124.0, 123.7, 121.9, 114.3, 109.8, 36.7, 19.3 ppm.

HRMS m/z (ESI) calcd for $C_{19}H_{16}N_2NaO_3$ $(M+Na)^+$: 343.1053, found: 343.1056.

Preparation Example 6

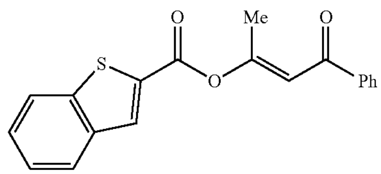 [SMILES: C/C(=C\C(=O)c1ccccc1)OC(=O)c1cc2ccccc2s1]

In a clean 4 mL reaction vial were added allenone (0.20 mmol) and 2 mL of 1,2-dichloroethane (DCE), followed by benzothiophene-2-carboxylic acid (0.22 mmol); then the reaction was stirred at room temperature for 12 h, and the completion of the reaction was monitored by TLC; after the reaction, the pure product was obtained by column chromatography as a colorless oily liquid with the yield of 85%.

$^1$H NMR (400 MHz, $CDCl_3$) δ 8.19 (s, 1H), 8.02-7.86 (m, 4H), 7.65-7.34 (m, 5H), 7.00 (s, 1H), 2.55 (s, 3H).

$^{13}$C NMR (100 MHz, $CDCl_3$) δ 190.3, 163.4, 160.1, 142.8, 138.6, 138.6, 132.9, 132.2, 132.2, 128.6, 128.2, 127.6, 125.9, 125.2, 122.9, 113.9, 19.0 ppm.

HRMS m/z (ESI) calcd for $C_{19}H_{14}NaO_3S$ $(M+Na)^+$: 345.0556, found: 345.0563.

Preparation Example 7

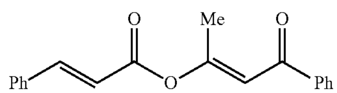 [SMILES: C/C(=C\C(=O)c1ccccc1)OC(=O)/C=C/c1ccccc1]

In a clean 4 mL reaction vial were added allenone (0.20 mmol) and 2 mL of 1,2-dichloroethane (DCE), followed by cinnamic acid (0.22 mmol); then the reaction was stirred at room temperature for 10 h, using TLC to monitor the completion of the reaction; after the reaction, the pure product was obtained by column chromatography as a colorless oily liquid with a yield of 96%.

$^1$H NMR (400 MHz, $CDCl_3$) δ 7.94 (d, J=7.0 Hz, 2H), 7.82 (d, J=16.0 Hz, 1H), 7.62-7.50 (m, 3H), 7.48-7.40 (m, 5H), 6.90 (s, 1H), 6.52 (d, J=16.0 Hz, 1H), 2.49 (s, 3H).

$^{13}$C NMR (100 MHz, $CDCl_3$) δ 190.4, 164.2, 163.9, 147.2, 138.8, 134.0, 132.8, 131.0, 129.1, 128.6, 128.4, 128.2, 116.9, 113.5, 19.1 ppm.

HRMS m/z (ESI) calcd for $C_{19}H_{16}NaO_3$ $(M+Na)^+$: 315.0992, found: 315.0999.

Preparation Example 8

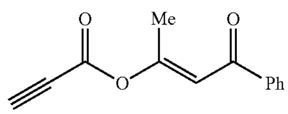 [SMILES: C#CC(=O)O/C(C)=C/C(=O)c1ccccc1]

In a clean 4 mL reaction vial were added allenone (0.20 mmol) and 2 mL of 1,2-dichloroethane (DCE), followed by propargylic acid (0.22 mmol); then the reaction was stirred at room temperature for 1.5 h, the completion of the reaction was monitored by TLC; after the reaction, the pure product was obtained by column chromatography as a colorless oily liquid with a yield of 87%.

$^1$H NMR (400 MHz, $CDCl_3$) δ 7.91 (d, J=7.0 Hz, 2H), 7.56 (t, J=7.4 Hz, 1H), 7.46 (t, J=7.6 Hz, 2H), 6.85 (s, 1H), 3.09 (s, 1H), 2.42 (s, 3H);

$^{13}$C NMR (100 MHz, $CDCl_3$) δ 189.9, 162.2, 149.5, 138.2, 133.1, 128.6, 128.1, 114.3, 76.9, 73.9, 18.5 ppm.

HRMS m/z (ESI) calcd for $C_{13}H_{10}NaO_3$ $(M+Na)^+$: 237.0528, found: 237.0635.

Preparation Example 9

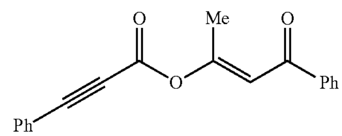 [SMILES: C/C(=C\C(=O)c1ccccc1)OC(=O)C#Cc1ccccc1]

In a clean 4 mL reaction vial were added allenone (0.20 mmol) and 2 mL of 1,2-dichloroethane (DCE), followed by phenylpropargylic acid (0.22 mmol); then the reaction was stirred at room temperature for 4 h, using TLC to monitor the end of the reaction; after the end of the reaction, the pure product obtained by column chromatography was a colorless oily liquid with a yield of 93%.

$^1$H NMR (400 MHz, $CDCl_3$) δ 7.93 (d, J=7.0 Hz, 2H), 7.63 (d, J=7.0 Hz, 2H), 7.56 (t, J=7.3 Hz, 1H), 7.54-7.36 (m, 5H), 6.90 (s, 1H), 2.48 (s, 3H).

$^{13}$C NMR (100 MHz, $CDCl_3$) δ 190.1, 162.8, 150.9, 138.5, 133.2, 133.0, 131.2, 128.7, 128.6, 128.2, 119.0, 114.2, 88.8, 80.0, 18.8 ppm.

HRMS m/z (ESI) calcd for $C_{19}H_{14}NaO_3$ $(M+Na)^+$: 313.0835, found: 313.0841.

Preparation Example 10

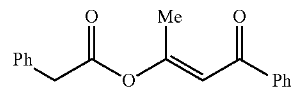 [SMILES: C/C(=C\C(=O)c1ccccc1)OC(=O)Cc1ccccc1]

In a clean 4 mL reaction vial were added allenone (0.20 mmol) and 2 mL of 1,2-dichloroethane (DCE), followed by phenylacetic acid (0.22 mmol); then the reaction was stirred at room temperature for 5 h, using TLC to monitor the completion of the reaction; after the reaction, the pure product was obtained by column chromatography as a light yellow oily liquid with a yield of 88%.

$^1$H NMR (400 MHz, $CDCl_3$) δ 7.90 (d, J=7.0 Hz, 2H), 7.54 (t, J=7.4 Hz, 1H), 7.45 (t, J=7.7 Hz, 2H), 7.41-7.28 (m, 5H), 6.78 (s, 1H), 3.79 (s, 2H), 2.37 (s, 3H);

$^{13}$C NMR (100 MHz, $CDCl_3$) δ 190.3, 168.9, 163.6, 138.6, 132.9, 132.8, 129.2, 128.8, 128.5, 128.1, 127.5, 113.6, 41.5, 18.8 ppm.

HRMS m/z (ESI) calcd for $C_{18}H_{16}NaO_3$ $(M+Na)^+$: 303.0997, found: 303.1013.

Preparation Example 11

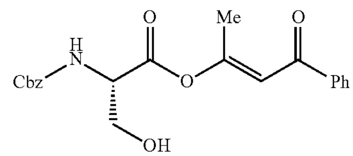 [SMILES: C/C(=C\C(=O)c1ccccc1)OC(=O)[C@H](CO)NC(=O)OCc1ccccc1]

In a clean 4 mL reaction vial were added allenone (0.20 mmol) and 2 mL of 1,2-dichloroethane (DCE) followed by Cbz-L-Ser-OH (0.22 mmol); then the reaction was stirred at room temperature for 12 h, and the completion of the reaction was monitored by TLC; after the reaction was completed, the pure product was obtained by column chromatography as a light yellow oily liquid with a yield of 87%.

$^1$H NMR (400 MHz, $CDCl_3$) δ 7.89 (d, J=7.6 Hz, 2H), 7.54 (t, J=7.4 Hz, 1H), 7.44 (t, J=7.7 Hz, 2H), 7.37-7.28 (m, 5H), 6.80 (s, 1H), 5.86 (d, J=8.0 Hz, 1H), 5.14 (s, 2H), 4.58 (s, 1H), 4.13 (d, J=7.4 Hz, 1H), 3.99 (d, J=11.3 Hz, 1H), 2.70 (s, 1H), 2.38 (s, 3H).

$^{13}$C NMR (100 MHz, $CDCl_3$) δ 190.3, 168.3, 163.2, 156.2, 138.4, 136.0, 133.0, 128.6, 128.6, 128.3, 128.2, 128.1, 114.1, 67.4, 63.0, 56.3, 18.7 ppm.

HRMS m/z (ESI) calcd for $C_{21}H_{21}NNaO_6$ $(M+Na)^+$: 406.1261, found: 406.1270.

Preparation Example 12

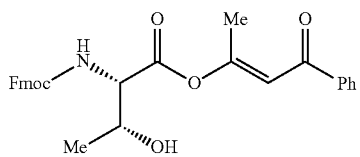

In a clean 4 mL reaction vial were added allenone (0.20 mmol) and 2 mL of 1,2-dichloroethane (DCE), followed by Fmoc-L-Thr-OH (0.22 mmol); then the reaction was stirred at room temperature for 6 h, and the completion of the reaction was monitored by TLC; after the reaction, the pure product was obtained by column chromatography as a light yellow oily liquid with a yield of 94%.

$^1$H NMR (400 MHz, $CDCl_3$) δ 7.88 (d, J=7.6 Hz, 2H), 7.75 (d, J=7.5 Hz, 2H), 7.60 (d, J=7.5 Hz, 2H), 7.53 (t, J=7.2 Hz, 1H), 7.47-7.33 (m, 4H), 7.29 (t, J=7.5 Hz, 2H), 6.80 (s, 1H), 5.76 (s, 1H), 4.46 (t, 4H), 4.23 (t, J=6.9 Hz, 1H), 2.39 (s, 4H), 1.30 (d, J=6.3 Hz, 3H).

$^{13}$C NMR (100 MHz, $CDCl_3$) δ 190.2, 168.8, 163.3, 156.8, 143.8, 143.6, 141.3, 138.4, 133.0, 128.6, 128.2, 127.8, 127.1, 125.0, 120.0, 114.0, 68.0, 67.3, 59.4, 47.2, 20.2, 18.8 ppm.

HRMS m/z (ESI) calcd for $C_{29}H_{27}NNaO_6$ $(M+Na)^+$: 508.1731, found: 508.1740.

Preparation Example 13

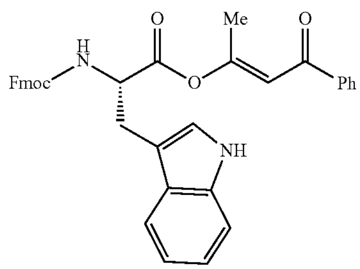

In a clean 4 mL reaction vial were added allenone (0.20 mmol) and 2 mL of 1,2-dichloroethane (DCE), followed by Fmoc-L-Trp-OH (0.22 mmol); then the reaction was stirred at room temperature for 12 h, and the completion of the reaction was monitored by TLC; after the reaction, the pure product was obtained by column chromatography as a light yellow oily liquid with a yield of 89%.

$^1$H NMR (400 MHz, $CDCl_3$) δ 8.28 (s, 1H), 7.81 (d, J=7.8 Hz, 2H), 7.78 (d, J=7.6 Hz, 2H), 7.66 (d, J=7.9 Hz, 1H), 7.60-7.50 (m, 3H), 7.48-7.37 (m, 5H), 7.34-7.28 (m, 2H), 7.23 (d, J=7.8 Hz, 1H), 7.16 (t, J=7.5 Hz, 1H), 7.04 (s, 1H), 6.54 (s, 1H), 5.47 (d, J=8.1 Hz, 1H), 4.93-4.83 (m, 1H), 4.52-4.34 (m, 2H), 4.23 (t, J=7.1 Hz, 1H), 3.50-3.30 (m, 2H), 2.30 (s, 3H);

$^{13}$C NMR (100 MHz, $CDCl_3$) δ 190.1, 169.7, 163.2, 155.7, 143.7, 143.6, 141.3, 141.2, 138.3, 136.1, 132.9, 128.5, 128.1, 127.7, 127.4, 127.0, 125.0, 123.0, 122.5, 120.0, 118.6, 113.8, 111.4, 109.4, 67.1, 54.8, 47.1, 27.9, 18.6 ppm.

HRMS m/z (ESI) calcd for $C_{41}H_{38}N_2NaO_7$ $(M+Na)^+$: 693.2571, found: 693.2583.

Preparation Example 14

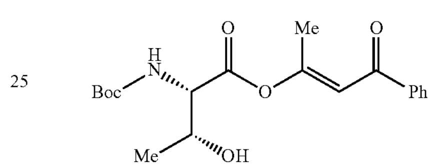

In a clean 4 mL reaction vial were added allenone (0.20 mmol) and 2 mL of 1,2-dichloroethane (DCE), followed by Boc-L-Thr-OH (0.22 mmol); then the reaction was stirred at room temperature for 8 h, and the completion of the reaction was monitored by TLC; after the reaction, the pure product was obtained by column chromatography as a light yellow oily liquid with a yield of 92%.

$^1$H NMR (400 MHz, $CDCl_3$) δ 7.90 (d, J=7.2 Hz, 2H), 7.54 (t, J=7.4 Hz, 1H), 7.45 (t, J=7.6 Hz, 2H), 6.81 (s, 1H), 5.40 (d, J=8.8 Hz, 1H), 4.45 (s, 1H), 4.39 (d, J=8.7 Hz, 1H), 2.40 (s, 3H), 2.29 (s, 1H), 1.47 (s, 9H), 1.32 (d, J=6.4 Hz, 3H);

$^{13}$C NMR (100 MHz, $CDCl_3$) δ 190.2, 169.1, 163.4, 156.1, 138.4, 132.9, 128.6, 128.2, 113.9, 80.4, 68.0, 59.0, 28.3, 20.2, 18.7 ppm.

HRMS m/z (ESI) calcd for $C_{19}H_{25}NNaO_6$ $(M+Na)^+$: 386.1850, found: 386.1837.

Preparation Example 15

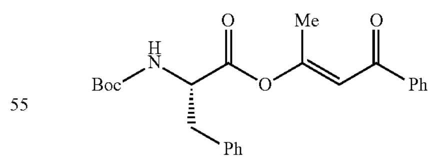

In a clean 4 mL reaction vial were added allenone (0.20 mmol) and 2 mL of 1,2-dichloroethane (DCE), followed by Boc-L-Phe-OH (0.22 mmol), then the reaction was stirred at room temperature for 8 h, and the completion of the reaction was monitored by TLC; after the reaction, the pure product was obtained by column chromatography as a light yellow oily liquid with a yield of 92%.

$^1$H NMR (400 MHz, $CDCl_3$) δ 7.88 (d, J=7.0 Hz, 2H), 7.55 (t, J=7.3 Hz, 1H), 7.45 (t, J=7.6 Hz, 2H), 7.38-7.28 (m,

3H), 7.23 (d, J=6.6 Hz, 2H), 6.64 (s, 1H), 5.05 (d, J=7.6 Hz, 1H), 4.69 (d, J=7.3 Hz, 1H), 3.17 (d, J=6.5 Hz, 2H), 2.33 (s, 3H), 1.44 (s, 9H).

$^{13}C$ NMR (100 MHz, $CDCl_3$) δ 190.1, 169.7, 163.3, 155.1, 138.5, 135.6, 132.9, 129.4, 128.8, 128.6, 128.2, 127.4, 113.8, 80.4, 54.8, 38.2, 28.3, 18.6 ppm.

HRMS m/z (ESI) calcd for $C_{24}H_{27}NNaO_5$ $(M+Na)^+$: 432.1781, found: 432.1787.

Preparation Example 16

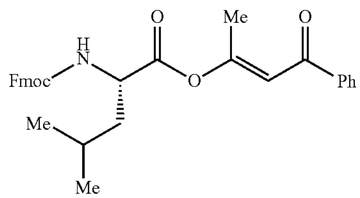

In a clean 4 mL reaction vial were added allenone (0.20 mmol) and 2 mL of 1,2-dichloroethane (DCE), followed by Fmoc-L-Leu-OH (0.22 mmol); then the reaction was stirred at room temperature for 3 h, and the completion of the reaction was monitored by TLC; after the reaction was completed, the pure product was obtained by column chromatography as a light yellow oily liquid with a yield of 99%.

$^1H$ NMR (400 MHz, $CDCl_3$) δ 7.90 (d, J=7.7 Hz, 2H), 7.75 (d, J=7.5 Hz, 2H), 7.59 (d, J=7.5 Hz, 2H), 7.53 (t, J=7.4 Hz, 1H), 7.43 (t, J=7.6 Hz, 2H), 7.38 (t, J=7.7 Hz, 2H), 7.29 (t, J=7.4 Hz, 2H), 6.79 (s, 1H), 5.27 (d, J=8.6 Hz, 1H), 4.55-4.48 (m, 1H), 4.44 (d, J=5.0 Hz, 2H), 4.23 (t, J=6.9 Hz, 1H), 2.40 (s, 3H), 1.81-1.71 (m, 2H), 1.69-1.59 (m, 1H), 1.00 (d, J=5.7 Hz, 6H).

$^{13}C$ NMR (10 MHz, $CDCl_3$) δ 190.2, 170.8, 163.3, 156.1, 143.8, 143.7, 141.4, 138.5, 133.0, 128.6, 128.2, 127.8, 127.1, 125.0, 120.1, 113.9, 67.1, 52.8, 47.2, 41.2, 24.9, 23.0, 21.7, 18.8 ppm.

HRMS m/z (ESI) calcd for $C_{31}H_{31}NNaO_5$ $(M+Na)^+$: 520.2094, found: 520.2105.

Preparation Example 17

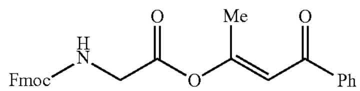

In a clean 4 mL reaction vial were added allenone (0.20 mmol) and 2 mL of 1,2-dichloroethane (DCE), followed by Fmoc-Gly-OH (0.22 mmol); then the reaction was stirred at room temperature for 36 h, and TLC was used to monitor the completion of the reaction; after the reaction, the pure product was obtained by column chromatography as a light yellow oily liquid with a yield of 95%.

$^1H$ NMR (400 MHz, $CDCl_3$) δ 7.92 (d, J=7.5 Hz, 2H), 7.77 (d, J=7.5 Hz, 2H), 7.61 (d, J=7.4 Hz, 2H), 7.56 (t, J=7.4 Hz, 1H), 7.46 (t, J=7.6 Hz, 2H), 7.41 (t, J=7.4 Hz, 2H), 7.32 (t, J=7.4 Hz, 2H), 6.84 (s, 1H), 5.45 (t, J=6.0 Hz, 1H), 4.46 (d, J=7.0 Hz, 2H), 4.25 (t, J=7.0 Hz, 1H), 4.16 (d, J=5.9 Hz, 2H), 2.42 (s, 3H).

$^{13}C$ NMR (100 MHz, $CDCl_3$) δ 190.1, 167.6, 162.9, 156.3, 143.6, 141.3, 138.3, 133.0, 128.6, 128.1, 127.7, 127.1, 125.0, 120.0, 113.9, 67.3, 47.0, 42.9, 18.7 ppm.

HRMS m/z (ESI) calcd for $C_{27}H_{23}NNaO_5$ $(M+Na)^+$: 464.1468, found: 464.1471.

Preparation Example 18

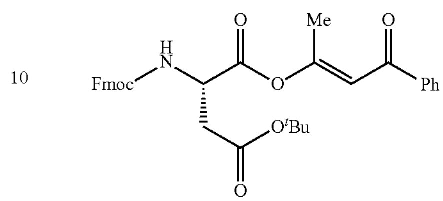

In a clean 4 mL reaction vial were added allenone (0.20 mmol) and 2 mL of 1,2-dichloroethane (DCE), followed by Fmoc-L-Asp(tBu)-OH (0.22 mmol); then the reaction was stirred at room temperature for 6 h, and the completion of the reaction was monitored by TLC; after the reaction, the pure product was obtained by column chromatography as a light yellow oily liquid with a yield of 95%.

$^1H$ NMR (400 MHz, $CDCl_3$) δ 7.92 (d, J=7.5 Hz, 2H), 7.77 (d, J=7.5 Hz, 2H), 7.62 (dd, J=7.2, 3.0 Hz, 2H), 7.55 (t, J=7.4 Hz, 1H), 7.45 (t, J=7.6 Hz, 2H), 7.40 (t, J=7.5 Hz, 2H), 7.32 (t, J=7.4 Hz, 2H), 6.82 (s, 1H), 5.93 (d, J=8.7 Hz, 1H), 4.83-4.74 (m, 1H), 4.54-4.44 (m, 1H), 4.44-4.35 (m, 1H), 4.27 (t, J=7.1 Hz, 1H), 3.08 (dd, J=17.3, 4.5 Hz, 1H), 2.87 (dd, J=17.3, 4.2 Hz, 1H), 2.42 (s, 3H), 1.50 (s, 9H.

$^{13}C$ NMR (100 MHz, $CDCl_3$) δ 190.0, 170.1, 168.7, 163.3, 155.9, 143.6, 141.2, 138.4, 132.9, 128.5, 128.1, 127.7, 127.0, 125.0, 119.9, 114.0, 82.3, 67.3, 50.6, 47.0, 37.8, 28.0, 18.5 ppm.

HRMS m/z (ESI) calcd for $C_{33}H_{35}NO_7$ $(M+H)^+$: 556.2330, found: 556.2325.

Preparation Example 19

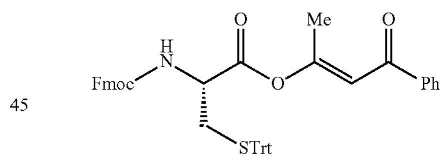

In a clean 4 mL reaction vial were added allenone (0.20 mmol) and 2 mL of 1,2-dichloroethane (DCE), followed by Fmoc-L-Cys(Trt)-OH (0.22 mmol); then the reaction was stirred at room temperature for 6 h, and the end of the reaction was monitored by TLC; after the reaction, the pure product was obtained by column chromatography as a light yellow oily liquid with a yield of 85%.

$^1H$ NMR (400 MHz, $CDCl_3$) δ 7.91 (d, J=7.7 Hz, 2H), 7.79 (dd, J=7.7, 3.0 Hz, 2H), 7.63 (d, J=6.7 Hz, 2H), 7.56 (t, J=7.4 Hz, 1H), 7.50-7.39 (m, 11H), 7.37-7.28 (m, 8H), 7.23 (d, J=7.1 Hz, 2H), 6.82 (s, 1H), 5.35 (d, J=8.2 Hz, 1H), 4.54-4.36 (m, 3H), 4.26 (t, J=7.0 Hz, 1H), 2.85 (dd, J=12.6, 6.4 Hz, 1H), 2.71 (dd, J=12.6, 4.6 Hz, 1H), 2.40 (s, 3H);

$^{13}C$ NMR (100 MHz, $CDCl_3$) δ 190.0, 168.2, 163.1, 155.5, 144.0, 143.7, 143.6, 141.2, 141.2, 138.3, 132.9, 129.4, 128.5, 128.1, 128.1, 127.7, 127.1, 127.0, 125.0, 125.0, 120.0, 113.8, 67.2, 67.2, 53.1, 47.0, 33.7, 18.6 ppm.

HRMS m/z (ESI) calcd for $C_{47}H_{39}NO_5S$ $(M+H)^+$: 752.2447, found: 752.2450.

Preparation Example 20

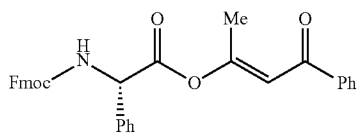

In a clean 4 mL reaction vial were added allenone (0.20 mmol) and 2 mL of 1,2-dichloroethane (DCE), followed by Fmoc-L-Phg-OH (0.22 mmol); then the reaction was stirred at room temperature for 3 h, and the completion of the reaction was monitored by TLC; after the reaction, the pure product was obtained by column chromatography as a light yellow oily liquid with a yield of 100%.

$^{1}$H NMR (400 MHz, $CDCl_3$) δ 7.88 (d, J=7.7 Hz, 2H), 7.77 (d, J=7.5 Hz, 2H), 7.61 (d, J=7.5 Hz, 2H), 7.55 (t, J=7.4 Hz, 1H), 7.48-7.38 (m, 9H), 7.31 (t, J=7.6 Hz, 2H), 6.75 (s, 1H), 5.87 (d, J=7.2 Hz, 1H), 5.53 (d, J=7.2 Hz, 1H), 4.62-4.34 (m, 2H), 4.24 (t, J=7.1 Hz, 1H), 2.32 (s, 3H).

$^{13}$C NMR (100 MHz, $CDCl_3$) δ 190.0, 168.5, 163.1, 155.4, 143.7, 143.6, 141.2, 138.3, 135.2, 132.9, 129.3, 129.1, 128.5, 128.1, 127.7, 127.3, 127.0, 125.0, 120.0, 113.7, 67.3, 58.3, 47.1, 18.4 ppm.

HRMS m/z (ESI) calcd for $C_{33}H_{27}NNaO_5$ $(M+Na)^+$: 540.1781, found: 540.1772.

Preparation Example 21

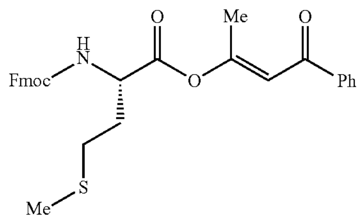

In a clean 4 mL reaction vial were added allenone (0.20 mmol) and 2 mL of 1,2-dichloroethane (DCE) followed by Fmoc-L-Met-OH (0.22 mmol), then, the reaction was stirred at room temperature for 3 h, and the completion of the reaction was monitored by TLC; after the reaction, the pure product was obtained by column chromatography as a light yellow oily liquid with a yield of 85%.

$^{1}$H NMR (400 MHz, $CDCl_3$) δ 7.91 (d, J=7.7 Hz, 2H), 7.77 (d, J=7.5 Hz, 2H), 7.61 (d, J=7.5 Hz, 2H), 7.56 (t, J=7.4 Hz, 1H), 7.45 (t, J=7.6 Hz, 2H), 7.40 (t, J=7.5 Hz, 2H), 7.32 (t, J=7.4 Hz, 2H), 6.82 (s, 1H), 5.51 (d, J=8.1 Hz, 1H), 4.76-4.58 (m, 1H), 4.47 (d, J=6.9 Hz, 2H), 4.25 (t, J=6.8 Hz, 1H), 2.61 (t, J=7.3 Hz, 2H), 2.41 (s, 3H), 2.37-2.20 (m, 1H), 2.17-2.01 (m, 4H).

$^{13}$C NMR (100 MHz, $CDCl_3$) δ 190.0, 169.7, 163.0, 155.9, 143.7, 143.5, 141.3, 138.3, 133.0, 128.6, 128.1, 127.7, 127.0, 124.9, 120.0, 113.9, 67.1, 53.3, 47.1, 31.3, 29.9, 18.7, 15.5 ppm.

HRMS m/z (ESI) calcd for $C_{30}H_{29}NNaO_5S$ $(M+Na)^+$: 538.1659, found: 538.1654.

Preparation Example 22

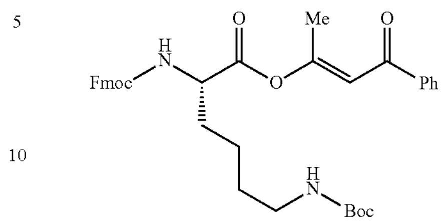

In a clean 4 mL reaction vial were added allenone (0.20 mmol) and 2 mL of 1,2-dichloroethane (DCE), followed by Fmoc-L-Lys(Boc)-OH (0.22 mmol); then the reaction was stirred at room temperature for 6 h, and the completion of the reaction was monitored by TLC; after the reaction, the pure product was obtained by column chromatography as a pale yellow oily liquid with a yield of 98%.

$^{1}$H NMR (400 MHz, $CDCl_3$) δ 7.90 (d, J=7.8 Hz, 2H), 7.75 (d, J=7.5 Hz, 2H), 7.61 (d, J=7.5 Hz, 2H), 7.53 (t, J=7.4 Hz, 1H), 7.45 (t, J=7.6 Hz, 2H), 7.39 (t, J=7.7 Hz, 2H), 7.30 (t, J=7.5 Hz, 2H), 6.80 (s, 1H), 5.66 (d, J=7.9 Hz, 1H), 4.69 (s, 1H), 4.51-4.34 (m, 3H), 4.23 (t, J=6.9 Hz, 1H), 3.14 (s, 2H), 2.40 (s, 3H), 2.11-1.72 (m, 3H), 1.60-1.48 (m, 3H), 1.44 (s, 9H).

$^{13}$C NMR (100 MHz, $CDCl_3$) δ 190.0, 170.1, 163.1, 156.1, 156.1, 143.7, 143.6, 141.2, 138.3, 132.9, 128.5, 128.1, 127.7, 127.0, 125.0, 119.9, 113.8, 79.2, 67.1, 54.0, 47.1, 39.7, 31.4, 29.6, 28.3, 22.4, 18.7 ppm.

HRMS m/z (ESI) calcd for $C_{36}H_{40}N_2NaO_7$ $(M+Na)^+$: 635.2728, found: 635.2722.

Preparation Example 23

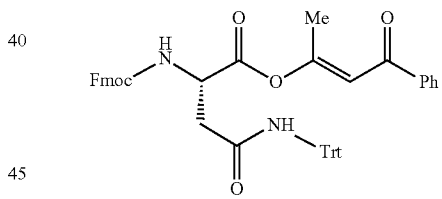

In a clean 4 mL reaction vial were added allenone (0.20 mmol) and 2 mL of 1,2-dichloroethane (DCE) followed by Fmoc-L-Asn(Trt)-OH (0.22 mmol); then the reaction was stirred at room temperature for 8 h, and the completion of the reaction was monitored by TLC; after the reaction, the pure product was obtained by column chromatography as a pale yellow oily liquid with a yield of 93%.

$^{1}$H NMR (400 MHz, $CDCl_3$) δ 7.82 (d, J=7.7 Hz, 2H), 7.73 (t, J=6.3 Hz, 2H), 7.61-7.56 (m, 2H), 7.51 (t, J=7.4 Hz, 1H), 7.42-7.34 (m, 4H), 7.31-7.07 (m, 17H), 6.81 (s, 1H), 6.62 (s, 1H), 6.15 (d, J=8.9 Hz, 1H), 4.82-4.70 (m, 1H), 4.51-4.39 (m, 1H), 4.39-4.28 (m, 1H), 4.22 (t, J=7.0 Hz, 1H), 3.19 (dd, J=16.3, 3.6 Hz, 1H), 2.91 (dd, J=16.3, 3.2 Hz, 1H), 2.24 (s, 3H).

$^{13}$C NMR (100 MHz, $CDCl_3$) δ 190.2, 169.1, 168.8, 163.6, 156.1, 144.1, 143.7, 143.5, 141.2, 138.3, 132.8, 128.5, 128.4, 128.2, 128.0, 127.7, 127.2, 127.0, 125.0, 119.9, 113.9, 71.0, 67.2, 50.8, 47.0, 38.7, 18.5 ppm.

HRMS m/z (ESI) calcd for $C_{48}H_{40}N_2NaO_6$ $(M+Na)^+$: 763.2779, found: 763.2763.

Preparation Example 24

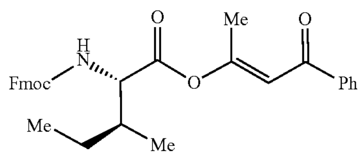

In a clean 4 mL reaction vial were added allenone (0.20 mmol) and 2 mL of 1,2-dichloroethane (DCE) followed by Fmoc-L-Ile-OH (0.22 mmol), then, the reaction was stirred at room temperature for 7 h, and the end of the reaction was monitored by TLC; after the reaction, the pure product was obtained by column chromatography as a light yellow oily liquid, and the yield was 99%.

$^1$H NMR (400 MHz, $CDCl_3$) δ 7.92 (d, J=7.0 Hz, 2H), 7.77 (d, J=7.5 Hz, 2H), 7.62 (d, J=7.4 Hz, 2H), 7.55 (t, J=7.4 Hz, 1H), 7.46 (t, J=7.6 Hz, 2H), 7.40 (t, J=7.6 Hz, 2H), 7.32 (t, J=7.4 Hz, 2H), 6.81 (s, 1H), 5.43 (d, J=9.0 Hz, 1H), 4.51 (dd, J=8.9, 5.1 Hz, 1H), 4.46 (d, J=7.0 Hz, 2H), 4.25 (t, J=6.9 Hz, 1H), 2.43 (s, 3H), 2.13-1.96 (m, 1H), 1.63-1.45 (m, 1H), 1.39-1.20 (m, 1H), 1.06 (d, J=6.8 Hz, 2H), 1.01 (t, J=7.4 Hz, 3H), 0.96-0.87 (m, 1H);

$^{13}$C NMR (100 MHz, $CDCl_3$) δ 190.0, 169.7, 163.0, 156.1, 143.7, 143.6, 141.2, 138.4, 132.9, 128.5, 128.1, 127.7, 127.0, 124.9, 119.9, 113.9, 67.0, 58.5, 47.1, 37.8, 25.1, 18.7, 15.6, 11.5 ppm.

HRMS m/z (ESI) calcd for $C_{31}H_{31}NNaO_5$ $(M+Na)^+$: 520.2100, found: 520.2128.

Preparation Example 25

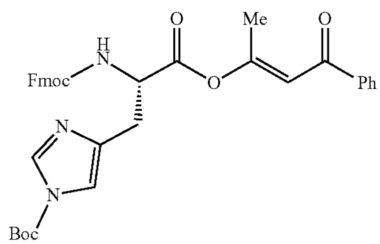

In a clean 4 mL reaction vial were added allenone (0.20 mmol) and 2 mL of 1,2-dichloroethane (DCE), followed by Fmoc-L-His(Boc)-OH (0.22 mmol); then the reaction was stirred at room temperature for 12 h, and the completion of the reaction was monitored by TLC; after the reaction, the pure product was obtained by column chromatography as a light yellow oily liquid with a yield of 24%.

$^1$H NMR (400 MHz, $CDCl_3$) δ 8.06 (s, 1H), 7.91 (d, J=7.5 Hz, 1H), 7.76 (d, J=7.5 Hz, 2H), 7.62 (t, J=7.4 Hz, 2H), 7.55 (t, J=7.3 Hz, 1H), 7.45 (t, J=7.6 Hz, 2H), 7.40 (t, J=7.5 Hz, 2H), 7.35-7.27 (m, 2H), 7.25 (s, 1H), 6.85 (s, 1H), 6.33 (d, J=8.1 Hz, 1H), 4.90-4.72 (m, 1H), 4.49-4.33 (m, 2H), 4.27 (t, J=7.3 Hz, 1H), 3.28 (dd, J=15.0, 5.3 Hz, 1H), 3.17 (dd, J=15.0, 4.8 Hz, 1H), 2.39 (s, 3H), 1.60 (s, 9H);

$^{13}$C NMR (100 MHz, $CDCl_3$) δ 190.1, 169.1, 163.4, 156.0, 146.7, 143.8, 143.7, 141.2, 138.5, 138.0, 137.1, 132.8, 128.5, 128.1, 127.7, 127.0, 125.1, 119.9, 114.9, 114.0, 85.9, 67.3, 53.7, 47.1, 29.7, 27.8, 18.7 ppm.

HRMS m/z (ESI) calcd for $C_{36}H_{35}N_3NaO_7$ $(M+Na)^+$: 644.2373, found: 644.2402.

Preparation Example 26

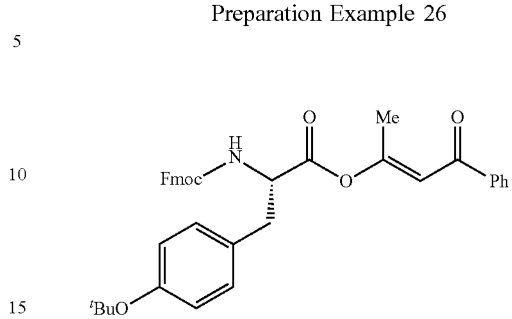

In a clean 4 mL reaction vial were added allenone (0.20 mmol) and 2 mL of 1,2-dichloroethane (DCE) followed by Fmoc-L-Tyr(tBu)-OH (0.22 mmol); then the reaction was stirred at room temperature for 12 h, and the completion of the reaction was monitored by TLC; after the reaction, the pure product was obtained by column chromatography as a pale yellow oily liquid with a yield of 85%.

$^1$H NMR (400 MHz, $CDCl_3$) δ 7.89 (d, J=7.7 Hz, 2H), 7.78 (d, J=7.5 Hz, 2H), 7.60 (d, J=7.5 Hz, 2H), 7.55 (d, J=7.4 Hz, 1H), 7.46 (t, J=7.6 Hz, 2H), 7.41 (t, J=7.6 Hz, 2H), 7.32 (t, J=7.4 Hz, 2H), 7.11 (d, J=8.0 Hz, 2H), 6.97 (d, J=7.9 Hz, 2H), 6.66 (s, 1H), 5.38 (s, 1H), 4.77 (dd, J=6.9 Hz, 2H), 4.57-4.36 (m, 2H), 4.24 (t, J=6.8 Hz, 1H), 3.17 (dd, J=6.4, 3.0 Hz, 2H), 2.34 (s, 3H), 1.34 (s, 9H).

$^{13}$C NMR (100 MHz, $CDCl_3$) δ 189.9, 169.3, 163.0, 155.5, 154.8, 143.7, 143.6, 141.3, 138.3, 132.9, 129.8, 128.6, 128.1, 127.7, 127.0, 125.0, 124.9, 124.2, 120.0, 113.8, 78.5, 67.0, 55.1, 47.1, 37.5, 28.8, 18.6 ppm.

HRMS m/z (ESI) calcd for $C_{38}H_{37}NNaO_6$ $(M+Na)^+$: 626.2513, found: 626.2505.

Preparation Example 27

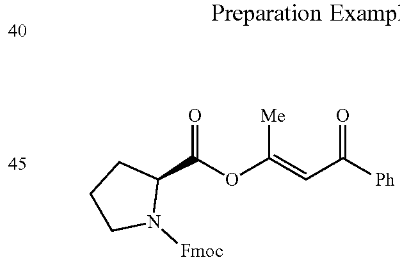

In a clean 4 mL reaction vial were added allenone (0.20 mmol) and 2 mL of 1,2-dichloroethane (DCE), followed by Fmoc-L-Pro-OH (0.22 mmol); then the reaction was stirred at room temperature for 8 h, and the completion of the reaction was monitored by TLC; after the reaction, the pure product was obtained by column chromatography as a light yellow oily liquid with a yield of 98%.

$^1$H NMR (400 MHz, $CDCl_3$) δ 7.92 (d, J=7.7 Hz, 1H), 7.76 (t, J=7.0 Hz, 3H), 7.66-7.58 (m, 2H), 7.56-7.48 (m, 1H), 7.45-7.29 (m, 6H), 6.89-6.63 (m, 1H), 4.54-4.37 (m, 3H), 4.31-4.21 (m, 1H), 3.74-3.66 (m, 2H), 3.58 (dd, J=10.3, 7.3 Hz, 2H), 2.47-2.31 (m, 4H), 2.19-2.10 (m, 1H), 2.08-1.93 (m, 2H).

$^{13}$C NMR (100 MHz, $CDCl_3$) δ 190.2, 189.9, 170.1, 170.0, 163.4, 163.1, 154.8, 154.2, 143.9, 143.9, 143.7, 143.5, 141.2, 141.2, 138.5, 138.3, 132.8, 132.8, 128.5, 128.1, 128.0, 127.7, 127.6, 127.1, 127.0, 127.0, 125.0, 125.0, 124.9, 119.9, 119.9, 113.6, 113.4, 67.6, 67.5, 59.4, 58.8, 47.3, 47.1, 47.0, 46.5, 31.0, 29.8, 24.5, 23.4, 18.7, 18.6 ppm.

HRMS m/z (ESI) calcd for $C_{30}H_{27}NNaO_5$ $(M+Na)^+$: 504.1781, found: 504.1771.

Preparation Example 28

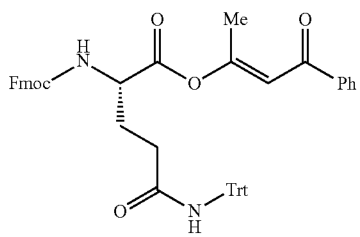

In a clean 4 mL reaction vial were added allenone (0.20 mmol) and 2 mL of 1,2-dichloroethane (DCE) followed by Fmoc-L-Gln(Trt)-OH (0.22 mmol); then the reaction was stirred at room temperature for 8 h, and the completion of the reaction was monitored by TLC; after the reaction, the pure product was obtained by column chromatography as a pale yellow oily liquid with a yield of 93%.

$^1$H NMR (400 MHz, $CDCl_3$) δ 7.84 (d, J=7.7 Hz, 2H), 7.70 (d, J=7.5 Hz, 2H), 7.57 (d, J=7.5 Hz, 2H), 7.50 (t, J=7.4 Hz, 1H), 7.45-7.31 (m, 4H), 7.30-7.14 (m, 17H), 6.85 (s, 1H), 6.75 (s, 1H), 5.70 (s, 1H), 4.52-4.45 (m, 1H), 4.44-4.36 (m, 2H), 4.21 (t, J=6.9 Hz, 1H), 2.46-2.19 (m, 6H), 2.14-1.92 (m, 1H);

$^{13}$C NMR (100 MHz, $CDCl_3$) δ 190.0, 170.6, 169.6, 163.1, 156.2, 144.4, 143.7, 143.5, 141.2, 141.2, 138.3, 132.8, 128.6, 128.5, 128.1, 127.9, 127.7, 127.0, 125.0, 119.9, 113.9, 70.7, 66.9, 53.7, 47.1, 32.8, 26.9, 18.6 ppm.

HRMS m/z (ESI) calcd for $C_{49}H_{42}N_2NaO_6$ $(M+Na)^+$: 777.2941, found: 777.2905.

Preparation Example 29

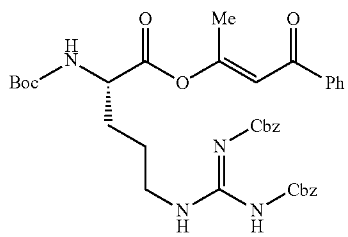 [SMILES: C/C(=C\C(=O)c1ccccc1)OC(=O)[C@H](CCCN/C(=N/C(=O)OCc1ccccc1)NC(=O)OCc1ccccc1)NC(=O)OC(C)(C)C]

In a clean 4 mL reaction vial were added allenone (0.20 mmol) and 2 mL of 1,2-dichloroethane (DCE), followed by Boc-L-Arg$(Cbz)_2$-OH (0.22 mmol); then the reaction was stirred at room temperature for 10 h, and the completion of the reaction was monitored by TLC; after the reaction, the pure product was obtained by column chromatography as a light yellow oily liquid with a yield of 95%.

$^1$H NMR (400 MHz, $CDCl_3$) δ 9.45 (s, 1H), 9.26 (s, 1H), 7.89 (d, J=8.4 Hz, 2H), 7.58-7.50 (m, 1H), 7.44 (t, J=7.8 Hz, 2H), 7.42-7.34 (m, 6H), 7.34-7.29 (m, 2H), 7.28-7.22 (m, 2H), 6.74 (s, 1H), 5.37 (d, J=8.3 Hz, 1H), 5.24 (s, 2H), 5.12 (s, 2H), 4.39 (s, 2H), 4.02 (s, 2H), 2.33 (s, 3H), 1.95-1.82 (m, 2H), 1.80-1.70 (m, 3H), 1.44 (s, 9H).

$^{13}$C NMR (100 MHz, $CDCl_3$) δ 190.0, 170.2, 163.7, 163.4, 160.4, 155.6, 155.4, 138.4, 136.7, 134.5, 132.8, 128.8, 128.8, 128.5, 128.3, 128.2, 128.1, 127.8, 127.7, 113.7, 80.0, 68.9, 66.9, 53.5, 44.0, 28.6, 28.2, 24.9, 18.6 ppm.

HRMS m/z (ESI) calcd for $C_{37}H_{43}N_4O_9$ $(M+H)^+$: 687.3025, found: 687.3030.

Preparation Example 30

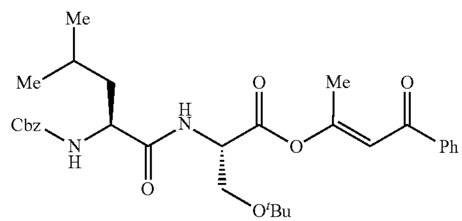 [SMILES: C/C(=C\C(=O)c1ccccc1)OC(=O)[C@H](COC(C)(C)C)NC(=O)[C@H](CC(C)C)NC(=O)OCc1ccccc1]

In a clean 4 mL reaction vial were added allenone (0.20 mmol) and 2 mL of 1,2-dichloroethane (DCE) followed by Cbz-L-Leu-L-Ser(tBu)-OH (0.22 mmol); then the reaction was stirred at room temperature for 10 h, and the completion of the reaction was monitored by TLC; after the reaction, the pure product was obtained by column chromatography as a pale yellow oily liquid with a yield of 99%.

$^1$H NMR (400 MHz, $CDCl_3$) δ 7.93-7.88 (m, 2H), 7.55 (t, J=7.4 Hz, 1H), 7.45 (t, J=7.7 Hz, 2H), 7.37-7.27 (m, 5H), 6.79-6.72 (m, 2H), 5.28 (d, J=9.2 Hz, 1H), 5.11 (s, 2H), 4.85 (dt, J=8.5, 3.0 Hz, 1H), 4.34-4.22 (m, 1H), 3.93 (dd, J=9.1, 3.0 Hz, 1H), 3.61 (dd, J=9.0, 3.0 Hz, 1H), 2.40 (s, 3H), 1.78-1.65 (m, 2H), 1.61-1.50 (m, 1H), 1.18 (s, 9H), 0.95 (d, J=6.1 Hz, 6H).

$^{13}$C NMR (100 MHz, $CDCl_3$) δ 190.1, 172.1, 167.9, 163.4, 156.0, 138.5, 136.2, 132.9, 128.6, 128.5, 128.1, 128.1, 128.0, 113.8, 73.7, 67.0, 61.9, 53.4, 52.9, 41.6, 27.3, 24.6, 22.8, 22.0, 18.7 ppm.

HRMS m/z (ESI) calcd for $C_{31}H_{41}N_2O_7$ $(M+H)^+$: 553.2908, found: 553.2902.

Preparation Example 31

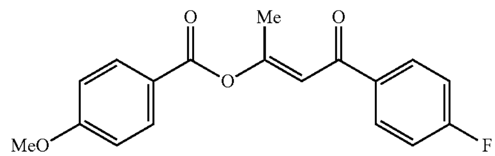 [SMILES: COc1ccc(C(=O)O/C(C)=C/C(=O)c2ccc(F)cc2)cc1]

In a clean 4 mL reaction vial were added allenone (0.20 mmol) and 2 mL of 1,2-dichloroethane (DCE) followed by 4-methoxybenzoic acid (0.22 mmol); then the reaction was stirred at room temperature for 15 h, TLC was used to monitor the end of the reaction; after the end of the reaction, the pure product was obtained by column chromatography as a colorless oily liquid with a yield of 94%.

$^1$H NMR (400 MHz, $CDCl_3$) δ 8.07 (d, J=8.9 Hz, 2H), 7.98 (dd, J=8.7, 5.6 Hz, 2H), 7.13 (t, J=8.6 Hz, 2H), 6.98 (d, J=8.9 Hz, 2H), 6.90 (s, 1H), 3.89 (s, 3H), 2.51 (s, 3H).

$^{13}$C NMR (100 MHz, $CDCl_3$) δ 188.8, 166.9, 164.5, 164.3, 164.2, 163.7, 135.2, 135.1, 132.3, 130.8, 130.7, 121.4, 115.8, 115.5, 114.0, 113.3, 55.5, 19.2 ppm.

HRMS m/z (ESI) calcd for $C_{18}H_{16}FO_4$ $(M+H)^+$: 315.1027, found: 315.1021.

Preparation Example 32

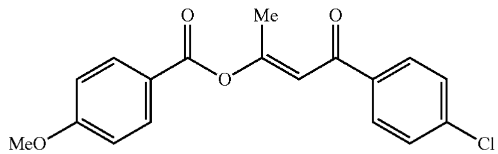 [SMILES: COc1ccc(C(=O)O/C(C)=C/C(=O)c2ccc(Cl)cc2)cc1]

In a clean 4 mL reaction vial were added allenone (0.20 mmol) and 2 mL of 1,2-dichloroethane (DCE) followed by 4-methoxybenzoic acid (0.22 mmol); then the reaction was stirred at room temperature for 11 h, TLC was used to monitor the end of the reaction; after the end of the reaction, the pure product was obtained by column chromatography as a colorless oily liquid with a yield of 78%.

$^1H$ NMR (400 MHz, $CDCl_3$) δ 8.06 (d, J=8.9 Hz, 2H), 7.89 (d, J=8.6 Hz, 2H), 7.43 (d, J=8.6 Hz, 2H), 6.97 (d, J=9.0 Hz, 2H), 6.89 (s, 1H), 3.89 (s, 3H), 2.52 (s, 3H).

$^{13}C$ NMR (10 MHz, $CDCl_3$) δ 189.1, 164.9, 164.2, 163.7, 139.2, 137.1, 132.3, 129.6, 128.9, 121.3, 114.0, 113.1, 55.5, 19.3 ppm.

HRMS m/z (ESI) calcd for $C_{18}H_{16}ClO_4$ $(M+H)^+$: 331.0732.

Preparation Example 33

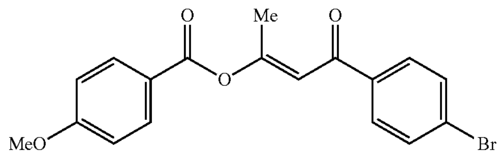 [SMILES: COc1ccc(C(=O)O/C(C)=C/C(=O)c2ccc(Br)cc2)cc1]

In a clean 4 mL reaction vial were added allenone (0.20 mmol) and 2 mL of 1,2-dichloroethane (DCE) followed by 4-methoxybenzoic acid (0.22 mmol); then the reaction was stirred at room temperature for 12 h, TLC was used to monitor the end of the reaction; after the reaction, the pure product was obtained by column chromatography as a colorless oily liquid with a yield of 78%.

$^1H$ NMR (400 MHz, $CDCl_3$) δ 8.06 (d, J=8.9 Hz, 2H), 7.81 (d, J=8.5 Hz, 2H), 7.60 (d, J=8.5 Hz, 2H), 6.97 (d, J=8.9 Hz, 2H), 6.88 (s, 1H), 3.89 (s, 3H), 2.51 (s, 3H).

$^{13}C$ NMR (100 MHz, $CDCl_3$) δ 189.2, 165.0, 164.2, 163.7, 137.5, 132.3, 131.9, 129.7, 127.9, 121.3, 114.0, 113.1, 55.6, 19.3 ppm.

HRMS m/z (ESI) calcd for $C_{18}H_{16}BrO_4$ $(M+H)^+$: 375.0226, found: 375.0221.

Preparation Example 34

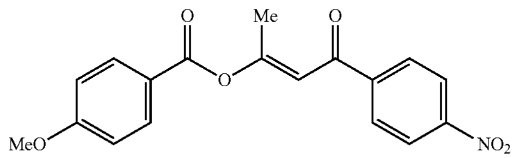 [SMILES: COc1ccc(C(=O)O/C(C)=C/C(=O)c2ccc([N+](=O)[O-])cc2)cc1]

In a clean 4 mL reaction vial were added allenone (0.20 mmol) and 2 mL of 1,2-dichloroethane (DCE) followed by 4-methoxybenzoic acid (0.22 mmol); then the reaction was stirred at room temperature for 96 h, the TLC was used to monitor the end of the reaction; after the reaction, the pure product was obtained by column chromatography as an orange oily liquid with a yield of 59%.

$^1H$ NMR (400 MHz, $CDCl_3$) δ 8.31 (d, J=8.7 Hz, 2H), 8.08 (t, J=8.5 Hz, 2H), 7.13-6.81 (m, 3H), 3.90 (s, 3H), 2.56 (s, 3H).

$^{13}C$ NMR (101 MHz, $CDCl_3$) δ 188.6, 166.6, 164.4, 163.5, 150.1, 143.5, 132.4, 129.1, 123.8, 121.1, 114.1, 112.7, 55.6, 19.6 ppm.

HRMS m/z (ESI) calcd for $C_{18}H_{15}NNaO_6$ $(M+Na)^+$: 364.0792, found: 361.0789.

Preparation Example 35

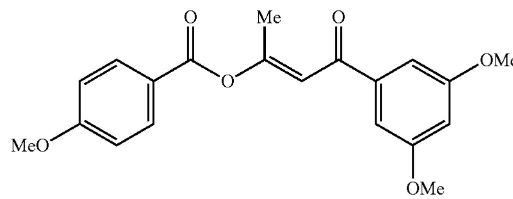 [SMILES: COc1ccc(C(=O)O/C(C)=C/C(=O)c2cc(OC)cc(OC)c2)cc1]

In a clean 4 mL reaction vial were added allenone (0.20 mmol) and 2 mL of 1,2-dichloroethane (DCE) followed by 4-methoxybenzoic acid (0.22 mmol); then the reaction was stirred at room temperature for 36 h, TLC was used to monitor the end of the reaction; after the end of the reaction, the pure product was obtained by column chromatography as a colorless oily liquid with a yield of 79%.

$^1H$ NMR (400 MHz, $CDCl_3$) δ 8.06 (d, J=8.9 Hz, 2H), 7.09 (d, J=2.3 Hz, 2H), 6.97 (d, J=8.9 Hz, 2H), 6.85 (s, 0H), 6.64 (t, J=2.3 Hz, 0H), 3.89 (s, 3H), 3.84 (s, 6H), 2.51 (s, 3H).

$^{13}C$ NMR (100 MHz, $CDCl_3$) δ 190.0, 164.5, 164.1, 163.7, 160.9, 140.8, 132.3, 121.4, 113.9, 113.7, 106.0, 105.3, 55.6, 55.5, 19.2 ppm.

HRMS m/z (ESI) calcd for $C_{20}H_{20}NaO_6$ $(M+Na)^+$: 379.1152, found: 379.1149.

Preparation Example 36

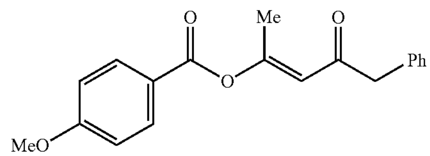 [SMILES: COc1ccc(C(=O)O/C(C)=C/C(=O)Cc2ccccc2)cc1]

In a clean 4 mL reaction vial were added allenone (0.20 mmol) and 2 mL of 1,2-dichloroethane (DCE) followed by 4-methoxybenzoic acid (0.22 mmol); then the reaction was stirred at room temperature for 168 h, and the reaction was monitored by TLC; after the reaction, the pure product was obtained by column chromatography as a colorless oily liquid with a yield of 88%.

$^1H$ NMR (400 MHz, $CDCl_3$) δ 7.99 (d, J=8.9 Hz, 2H), 7.33 (t, J=7.3 Hz, 2H), 7.29-7.25 (m, 1H), 7.24-7.19 (m, 2H), 6.94 (d, J=8.9 Hz, 2H), 6.24 (s, 1H), 3.87 (s, 3H), 3.76 (s, 2H), 2.43 (s, 3H).

$^{13}C$ NMR (100 MHz, $CDCl_3$) δ 197.0, 164.2, 164.1, 163.6, 134.3, 132.3, 129.6, 128.7, 127.0, 121.3, 115.3, 113.9, 55.5, 51.7, 19.0 ppm.

HRMS m/z (ESI) calcd for $C_{19}H_{18}NaO_4$ $(M+Na)^+$: 333.1097, found: 333.1095.

Application Example A

The amide having the general formula (IV) was prepared by using the α-carbonyl alkenyl ester in the general formula (I) as an intermediate.

Example A1

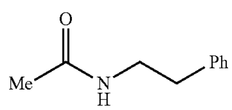 [SMILES: CC(=O)NCCc1ccccc1]

In a clean 4 mL reaction vial were added α-carbonyl alkenyl ester (from Preparative Example 1) (0.20 mmol) and 1.5 mL N,N-dimethylformamide, followed by phenethylamine (0.22 mmol); then the reaction was stirred at room temperature for 5 min, and the completion of the reaction was monitored by TLC; after the reaction was completed, the pure product was obtained as a white solid by column chromatography, and the yield was 93%.

$^{1}H$ NMR (400 MHz, $CDCl_3$) δ 7.27 (t, J=7.3 Hz, 2H), 7.21-7.16 (m, 3H), 6.50 (s, 1H), 3.45 (dd, J=13.3, 7.0 Hz, 2H), 2.79 (t, J=7.2 Hz, 2H), 1.90 (s, 3H).

$^{13}C$ NMR (100 MHz, $CDCl_3$) δ 170.2, 138.7, 128.4, 128.3, 126.1, 40.5, 35.3, 22.8 ppm.

HRMS m/z (ESI) calcd for $C_{10}H_{14}NO$ $(M+H)^+$: 164.1075, found 164.1070.

Example A2

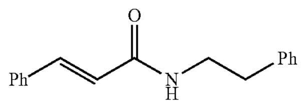 [SMILES: O=C(/C=C/c1ccccc1)NCCc1ccccc1]

To a clean 4 mL reaction vial were added α-carbonyl alkenyl ester (from Preparative Example 7) (0.20 mmol) and 1.5 mL of N,N-dimethylformamide, followed by phenethylamine (0.22 mmol); then the reaction was stirred at room temperature for 5 min, and the completion of the reaction was monitored by TLC; after the completion of the reaction, the pure product was obtained as a white solid by column chromatography, and the yield was 94%.

$^{1}H$ NMR (400 MHz, $CDCl_3$) δ 7.62 (d, J=15.6 Hz, 1H), 7.47 (dd, J=6.5, 2.9 Hz, 2H), 7.37-7.29 (m, 5H), 7.28-7.20 (m, 3H), 6.35 (d, J=15.6 Hz, 1H), 5.85 (s, 1H), 3.66 (dd, J=13.0, 6.8 Hz, 2H), 2.89 (t, J=6.9 Hz, 2H).

$^{13}C$ NMR (100 MHz, $CDCl_3$) δ 165.9, 141.0, 138.9, 134.8, 129.6, 128.8, 128.7, 128.6, 127.7, 126.5, 120.7, 40.8, 35.6 ppm.

HRMS m/z (ESI) calcd for $C_{17}H_{18}NO$ $(M+H)^+$: 252.1388, found: 252.1385.

Example A3

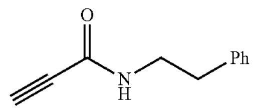

In a clean 4 mL reaction vial were added α-carbonyl alkenyl ester (from Preparative Example 8) (0.20 mmol) and N,N-dimethylformamide 1.5 mL, followed by phenethylamine (0.22 mmol); then the reaction was stirred at room temperature for 5 min, and the completion of the reaction was monitored by TLC; after the reaction, the pure product was obtained as a white solid by column chromatography, and the yield was 99%.

$^{1}H$ NMR (400 MHz, $CDCl_3$) δ 7.33 (t, J=7.3 Hz, 2H), 7.27-7.18 (m, 3H), 5.94 (s, 1H), 3.57 (q, J=6.9 Hz, 2H), 2.85 (t, J=7.0 Hz, 2H), 2.75 (s, 1H).

$^{13}C$ NMR (100 MHz, $CDCl_3$) δ 152.1, 138.2, 128.7, 128.7, 126.7, 79.2, 73.1, 40.9, 35.2 ppm.

HRMS m/z (ESI) calcd for $CH_{11}H_{12}NO$ $(M+H)^+$: 174.0919, found: 174.0916.

Example A4

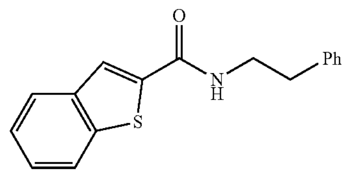 [SMILES: O=C(NCCc1ccccc1)c1cc2ccccc2s1]

To a clean 4 mL reaction vial were added α-carbonyl alkenyl ester (from Preparative Example 6) (0.20 mmol) and 1.5 mL of N,N-dimethylformamide, followed by phenethylamine (0.22 mmol); then the reaction was stirred at room temperature for 5 min, and the completion of the reaction was monitored by TLC; after the completion of the reaction, the pure product was obtained as a white solid by column chromatography, and the yield was 84%.

$^{1}H$ NMR (400 MHz, $CDCl_3$) δ 7.90-7.75 (m, 2H), 7.68 (s, 1H), 7.42-7.36 (m, 2H), 7.34-7.30 (m, 2H), 7.26-7.24 (m, 3H), 6.26 (s, 1H), 3.71 (dd, J=13.0, 6.8 Hz, 2H), 2.94 (t, J=6.9 Hz, 2H).

$^{13}C$ NMR (100 MHz, $CDCl_3$) δ 162.2, 140.7, 139.0, 138.7, 138.4, 128.8, 128.7, 126.6, 126.3, 125.1, 125.0, 124.9, 122.7, 41.3, 35.7 ppm.

HRMS m/z (ESI) calcd for $C_{17}H_{16}NOS$ $(M+H)^+$: 282.0953, found: 282.0950.

Example A5

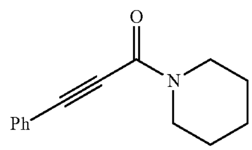 [SMILES: O=C(C#Cc1ccccc1)N1CCCCC1]

In a clean 4 mL reaction vial were added α-carbonyl alkenyl ester (from Preparative Example 9) (0.20 mmol) and 1.5 mL of N,N-dimethylformamide, followed by piperidine (0.22 mmol); then the reaction was stirred at room temperature for 5 min, and the completion of the reaction was monitored by TLC; after the reaction, the pure product was obtained by column chromatography as a white solid with a yield of 98%.

$^1$H NMR (400 MHz, $CDCl_3$) δ 7.59-7.45 (m, 2H), 7.43-7.28 (m, 3H), 3.79-3.72 (m, 2H), 3.64-3.56 (m, 2H), 1.65 (dt, J=9.9, 6.3 Hz, 4H), 1.56 (dt, J=11.0, 5.6 Hz, 2H).

$^{13}$C NMR (100 MHz, $CDCl_3$) δ 152.8, 132.2, 129.7, 128.4, 120.7, 90.1, 81.4, 48.1, 42.3, 26.4, 25.3, 24.4 ppm.

HRMS m/z (ESI) calcd for $C_{14}H_{16}NO$ $(M+H)^+$: 214.1226, found: 214.1217.

Example A6

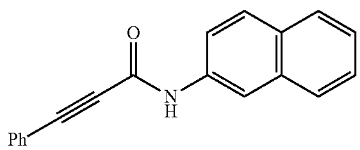 [SMILES: O=C(C#Cc1ccccc1)Nc1ccc2ccccc2c1]

In a clean 4 mL reaction vial were added α-carbonyl alkenyl ester (from Preparation Example 9) (0.20 mmol) and 1.5 mL of N,N-dimethylformamide, followed by 2-naphthylamine (0.22 mmol); then the reaction was stirred at room temperature for 12 h, and the completion of the reaction was monitored by TLC; after the reaction was completed, the pure product was obtained as a white solid by column chromatography, and the yield was 99%.

$^1$H NMR (400 MHz, $CDCl_3$) δ 8.26 (s, 1H), 7.92 (s, 1H), 7.79 (t, J=7.8 Hz, 3H), 7.57 (d, J=6.9 Hz, 2H), 7.55-7.38 (m, 4H), 7.36 (t, J=7.4 Hz, 2H).

$^{13}$C NMR (100 MHz, $CDCl_3$) δ 151.1, 134.8, 133.8, 132.7, 130.9, 130.4, 129.0, 128.6, 127.8, 127.6, 126.7, 125.4, 119.9, 119.5, 117.1, 85.9, 83.5 ppm.

HRMS m/z (ESI) calcd for $C_{19}H_{14}NO$ $(M+H)^+$: 272.1070, found: 272.1110.

Example A7

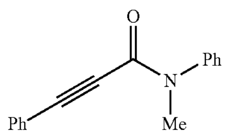 [SMILES: CN(C(=O)C#Cc1ccccc1)c1ccccc1]

In a clean 4 mL reaction vial were added α-carbonyl alkenyl ester (from Preparative Example 9) (0.20 mmol) and 1.5 mL of N,N-dimethylformamide, followed by N-methylaniline (0.22 mmol); then, the reaction was stirred at room temperature for 24 h, and TLC was used to monitor the completion of the reaction; after the reaction was completed, the pure product was obtained as a white solid by column chromatography, and the yield was 99%.

$^1$H NMR (400 MHz, $CDCl_3$) δ 7.50-7.29 (m, 6H), 7.29-7.19 (m, 2H), 7.14 (d, J=6.8 Hz, 2H), 3.40 (s, 3H).

$^{13}$C NMR (100 MHz, $CDCl_3$) δ 154.3, 143.3, 132.4, 129.9, 129.2, 128.3, 127.9, 127.4, 120.5, 90.9, 82.6, 36.4 ppm.

HRMS m/z (ESI) calcd for $C_{16}H_{14}NO$ $(M+H)^+$: 236.1070, found 236.1085.

Example A8

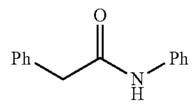 [SMILES: O=C(Cc1ccccc1)Nc1ccccc1]

In a clean 4 mL reaction vial were added α-carbonyl alkenyl ester (from Preparative Example 10) (0.20 mmol) and N,N-dimethylformamide 1.5 mL, followed by aniline (0.22 mmol); then the reaction was stirred at room temperature for 24 h, and the completion of the reaction was monitored by TLC; after the completion of the reaction, the pure product was obtained as a white solid by column chromatography, and the yield was 76%.

$^1$H NMR (400 MHz, $CDCl_3$) δ 7.40 (t, J=8.5 Hz, 3H), 7.36-7.31 (m, 3H), 7.32-7.23 (m, 2H), 7.17 (s, 1H), 7.08 (t, J=7.4 Hz, 1H), 3.73 (s, 2H).

$^{13}$C NMR (100 MHz, $CDCl_3$) δ 169.1, 137.6, 134.5, 129.5, 129.2, 128.9, 127.7, 124.5, 119.8, 44.9 ppm.

HRMS m/z (ESI) calcd for $C_{14}H_{14}NO$ $(M+H)^+$: 212.1070, found 212.1058.

Example A9

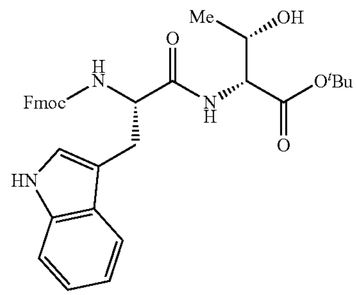

In a clean 4 mL reaction vial were added α-carbonyl alkenyl ester (from Preparative Example 13) (0.20 mmol) and 1.5 mL of N,N-dimethylformamide, followed by H-L-Thr-OtBu (0.22 mmol); then the reaction was stirred at room temperature for 5 min, and the completion of the reaction was monitored by TLC; after the reaction was completed, the pure product was obtained as a white solid by column chromatography, and the yield was 95%.

$^1$H NMR (400 MHz, $CDCl_3$) δ 8.20 (s, 1H), 7.74 (d, J=7.5 Hz, 2H), 7.65 (d, J=7.7 Hz, 1H), 7.52-7.47 (m, 2H), 7.38 (t, J=7.4 Hz, 2H), 7.31-7.24 (m, 3H), 7.16 (t, J=7.4 Hz, 1H), 7.10 (t, J=7.4 Hz, 1H), 7.03 (s, 1H), 6.84 (d, J=8.5 Hz, 1H), 5.69 (d, J=7.8 Hz, 1H), 4.61 (d, J=5.8 Hz, 1H), 4.42 (dd, J=8.6, 3.1 Hz, 1H), 4.39-4.25 (m, 2H), 4.21-4.09 (m, 2H), 3.27 (d, J=5.5 Hz, 2H), 2.69 (s, 1H), 1.43 (s, 9H), 1.08 (d, J=5.4 Hz, 3H).

$^{13}$C NMR (100 MHz, $CDCl_3$) δ 172.0, 169.5, 156.2, 143.8, 143.7, 141.2, 136.2, 127.7, 127.1, 125.1, 123.4, 122.2, 119.9, 119.7, 118.6, 111.3, 110.2, 82.5, 68.4, 67.2, 58.2, 55.7, 47.0, 28.3, 27.9, 19.9 ppm.

HRMS m/z (ESI) calcd for $C_{34}H_{37}N_3NaO_6$ $(M+Na)^+$: 606.2575, found: 606.2576.

Example A10

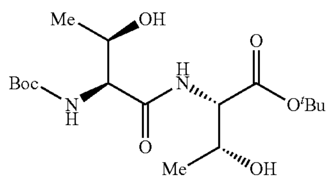 [SMILES: C[C@@H](O)[C@H](NC(=O)OC(C)(C)C)C(=O)N[C@H](C(=O)OC(C)(C)C)[C@@H](C)O]

In a clean 4 mL reaction vial were added α-carbonyl alkenyl ester (from Preparative Example 14) (0.20 mmol) and 1.5 mL of N,N-dimethylformamide, followed by H-L-Thr-OtBu (0.22 mmol); then the reaction was stirred at room temperature for 15 min, and the reaction was monitored by TLC; after the reaction, the pure product was obtained as a white solid by column chromatography with a yield of 93%.

$^1$H NMR (400 MHz, $CDCl_3$) δ 7.35 (d, J=7.7 Hz, 1H), 5.73 (s, 1H), 4.42 (dd, J=8.7, 2.4 Hz, 1H), 4.35-4.09 (m, 3H), 1.43 (d, J=10.9 Hz, 18H), 1.18 (t, J=6.2 Hz, 6H).

$^{13}$C NMR (100 MHz, $CDCl_3$) δ 171.7, 169.8, 156.2, 82.6, 80.3, 68.2, 67.3, 58.7, 58.4, 28.2, 27.9, 20.0, 18.2 ppm.

HRMS m/z (ESI) calcd for $C_{17}H_{32}N_2NaO_7$ $(M+Na)^+$: 399.2102, found: 399.2094.

Example A11

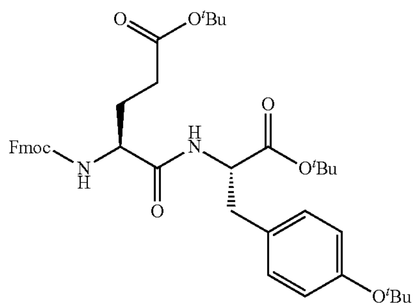

In a clean 4 mL reaction vial were added α-carbonyl alkenyl ester (from Preparative Example 18) (0.20 mmol) and 1.5 mL of N,N-dimethylformamide, followed by H-L-Tyr(tBu)-OtBu (0.22 mmol); then the reaction was stirred at room temperature for 5 min, and the completion of the reaction was monitored by TLC; after the reaction, the pure product was obtained by column chromatography as a white solid with a yield of 97%.

$^1$H NMR (400 MHz, $CDCl_3$) δ 7.75 (d, J=7.5 Hz, 2H), 7.60 (d, J=7.5 Hz, 2H), 7.39 (t, J=7.5 Hz, 2H), 7.30 (t, J=7.3 Hz, 2H), 7.06 (d, J=8.1 Hz, 2H), 6.94-6.77 (m, 3H), 5.79 (d, J=7.9 Hz, 1H), 4.78-4.61 (m, 1H), 4.43-4.32 (m, 2H), 4.28-4.17 (m, 2H), 3.04 (d, J=6.3 Hz, 2H), 2.48-2.28 (m, 2H), 2.14-2.00 (m, 2H), 1.98-1.80 (m, 1H), 1.45 (s, 9H), 1.37 (s, 9H), 1.29 (s, 9H).

$^{13}$C NMR (100 MHz, $CDCl_3$) δ 172.7, 170.7, 170.1, 156.1, 154.3, 143.8, 143.7, 141.2, 130.8, 129.8, 127.6, 127.0, 125.1, 124.0, 119.9, 82.2, 80.9, 78.2, 67.1, 54.1, 53.9, 47.1, 37.4, 31.6, 28.7, 28.3, 28.0, 27.8 ppm.

HRMS m/z (ESI) calcd for $C_{41}H_{53}N_2O_8$ $(M+H)^+$: 701.3796, found: 701.3801.

Example A12

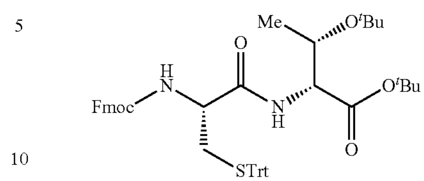

In a clean 4 mL reaction vial were added α-carbonyl alkenyl ester (from Preparative Example 19) (0.20 mmol) and 1.5 mL of N,N-dimethylformamide, followed by H-L-Thr(tBu)-OtBu (0.22 mmol); then the reaction was stirred at room temperature for 5 min, and the completion of the reaction was monitored by TLC; after the reaction, the pure product was obtained by column chromatography as a white solid with a yield of 95%.

$^1$H NMR (400 MHz, $CDCl_3$) δ 7.76 (t, J=7.0 Hz, 2H), 7.59 (d, J=7.5 Hz, 2H), 7.47 (d, J=7.4 Hz, 6H), 7.45-7.36 (m, 2H), 7.34-7.27 (m, 8H), 7.22 (t, J=7.2 Hz, 3H), 6.56 (d, J=8.8 Hz, 1H), 5.20 (d, J=8.1 Hz, 1H), 4.41-4.33 (m, 2H), 4.29 (d, J=8.6 Hz, 1H), 4.25-4.14 (m, 2H), 3.82-3.71 (m, 1H), 2.79 (dd, J=13.3, 7.9 Hz, 1H), 2.67 (dd, J=13.3, 5.4 Hz, 1H), 1.89 (s, 1H), 1.43 (s, 9H), 1.15 (s, 9H), 1.11 (d, J=6.3 Hz, 3H).

$^{13}$C NMR (100 MHz, $CDCl_3$) δ 170.2, 169.2, 155.6, 144.3, 143.8, 143.7, 141.2, 129.6, 128.0, 127.6, 127.0, 126.8, 125.1, 119.9, 81.8, 73.8, 67.2, 67.1, 67.0, 58.5, 53.8, 47.0, 34.2, 28.6, 28.0, 20.6 ppm.

HRMS m/z (ESI) calcd for $C_{49}H_{54}N_2NaO_6S$ $(M+Na)^+$: 821.3595, found: 821.3618.

Example A13

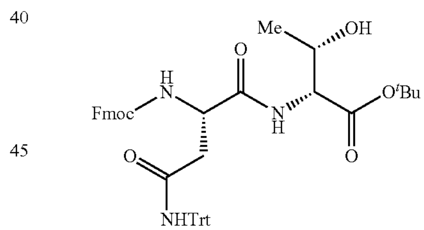

In a clean 4 mL reaction vial were added α-carbonyl alkenyl ester (from Preparative Example 23) (0.20 mmol) and 1.5 mL of N,N-dimethylformamide, followed by H-L-Thr-OtBu (0.22 mmol); then the reaction was stirred at room temperature for 5 min, and the completion of the reaction was monitored by TLC; after the reaction, the pure product was obtained by column chromatography as a white solid with a yield of 90%.

$^1$H NMR (400 MHz, $CDCl_3$) δ 7.85-7.74 (m, 2H), 7.60 (d, J=7.5 Hz, 2H), 7.43 (t, J=7.5 Hz, 2H), 7.38-7.27 (m, 10H), 7.25-7.17 (m, 6H), 7.10 (s, 1H), 6.54 (d, J=8.3 Hz, 1H), 4.65 (s, 1H), 4.47-4.32 (m, 3H), 4.23 (t, J=7.1 Hz, 2H), 3.14 (dd, J=15.8, 4.5 Hz, 1H), 2.73 (dd, J=15.8, 5.2 Hz, 1H), 2.65 (s, 1H), 2.12-1.97 (m, 1H), 1.49 (s, 9H), 1.14 (d, J=6.4 Hz, 3H).

$^{13}$C NMR (100 MHz, $CDCl_3$) δ 171.3, 170.2, 169.3, 156.3, 144.2, 143.7, 143.6, 141.2, 128.6, 127.9, 127.6, 127.0, 125.1, 125.1, 119.9, 82.4, 70.8, 68.3, 67.3, 58.4, 51.7, 47.0, 38.2, 27.9, 20.0 ppm.

HRMS m/z (ESI) calcd for $C_{46}H_{48}N_3O_7$ $(M+H)^+$: 754.3487, found: 754.3484.

Example A14

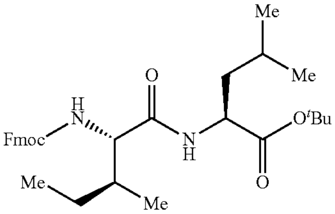

In a clean 4 mL reaction vial were added α-carbonyl alkenyl ester (from Preparative Example 24) (0.20 mmol) and 1.5 mL of N,N-dimethylformamide, followed by H-L-Leu-OtBu (0.22 mmol); then the reaction was stirred at room temperature for 5 min, and the completion of the reaction was monitored by TLC; after the reaction, the pure product was obtained by column chromatography as a white solid with a yield of 90%.

$^1H$ NMR (400 MHz, $CDCl_3$) δ 7.75 (d, J=7.6 Hz, 2H), 7.59 (d, J=7.6 Hz, 2H), 7.39 (t, J=7.5 Hz, 2H), 7.30 (t, J=7.5 Hz, 2H), 6.31 (s, 1H), 5.53 (s, 1H), 4.55-4.30 (m, 3H), 4.21 (t, J=7.1 Hz, 1H), 4.07 (t, J=8.2 Hz, 1H), 1.69-1.54 (m, 3H), 1.53-1.34 (m, 11H), 1.02-0.82 (m, 13H).

$^{13}C$ NMR (100 MHz, $CDCl_3$) δ 171.6, 170.8, 156.2, 143.8, 143.7, 141.2, 127.6, 127.0, 125.0, 119.9, 119.9, 81.9, 67.0, 59.5, 51.5, 47.1, 41.7, 37.7, 27.9, 24.8, 22.6, 22.1, 15.3, 11.3 ppm.

HRMS m/z (ESI) calcd for $C_{31}H_{43}N_2O_5$ $(M+H)^+$: 523.3166, found: 523.3160.

Example A15

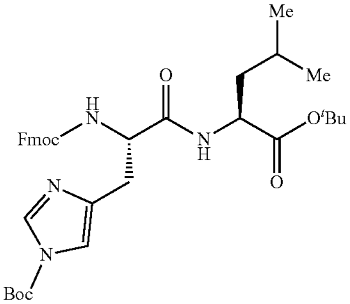

In a clean 4 mL reaction vial were added α-carbonyl alkenyl ester (from Preparative Example 25) (0.20 mmol) and 1.5 mL of N,N-dimethylformamide, followed by H-L-Leu-OtBu (0.22 mmol); then the reaction was stirred at room temperature for 5 min, and TLC was used to monitor the end of the reaction; after the reaction, the pure product was obtained as a white solid by column chromatography, and the yield was 85%.

$^1H$ NMR (400 MHz, $CDCl_3$) δ 8.03 (s, 1H), 7.75 (d, J=7.6 Hz, 2H), 7.61 (s, 2H), 7.38 (t, J=7.5 Hz, 2H), 7.30 (t, J=7.4 Hz, 2H), 7.20 (s, 2H), 6.71 (d, J=7.5 Hz, 1H), 4.58 (q, J=6.0 Hz, 1H), 4.46-4.32 (m, 3H), 4.24 (t, J=7.4 Hz, 1H), 3.17 (dd, J=14.8, 4.9 Hz, 1H), 2.97 (dd, J=14.9, 5.8 Hz, 1H), 1.58 (s, 9H), 1.54-1.49 (m, 1H), 1.41 (s, 11H), 0.91-0.74 (m, 6H).

$^{13}C$ NMR (100 MHz, $CDCl_3$) δ 171.4, 170.4, 156.1, 146.7, 143.8, 141.1, 139.1, 136.6, 127.6, 127.0, 125.1, 119.8, 114.8, 85.6, 81.6, 67.2, 54.6, 51.3, 47.0, 41.4, 30.2, 27.8, 27.7, 24.6, 22.7, 21.7 ppm.

HRMS m/z (ESI) calcd for $C_{36}H_{47}N_4O_7$ $(M+H)^+$: 647.3439, found: 647.3444.

Example A16

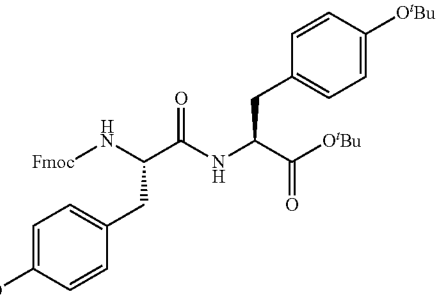

In a clean 4 mL reaction vial were added α-carbonyl alkenyl ester (from Preparative Example 26) (0.20 mmol) and 1.5 mL of N,N-dimethylformamide, followed by H-L-Tyr(tBu)-OtBu (0.22 mmol); then the reaction was stirred at room temperature for 5 min, and the completion of the reaction was monitored by TLC; after the reaction, the pure product was obtained by column chromatography as a white solid with a yield of 99%.

$^1H$ NMR (400 MHz, $CDCl_3$) δ 7.76 (d, J=7.5 Hz, 0H), 7.60-7.53 (m, 0H), 7.39 (t, J=7.3 Hz, 0H), 7.31 (t, J=7.6 Hz, 0H), 7.08 (d, J=8.0 Hz, 0H), 6.97 (d, J=8.1 Hz, 0H), 6.88 (dd, J=15.1, 8.4 Hz, 0H), 6.44 (s, 0H), 5.43 (s, 0H), 4.64 (q, J=6.5 Hz, 0H), 4.48-4.37 (m, 0H), 4.30 (t, J=8.9 Hz, 0H), 4.19 (t, J=6.9 Hz, 0H), 3.08-2.94 (m, 0H), 1.35 (s, 1H), 1.30 (s, 1H), 1.29 (s, 1H).

$^{13}C$ NMR (100 MHz, $CDCl_3$) δ 170.1, 170.0, 155.8, 154.4, 154.2, 143.7, 143.7, 141.2, 130.8, 130.7, 129.8, 129.8, 127.6, 127.0, 125.0, 124.1, 124.0, 119.9, 82.3, 78.2, 67.1, 56.0, 53.8, 47.0, 37.7, 37.5, 28.8, 28.7, 27.8 ppm.

HRMS m/z (ESI) calcd for $C_{45}H_{55}N_2O_7$ $(M+H)^+$: 735.4004, found: 735.4000.

Example A17

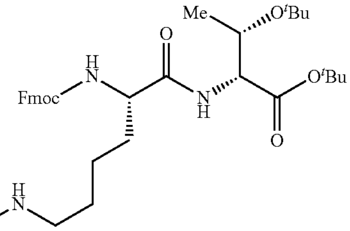

In a clean 4 mL reaction vial were added α-carbonyl alkenyl ester (from Preparative Example 22) (0.20 mmol) and 1.5 mL of N,N-dimethylformamide (DMF), followed by H-L-Thr(tBu)-OtBu (0.22 mmol); then the reaction was stirred at room temperature for 30 min, and the completion of the reaction was monitored by TLC; after the reaction, the pure product was obtained by column chromatography as a white solid with a yield of 90%.

$^1$H NMR (400 MHz, $CDCl_3$) δ 7.75 (d, J=7.5 Hz, 2H), 7.59 (d, J=7.5 Hz, 2H), 7.39 (t, J=7.5 Hz, 2H), 7.30 (t, J=7.4 Hz, 2H), 6.47 (d, J=8.9 Hz, 1H), 5.61 (d, J=8.1 Hz, 1H), 4.77 (s, 1H), 4.37 (d, J=7.2 Hz, 2H), 4.33 (dd, J=9.0, 2.0 Hz, 1H), 4.27 (q, J=7.3 Hz, 1H), 4.24-4.18 (m, 2H), 3.12 (s, 2H), 2.03 (s, 1H), 1.92-1.84 (m, 1H), 1.76-1.65 (m, 1H), 1.57-1.47 (m, 3H), 1.45 (s, 9H), 1.42 (s, 9H), 1.36-1.29 (m, 1H), 1.25 (t, J=7.1 Hz, 1H), 1.15 (s, 9H).

$^{13}$C NMR (100 MHz, $CDCl_3$) δ 171.7, 169.4, 156.0, 143.9, 143.7, 141.2, 127.6, 127.0, 125.1, 119.9, 119.9, 82.0, 73.9, 67.0, 67.0, 58.4, 54.6, 47.1, 32.9, 29.6, 28.7, 28.4, 28.1, 22.2, 21.0 ppm.

HRMS m/z (ESI) calcd for $C_{38}H_{56}N_3O_8$ $(M+H)^+$: 682.4062, found: 682.4067.

Example A18

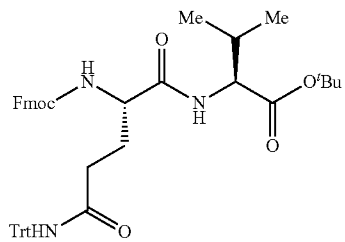

In a clean 4 mL reaction vial were added α-carbonyl alkenyl ester (from Preparative Example 28) (0.20 mmol) and 1.5 mL of N,N-dimethylformamide (DMF), followed by H-LVal-OtBu (0.22 mmol); then the reaction was stirred at room temperature for 15 min, and the completion of the reaction was monitored by TLC; after the reaction was completed, the pure product was obtained by column chromatography as a white solid with a yield of 98%.

$^1$H NMR (400 MHz, $CDCl_3$) δ 7.73 (d, J=7.5 Hz, 2H), 7.57 (d, J=7.5 Hz, 2H), 7.36 (t, J=7.5 Hz, 2H), 7.30-7.16 (m, 17H), 7.04 (s, 1H), 5.96 (d, J=7.2 Hz, 1H), 4.37-4.32 (m, 2H), 4.28 (dd, J=8.3, 4.8 Hz, 1H), 4.19 (t, J=7.5 Hz, 2H), 2.53 (s, 2H), 2.18-2.04 (m, 2H), 2.04-1.91 (m, 2H), 1.41 (s, 9H), 0.84 (d, J=6.8 Hz, 3H), 0.78 (d, J=6.9 Hz, 3H).

$^{13}$C NMR (100 MHz, $CDCl_3$) δ 171.8, 171.3, 170.6, 156.1, 144.5, 143.8, 143.7, 141.2, 141.1, 128.6, 127.8, 127.6, 127.0, 126.9, 125.1, 119.8, 81.7, 70.6, 66.9, 58.0, 53.7, 47.0, 33.4, 30.5, 29.8, 27.9, 18.9, 17.5 ppm.

HRMS m/z (ESI) calcd for $C_{48}H_{51}N_3NaO_6$ $(M+Na)^+$: 788.3670, found: 788.3671.

Example A19

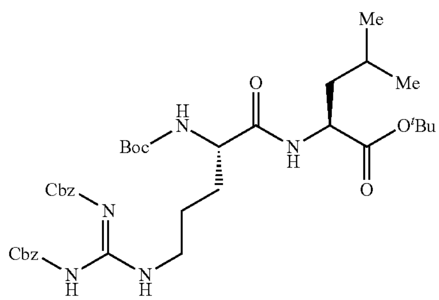 [SMILES: CC(C)C[C@H](NC(=O)[C@H](CCCN/C(=N/C(=O)OCc1ccccc1)NC(=O)OCc1ccccc1)NC(=O)OC(C)(C)C)C(=O)OC(C)(C)C]

In a clean 4 mL reaction vial were added α-carbonyl alkenyl ester (from Preparative Example 29) (0.20 mmol) and 1.5 mL of N,N-dimethylformamide (DMF), followed by H-L-Leu-OtBu (0.22 mmol); then the reaction was stirred at room temperature for 10 min, and the completion of the reaction was monitored by TLC; after the reaction was completed, the pure product was obtained by column chromatography as a white solid with a yield of 85%.

$^1$H NMR (400 MHz, $CDCl_3$) δ 9.36 (d, J=68.9 Hz, 2H), 7.43-7.32 (m, 9H), 7.30-7.25 (m, 1H), 6.61 (d, J=8.4 Hz, 1H), 5.51 (d, J=8.7 Hz, 1H), 5.24 (s, 1H), 5.16 (q, J=12.7 Hz, 2H), 4.42 (td, J=8.7, 5.5 Hz, 2H), 4.20 (d, J=7.8 Hz, 1H), 4.08-3.89 (m, 1H), 1.81-1.52 (m, 5H), 1.42 (s, 18H), 1.36-1.27 (m, 2H), 0.86 (t, J=6.1 Hz, 6H).

$^{13}$C NMR (100 MHz, $CDCl_3$) δ 171.5, 163.6, 160.6, 155.7, 136.7, 134.6, 128.7, 128.7, 128.4, 128.2, 127.7, 127.7, 81.5, 79.7, 68.8, 66.9, 53.9, 51.2, 44.0, 41.4, 28.4, 28.2, 27.9, 24.8, 24.6, 22.6, 21.9 ppm.

HRMS m/z (ESI) calcd for $C_{37}H_{54}N_5O_9$ $(M+H)^+$: 712.3916, found: 712.3921.

Example A20

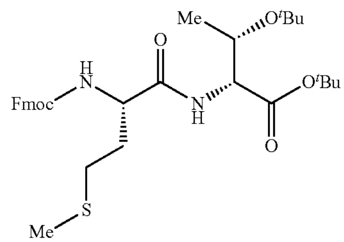

In a clean 4 mL reaction vial were added α-carbonyl alkenyl ester (from Preparative Example 21) (0.20 mmol) and 1.5 mL of N,N-dimethylformamide (DMF), followed by H-L-Thr(tBu)-OtBu (0.22 mmol); then the reaction was stirred at room temperature for 15 min, and the completion of the reaction was monitored by TLC; after the reaction, the pure product was obtained by column chromatography as a white solid with a yield of 99%.

$^1$H NMR (400 MHz, $CDCl_3$) δ 7.75 (d, J=7.5 Hz, 2H), 7.59 (d, J=7.4 Hz, 2H), 7.39 (t, J=7.4 Hz, 2H), 7.30 (t, J=7.4 Hz, 2H), 6.74 (d, J=8.8 Hz, 1H), 5.72 (d, J=8.1 Hz, 1H), 4.52 (q, J=7.2 Hz, 1H), 4.42-4.36 (m, 2H), 4.33 (dd, J=8.9, 1.9 Hz, 1H), 4.26-4.18 (m, 2H), 2.76-2.62 (m, 2H), 2.17-2.00 (m, 5H), 1.46 (s, 9H), 1.16 (s, 9H).

$^{13}$C NMR (100 MHz, $CDCl_3$) δ 171.1, 169.3, 155.7, 143.8, 143.7, 141.2, 127.6, 127.0, 125.0, 125.0, 119.9, 119.9, 82.0, 73.8, 66.9, 66.9, 58.6, 53.3, 47.1, 32.2, 29.7, 28.6, 28.0, 21.1, 14.8 ppm.

HRMS m/z (ESI) calcd for $C_{32}H_{45}N_2O_6S$ $(M+H)^+$: 585.2993, found: 585.2991.

Example A21

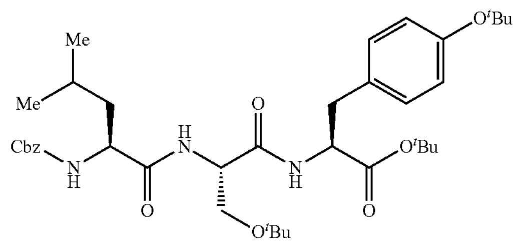 [SMILES: CC(C)C[C@H](NC(=O)OCc1ccccc1)C(=O)N[C@@H](COC(C)(C)C)C(=O)N[C@@H](Cc1ccc(OC(C)(C)C)cc1)C(=O)OC(C)(C)C]

In a clean 4 mL reaction vial were added α-carbonyl alkenyl ester (from Preparative Example 30) (0.20 mmol) and 1.5 mL of N,N-dimethylformamide (DMF), followed by H-L-Tyr(tBu)-OtBu (0.22 mmol); then the reaction was stirred at room temperature for 20 min, and the completion of the reaction was monitored by TLC; after the reaction, the pure product was obtained by column chromatography as a white solid with a yield of 99%.

$^1$H NMR (400 MHz, $CDCl_3$) δ 7.38-7.27 (m, 5H), 7.06 (d, J=8.1 Hz, 2H), 6.91-6.87 (m, 2H), 6.82 (d, J=6.6 Hz, 1H), 5.27 (d, J=8.3 Hz, 1H), 5.14-5.06 (m, 2H), 4.68 (q, J=6.5 Hz, 1H), 4.43-4.36 (m, 1H), 4.28-4.19 (m, 1H), 3.81 (dd, J=8.8, 3.7 Hz, 1H), 3.32 (t, J=8.4 Hz, 1H), 3.07-2.96 (m, 2H), 1.73-1.59 (m, 2H), 1.57-1.48 (m, 1H), 1.35 (s, 9H), 1.31 (s, 9H), 1.17 (s, 9H), 0.92 (t, J=6.2 Hz, 6H).

$^{13}$C NMR (100 MHz, $CDCl_3$) δ 172.1, 170.0, 169.5, 156.0, 154.3, 136.2, 131.0, 129.9, 128.5, 128.1, 128.0, 123.9, 82.0, 78.2, 74.3, 67.0, 61.1, 53.9, 53.5, 52.9, 41.8, 37.5, 28.8, 27.9, 27.3, 24.7, 22.9, 21.9 ppm.

HRMS m/z (ESI) calcd for $C_{38}H_{58}N_3O_8$ $(M+H)^+$: 684.4218, found 684.4220.

Application Example B

A one-pot two-step method was used to prepare amides with the general formula (V).

Example B1

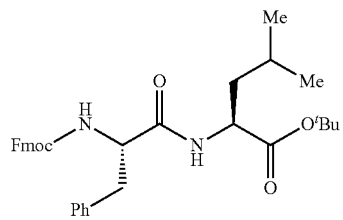

In a clean 100 mL round-bottom flask were added allenone (10 mmol) and 40 mL of 1,2-dichloroethane (DCE), followed by Fmoc-L-Phe-OH (11 mmol).); then the reaction was stirred at room temperature for 10 h, and the completion of the reaction was monitored by TLC; after the reaction was completed, the reaction solvent was removed in vacuo; thereto 20 mL of N,N-dimethylformamide (DMF) and H-L-Leu-OtBu (11 mmol) were added and stirred at room temperature for 10 min, and the completion of the reaction was monitored by TLC; after the reaction was completed, 100 mL of water was added to the reaction system, and 100 mL of ethyl acetate was used to extract three times, the organic layers combined, the organic layer washed 3 times with 100 mL of water, dried over anhydrous magnesium sulfate and recrystallized to obtain a pure product as a white solid with a yield of 82%.

$^1$H NMR (400 MHz, $CDCl_3$) δ 7.77 (d, J=7.5 Hz, 2H), 7.55 (t, J=7.8 Hz, 2H), 7.40 (t, J=7.5 Hz, 2H), 7.35-7.15 (m, 7H), 6.59 (s, 1H), 5.63 (d, J=7.1 Hz, 1H), 4.57 (d, J=5.7 Hz, 1H), 4.52-4.41 (m, 2H), 4.33-4.23 (m, 1H), 4.18 (t, J=7.0 Hz, 1H), 3.11 (d, J=5.3 Hz, 2H), 1.68-1.50 (m, 3H), 1.47 (s, 9H), 0.90 (t, J=5.1 Hz, 6H).

$^{13}$C NMR (100 MHz, $CDCl_3$) δ 171.5, 170.4, 155.8, 143.70, 143.6, 141.2, 136.2, 129.3, 128.5, 127.6, 127.0, 126.9, 125.0, 124.9, 119.8, 81.8, 67.0, 55.8, 51.4, 47.0, 41.7, 38.5, 27.9, 24.7, 22.6, 22.0 ppm.

HRMS m/z (ESI) calcd for $C_{34}H_{40}N_2NaO_5$ $(M+Na)^+$: 579.2829, found: 579.2830.

Example B2

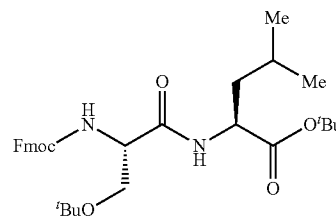

In a clean 100 mL round bottom flask were added allenone (10 mmol) and 40 mL of 1,2-dichloroethane (DCE) followed by Fmoc-L-Ser(tBu)-OH (11 mmol); then the reaction was stirred at room temperature for 5 h, and the completion of the reaction was monitored by TLC; after the reaction was completed, the reaction solvent was removed in vacuo; thereto 20 mL of N,N-dimethylformamide (DMF) and H-L-Leu-OtBu (11 mmol) were then added, the reaction was stirred at room temperature for 10 min, and the completion of the reaction was monitored by TLC; 100 mL of water was added to the reaction system after the reaction, and 100 mL of ethyl acetate was used to extract 3 times, the organic layers combined, the organic layer washed 3 times with 100 mL of water, dried over anhydrous magnesium sulfate, and recrystallized to obtain the pure product as a white solid with a yield of 86%.

$^1$H NMR (400 MHz, $CDCl_3$) δ 7.75 (d, J=7.5 Hz, 2H), 7.65-7.54 (m, 2H), 7.39 (t, J=7.5 Hz, 2H), 7.31 (t, J=7.5 Hz, 2H), 7.23 (d, 1H), 5.82-5.76 (m, 1H), 4.48 (q, J=7.4 Hz, 1H), 4.43-4.35 (m, 2H), 4.30-4.16 (m, 2H), 3.83 (dd, J=8.5, 3.8 Hz, 1H), 3.40 (t, J=8.4 Hz, 1H), 1.73-1.59 (m, 2H), 1.57-1.51 (m, 1H), 1.46 (s, 9H), 1.22 (s, 9H), 0.95 (d, J=6.4 Hz, 6H).

$^{13}$C NMR (100 MHz, $CDCl_3$) δ 171.6, 169.9, 156.0, 143.9, 143.8, 141.3, 127.7, 127.1, 125.2, 120.0, 81.7, 74.3, 67.1, 61.8, 54.3, 51.7, 47.2, 41.9, 28.0, 27.4, 24.9, 22.8, 22.2 ppm.

HRMS m/z (ESI) calcd for $C_{32}H_{44}N_2NaO_6$ $(M+Na)^+$: 575.3092, found: 575.3090.

Application Example C

A solid-phase synthesis method of leucine enkephalin comprising:

1) using 2-CTC resin as a carrier, adding Fmoc-Leu-OH and coupling in a solvent in the presence of a base to obtain Fmoc-Leu-resin;

2) removing the Fmoc protecting group on the Fmoc-Leu-resin by using a DMF solution containing piperidine to obtain the H-Leu-resin;

3) in the presence of a catalyst, adding the α-carbonyl alkenyl ester compound corresponding to Fmoc-Phe-OH, reacting in a solvent (the end of reaction being monitored by Kaiser color test), and washing with a solvent after the reaction is completed (sequentially washing with DCM and DMF) and draining to obtain Fmoc-Phe-Leu-resin;

4) repeating the two-step reaction of 2) and 3), and sequentially linking amino acid residue into the peptide chain using α-carbonyl alkenyl esters corresponding to amino acids such as Gly and Tyr according to the amino acid sequence;

5) deprotecting, cleaving, and removing the side chain protecting groups and resin, followed by precipitation in ether to obtain crude peptide H-Tyr-Gly-Gly-Phe-Leu-OH (SEQ ID NO:1);

6) purifying and freeze-drying to obtain the target polypeptide chain.

therein, the structure of the H-Tyr-Gly-Gly-Phe-Leu-OH (SEQ ID NO:1) sequence is:

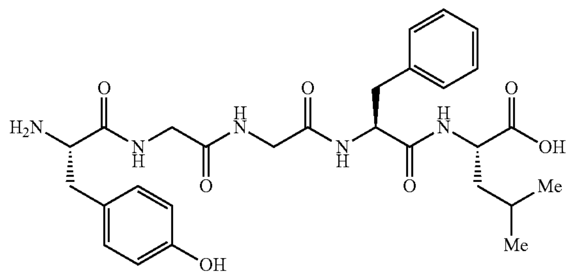

wherein, the way of coupling the first amino acid with the 2-CTC resin is to add the first Fmoc-Protected amino acid to a solid-phase reaction vessel, and to link the protected amino acid to the 2-CTC resin under a base reaction condition in a solvent.

The following examples are only typical examples, which will help to further illustrate and understand the present invention, but these typical examples do not limit the content of the present invention.

Example C1

1) Synthesis of Fmoc-Leu-Resin:

64.9 mg of 2-CTC resin (loading capacity 0.77 mmol/g) was added to a solid-phase synthesis tube, and 3 mL of dichloromethane was added to soak for 20 min. After soaking, the excess solvent was removed by suction filtration, thereto 0.15 mmol Fmoc-Leu-OH, 0.15 mmol N,N-diisopropylethylamine (DIEA), 1.5 mL DMF and 1.5 mL DCM were added, and the reaction was stirred for 2 h. The reaction solution was filtered off with suction, washed with solvent (DMF), and dried by suction to obtain Fmoc-Leu-resin.

2) Synthesis of H-Leu-Resin:

0.75 mL of 20% DMF solution of piperidine was added to the solid-phase synthesis tube containing Fmoc-Leu-resin, and the reaction was stirred for 20 min. The reaction solution was filtered off with suction, washed with solvent (DMF) and dried by suction to obtain H-Leu-resin.

3) Synthesis of Fmoc-Phe-Leu-Resin:

To a solid-phase synthesis tube containing H-Leu-resin were add 0.015 mmol HOBt, 0.15 mmol α-carbonyl alkenyl ester corresponding to Fmoc-Phe-OH and 3 mL DMF, and the reaction was stirred (the end of reaction being monitored by Kaiser color test), the reaction solution was filtered off with suction, washed with solvent (DMF), and dried by suction to obtain Fmoc-Phe-Leu-resin.

4) Synthesis of H-Tyr(tBu)-Gly-Gly-Phe-Leu-Resin (SEQ ID NO:1 Wherein the First Amino Acid Tyr is Tyr(tBu)):

Steps 2) and 3) were repeated according to the sequence of H-Tyr(tBu)-Gly-Gly-Phe-Leu-resin (SEQ ID NO:1 wherein the first amino acid Tyr is Tyr(tBu)), the respective α-carbonyl alkenyl esters corresponding to Tyr, Gly, etc. in the sequence were sequentially added to obtain H-Tyr(tBu)-Gly-Gly-Phe-Leu-resin (SEQ ID NO:1 wherein the first amino acid Tyr is Tyr(tBu)).

5) The Leucine Enkephalin Resin was Cleaved to Obtain Crude Enkephalin:

A cleavage cocktail ($TFA:TIS:H_2O=95:2.5:2.5$) was added to the solid-phase synthesis tube containing H-Tyr(tBu)-Gly-Gly-Phe-Leu-resin (SEQ ID NO:1 wherein the first amino acid Tyr is Tyr(tBu)), reacted at room temperature for 2 h, the solution was filtered out, the resin was washed three times with TFA and filtered, the filtrates were combined, thereto 10 mL of ether was added, the crude product was precipitated, washed with 3×10 mL of ether, and dried to obtain the crude leucine enkephalin product.

6) Purification of Crude Leucine Enkephalin:

2 mg of the crude leucine enkephalin product was dissolved in 0.25 mL of water, and filtered through a membrane to obtain an aqueous solution of the crude product for later use. C18 reverse chromatographic column was used for separation, mobile phase A: 0.1% TFA, 10% $H_2O$, 90% MeCN, mobile phase B: 0.1% TFA, 100% $H_2O$, gradient elution to obtain pure leucine enkephalin solution. The solution was concentrated to 2 mL and lyophilized to obtain pure leucine enkephalin.

Figure 2:
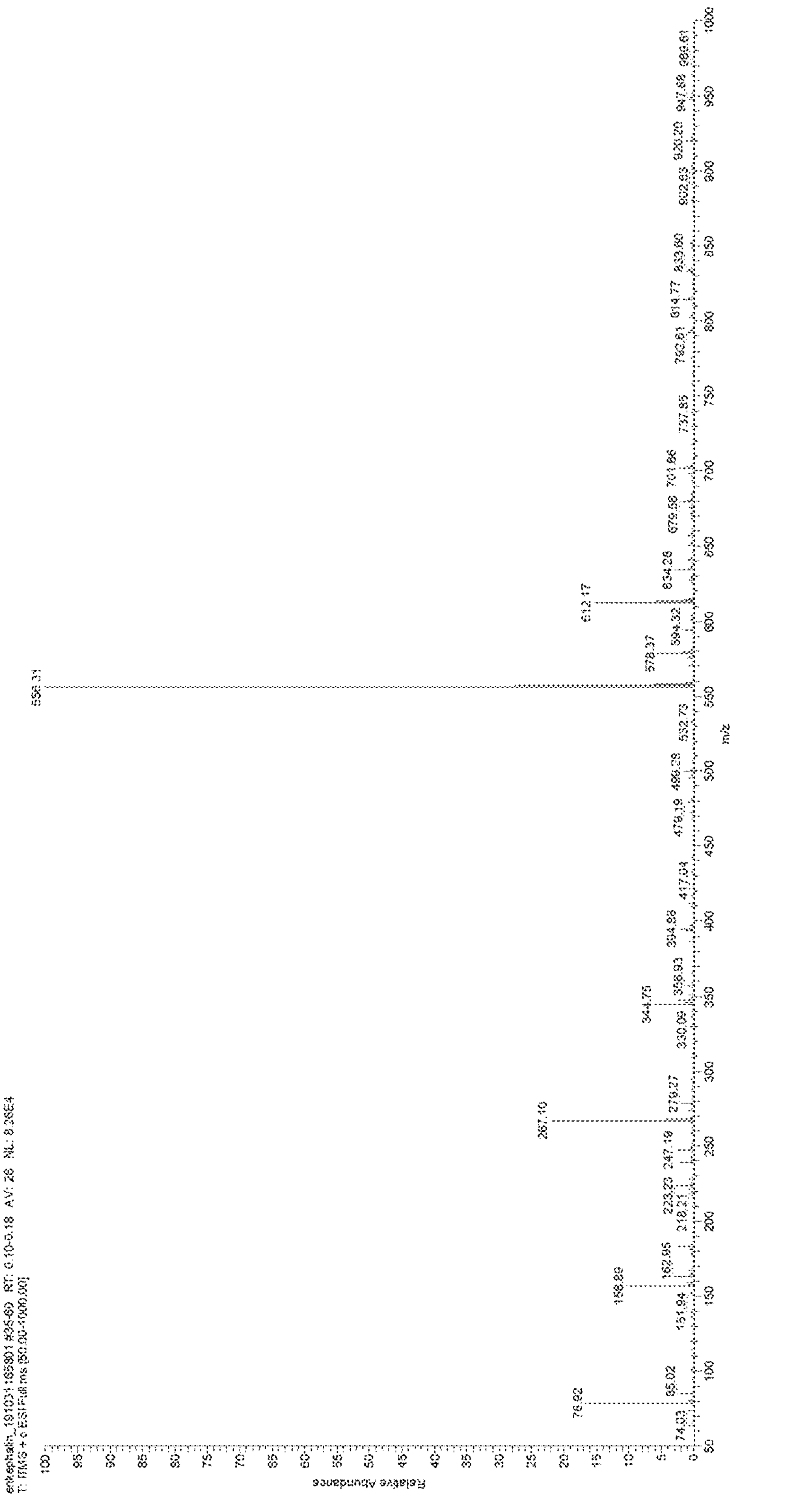
FIG. 2 is LC-MS chart of leucine enkephalin product.

The obtained pure leucine enkephalin was detected by high performance liquid chromatography, and the results are shown in FIG. 1. The obtained pure leucine enkephalin was detected by liquid chromatography-mass spectrometry, and the results are shown in FIG. 2.

Application Example D

A solid-phase synthesis method for a linear skeleton of oxytocin, comprising:

1) using MBHA resin as the carrier, adding α-carbonyl alkenyl ester corresponding to Fmoc-Gly-OH protected by N-terminal Fmoc group, and coupling in solvent in the presence of catalyst to obtain Fmoc-Gly-resin;

2) removing the Fmoc protecting group on the Fmoc-Gly-resin by using a DMF solution containing piperidine to obtain the H-Gly-resin;

3) in the presence of a catalyst, adding the α-carbonyl alkenyl ester corresponding to Fmoc-Leu-OH and carrying out reaction in a solvent (the end of reaction being monitored by Kaiser color test), washing the resulting resin with a solvent after the reaction is completed (sequentially washed with DCM and DMF) and draining to obtain Fmoc-Leu-Gly-resin;

4) repeating the two-step reaction of 2) and 3), and sequentially linking amino acid residue into the peptide chain using α-carbonyl alkenyl esters corresponding to amino acids such as Cys(Me), Tyr, Ile, Gln, Asn, Cys(Me), and Pro according to the amino acid sequence;

5) deprotecting, cleaving, and removing the side chain protecting group and resin, and then precipitating in ether to obtain the crude peptide H-Cys(Me)-Tyr-Ile-Gln-Asn-Cys(Me)-Pro-Leu-Gly-OH (SEQ ID NO:2 wherein the first and sixth amino acids Cys are Cys (Me), respectively);

6) Purifying and freeze-drying to obtain the target polypeptide chain, wherein, the structure of H-Cys(Me)-Tyr-Ile-Gln-Asn-Cys(Me)-Pro-Leu-Gly-$NH_2$ sequence (SEQ ID NO:2 wherein the first and sixth amino acids Cys are Cys(Me), respectively) is:

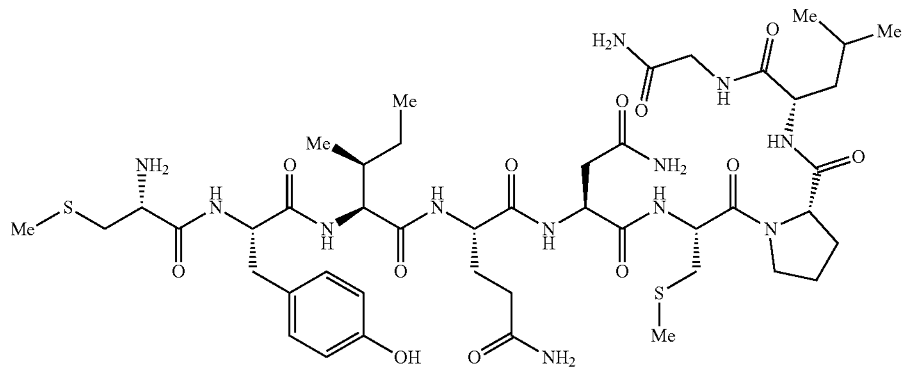

wherein, the way of coupling the first amino acid with the MBHA resin is to add the α-carbonyl alkenyl ester corresponding to the first amino acid in a solid-phase reaction vessel, and then link the protected amino acid residue to the MBHA resin in the presence of a catalyst.

Example D1

1) Synthesis of Fmoc-Gly-Resin:

39.0 mg MBHA resin (loading capacity 0.77 mmol/g) was added to a solid-phase synthesis tube, and 3 mL of dichloromethane was added to soak for 20 min. After soaking, the excess solvent was filtered off with suction, thereto 0.15 mmol of α-carbonyl alkenyl ester corresponding to Fmoc-Gly-OH, 0.015 mmol HOBt and 3 mL DMF were added, and the reaction was stirred to complete (the end of reaction being monitored by Kaiser color test), the reaction solution was filtered off with suction, washed with solvent (DMF), and dried by suction to obtain Fmoc-Gly-resin.

2) Synthesis of H-Gly-Resin:

0.75 mL of 20% piperidine in DMF solution was added to the solid-phase synthesis tube containing Fmoc-Leu-resin, and the reaction was stirred for 20 min. The reaction solution was filtered off with suction, washed with solvent (DMF), and dried by suction to obtain H-Gly-resin.

3) Synthesis of Fmoc-Leu-Gly-Resin:

In a solid-phase synthesis tube containing H-Gly-resin were added 0.015 mmol HOBt, 0.15 mmol α-carbonyl alkenyl ester corresponding to Fmoc-Leu-OH and 3 mL DMF, and the reaction was stirred to complete (the end of reaction being monitored by Kaiser color test), the reaction solution was filtered off with suction, washed with solvent (DMF), and dried by suction to obtain Fmoc-Leu-Gly-resin.

4) Synthesis of H-Cys(Me)-Tyr-Ile-Gln-Asn-Cys(Me)-Pro-Leu-Gly-Resin (SEQ ID NO:2 Wherein the First and Sixth Amino Acids Cys are Cys(Me), Respectively):

Steps 2) and 3) were repeated according to the sequence of H-Cys(Me)-Tyr-Ile-Gln-Asn-Cys(Me)-Pro-Leu-Gly-resin (SEQ ID NO:2), α-carbonyl alkenyl esters corresponding to amino acids such as Cys(Me), Tyr(tBu), Ile, Gln(Trt), Asn(Trt), Pro were linked sequentially added to obtain H-Cys(Me)-Tyr-Ile-Gln-Asn-Cys(Me)-Pro-Leu-Gly-resin (SEQ ID NO:2 wherein the first and sixth amino acids Cys are Cys(Me), respectively).

5) The Oxytocin Linear Skeleton Resin is Cleaved to Obtain the Crude Oxytocin Linear Skeleton:

The cleavage cocktail (TFA:EDT:TIS:HO=92.5:2.5:2.5:2.5) was added to the solid-phase synthesis tube containing H-Cys(Me)-Tyr-Ile-Gln-Asn-Cys(Me)-Pro-Leu-Gly-resin (SEQ ID NO:2 wherein the first and sixth amino acids Cys are Cys(Me), respectively) and reacted at room temperature for 2 h, the solution was filtered out, the resin washed with TFA for 3 times and filtered, the filtrates were combined, thereto 10 mL of ether was added, and the crude product was separated out, washed with 3×10 mL of ether and dried to obtain crude oxytocin linear peptide.

6) Purification of Crude Oxytocin Linear Skeleton:

2 mg of the crude oxytocin linear skeleton was dissolved in 0.25 mL of water, and filtered through a membrane to obtain an aqueous solution of the crude peptide for later use. C18 reverse chromatographic column was used for separation, mobile phase A: 0.1% TFA, 10% $H_2O$, 90% MeCN, mobile phase B: 0.1% TFA, 100% $H_2O$, gradient elution to obtain pure oxytocin linear skeleton solution. The solution was concentrated to 2 mL and lyophilized to obtain pure oxytocin linear peptide.

Figure 3:
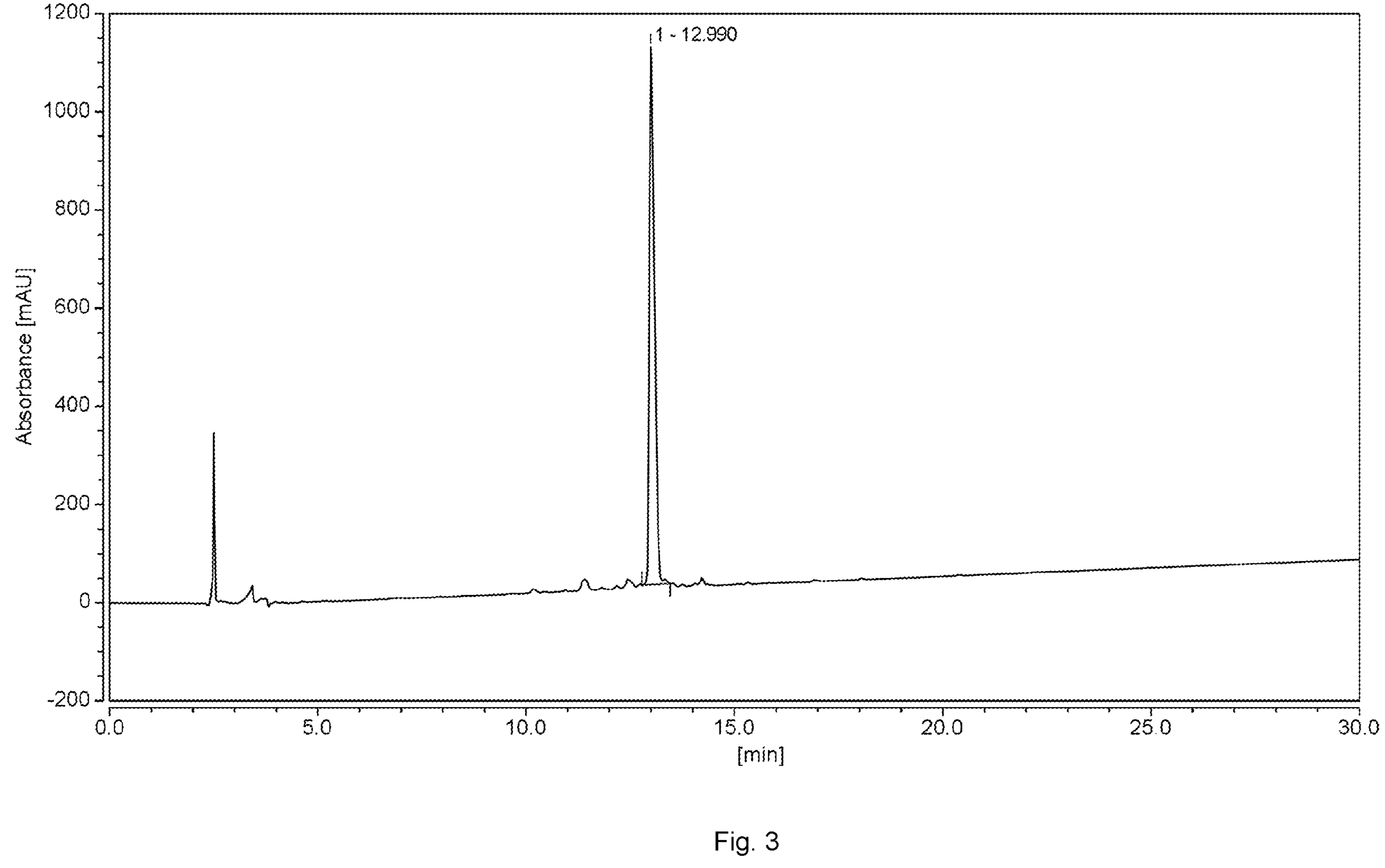
FIG. 3 is HPLC chart of oxytocin linear backbone crude product.
Figure 4:
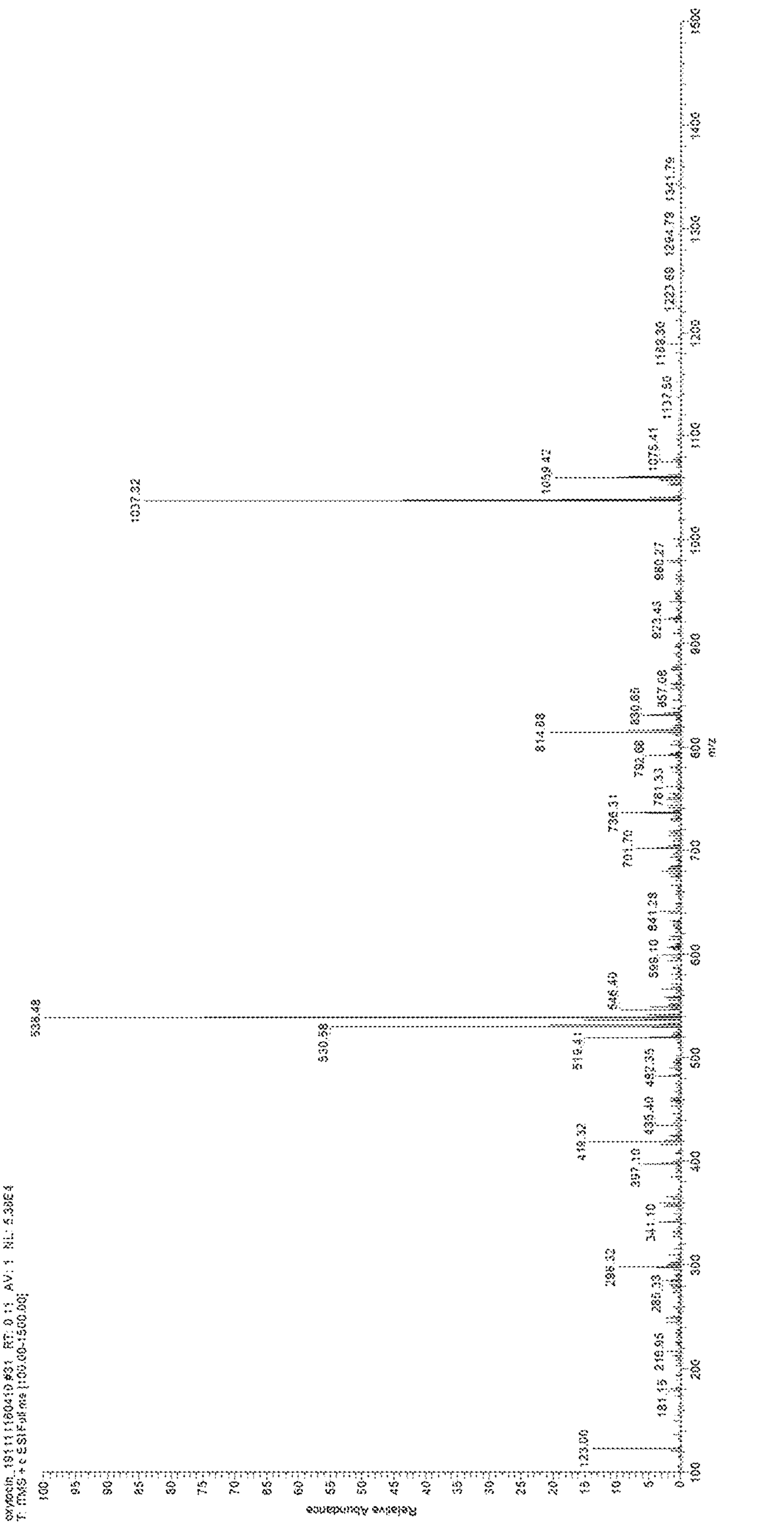
FIG. 4 is LC-MS chart of the oxytocin linear backbone product.

The obtained pure oxytocin linear peptide was detected by high performance liquid chromatography, and the results are shown in FIG. 3. The obtained pure oxytocin linear peptide was tested by liquid chromatography-mass spectrometry, and the results are shown in FIG. 4.

The above-described examples only describe the preferred embodiment of the invention, and do not limit the scope of the invention. Without departing from the concept and spirit of the invention, various modifications and improvements made by those skilled in the art to the technical scheme of the invention should fall within the protection scope determined by the claims of the invention.

REFERENCES TO THE SEQUENCE LISTING

Applicant hereby makes reference to the sequence listing that is submitted in electronic format. The Sequence Listing is provided as a file entitled 53208_SEQLIST.txt, created on Jan. 16, 2022 which is 681 bytes in size. The information in the electronic format of the sequence listing is incorporated herein by reference in its entirety.

The invention claimed is:

1. An α-carbonyl alkenyl ester having the general formula (I):

(I)

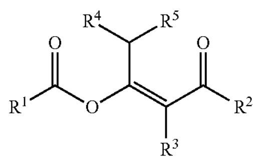

wherein $R^1$ is selected from one of protected α-amino C1-C20 hydrocarbyl, protected β-amino C2-C20 hydrocarbyl, protected γ-amino C3-C20 hydrocarbyl, and protected polypeptide chain C1-C20 hydrocarbyl;

$R^2$ is selected from one of aryl, aryl substituted by a substituent(s), heteroaryl and heteroaryl substituted by a substituent(s);

$R^3$, $R^4$ and $R^5$ are the same or different, and are each independently selected from one of H, C1-C18 hydrocarbyl, C1-C18 hydrocarbyl substituted by a substituent(s), C1-C16 acyl, cyano, halogen or C1-C16 hydrocarbyloxy-carbonyl.

2. The compound as claimed in claim 1, wherein $R^1$ is selected from one of protected α-amino C2-C10 hydrocarbyl, protected β-amino C3-C10 hydrocarbyl, protected γ-amino C4-C10 hydrocarbyl, and protected polypeptide chain C2-C15 hydrocarbyl;

$R^2$ is selected from one of C6-C24 aryl, C6-C24 aryl substituted by a substituent(s), C4-C24 heteroaryl, and C4-C24 heteroaryl substituted by a substituent(s);

$R^3$, $R^4$ and $R^5$ are the same or different, and are each independently selected from one of H, C1-C12 hydrocarbyl, C1-C12 hydrocarbyl substituted by a substituent(s), C1-C16 acyl, cyano, halogen or C2-C12 hydrocarbyloxy-carbonyl.

3. The compound as claimed in claim 2, for $R^3$, $R^4$ and $R^5$, the substituent(s) is C1-C8 hydrocarbyloxy, C1-C8 halohydrocarbyloxy, C1-C8 hydrocarbylthio, C1-C8 halo hydrocarbylthio, C1-C8 acyl, C1-C8 haloacyl, C1-C8 acyloxy, C1-C8 haloacyloxy, halogen, nitro and/or cyano; and/or in $R^2$, the substituent(s) is C1-C8 hydrocarbyl, C1-C8 halohydrocarbyl, C1-C8 hydrocarbyloxy, C1-C8 halohydrocarbyloxy, C1-C8 hydrocarbylthio, C1-C8 halo hydrocarbylthio, C1-C8 acyl, C1-C8 haloacyl, C1-C8 acyloxy, C1-C8 haloacyloxy, halogen, nitro and/or cyano.

4. The compound as claimed in claim 1, wherein, the compound having the general formula (I) is one selected from the following compounds:

(E)-4-oxo-4-phenylbut-2-en-2-yl 3-((((9H-fluoren-9-yl)methoxy)carbonyl)amino) propanoate:

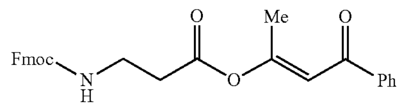

(E)-4-oxo-4-phenylbut-2-en-2-yl (((9H-fluoren-9-yl)methoxy)carbonyl)-L-alaninate:

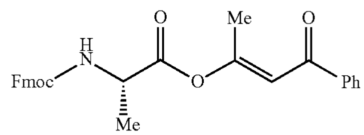

(E)-4-oxo-4-phenylbut-2-en-2-yl ((benzyloxy)carbonyl)-L-alaninate:

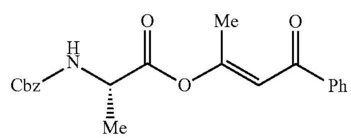 [SMILES: C/C(=C\C(=O)c1ccccc1)OC(=O)[C@H](C)NC(=O)OCc1ccccc1]

(E)-4-oxo-4-phenylbut-2-en-2-yl ((benzyloxy)carbonyl)-L-serinate:

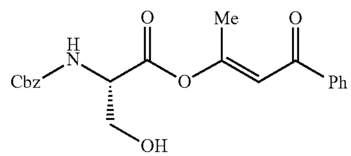 [SMILES: C/C(=C\C(=O)c1ccccc1)OC(=O)[C@H](CO)NC(=O)OCc1ccccc1]

(E)-4-oxo-4-phenylbut-2-en-2-yl (((9H-fluoren-9-yl) methoxy)carbonyl)-L-threoninate:

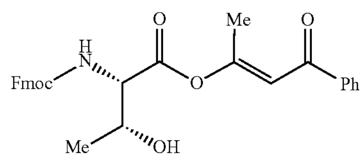

(E)-4-oxo-4-phenylbut-2-en-2-yl (((9H-fluoren-9-yl) methoxy)carbonyl)-L-tryptophanate:

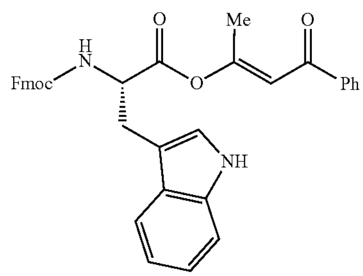

(E)-4-oxo-4-phenylbut-2-en-2-yl (tert-butoxycarbonyl)-L-threoninate:

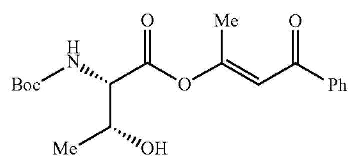 [SMILES: C/C(=C\C(=O)c1ccccc1)OC(=O)[C@@H](NC(=O)OC(C)(C)C)[C@@H](C)O]

(E)-4-oxo-4-phenylbut-2-en-2-yl (tert-butoxycarbonyl)-L-phenylalaninate:

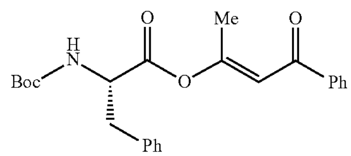 [SMILES: C/C(=C\C(=O)c1ccccc1)OC(=O)[C@H](Cc1ccccc1)NC(=O)OC(C)(C)C]

(E)-4-oxo-4-phenylbut-2-en-2-yl (((9H-fluoren-9-yl) methoxy)carbonyl)-L-leucinate:

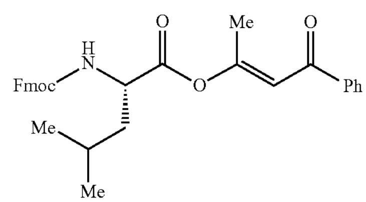

(E)-4-oxo-4-phenylbut-2-en-2-yl (((9H-fluoren-9-yl) methoxy)carbonyl)glycinate:

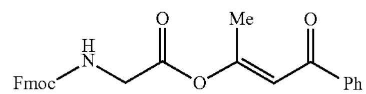

(E)-4-(tert-butyl) 1-(4-oxo-4-phenylbut-2-en-2-yl) (((9H-fluoren-9-yl)methoxy) carbonyl)-L-aspartate:

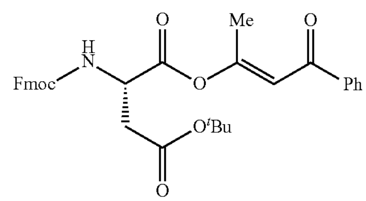

(E)-4-oxo-4-phenylbut-2-en-2-yl N-(((9H-fluoren-9-yl) methoxy)carbonyl)-S-trityl-L-cysteinate:

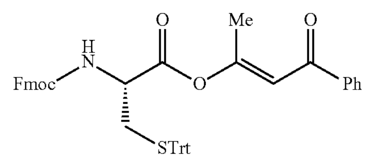

(E)-4-oxo-4-phenylbut-2-en-2-yl(S)-2-((((9H-fluoren-9-yl)methoxy)carbonyl)amino)-2-phenylacetat-e:

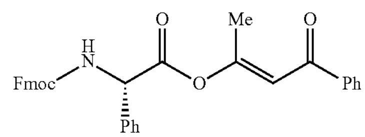

(E)-4-oxo-4-phenylbut-2-en-2-yl (((9H-fluoren-9-yl)methoxy)carbonyl)-L-methioninate:

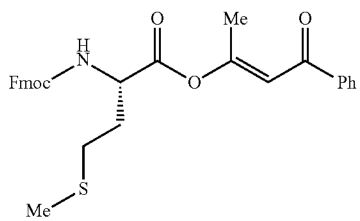

(E)-4-oxo-4-phenylbut-2-en-2-yl $N^2$-(((9H-fluoren-9-yl)methoxy)carbonyl)-$N^6$-(tert-butoxycarbonyl)-L-lysinate:

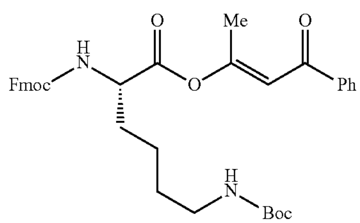

(E)-4-oxo-4-phenylbut-2-en-2-yl $N^2$-(((9H-fluoren-9-yl)methoxy)carbonyl)-$N^4$-trityl-L-asparaginate:

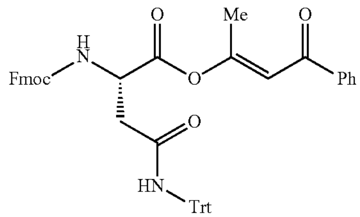

(E)-4-oxo-4-phenylbut-2-en-2-yl (((9H-fluoren-9-yl)methoxy)carbonyl)-L-isoleucinate:

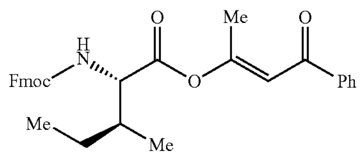

tert-butyl (S,E)-4-(2-((((9H-fluoren-9-yl)methoxy)carbonyl)amino)-3-oxo-3-((4-oxo-4-phenylbut-2-en-2-yl)oxy)propyl)-1H-imidazole-1-carboxylate:

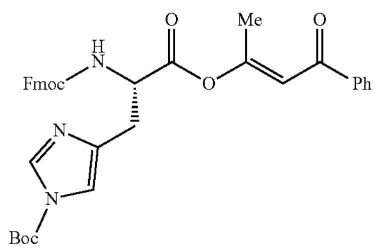

(E)-4-oxo-4-phenylbut-2-en-2-yl(S)-2-((((9H-fluoren-9-yl)methoxy)carbonyl)amino)-3-(4-(tert-but-oxy)phenyl)propanoate:

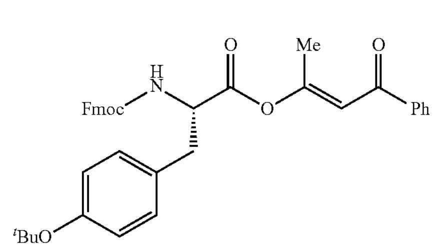

(E)-1-((9H-fluoren-9-yl)methyl) 2-(4-oxo-4-phenylbut-2-en-2-yl) (S)-pyrrolidine-1,2-dicarboxylate:

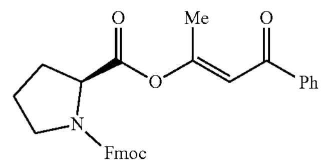

(E)-4-oxo-4-phenylbut-2-en-2-yl $N^2$-(((9H-fluoren-9-yl)methoxy)carbonyl)-$N^5$-trityl-L-glutaminate:

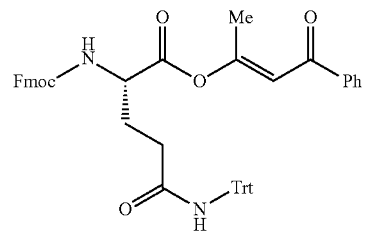

(E)-4-oxo-4-phenylbut-2-en-2-yl (Z)—$N^{\omega}$,$N^{\omega'}$-bis(benzyloxy)carbonyl)-$N^2$-(tert-butoxycarbonyl)-L-argininate:

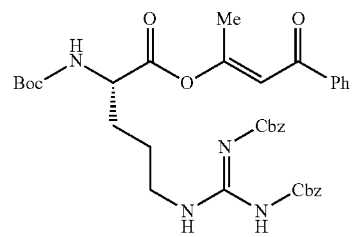 [SMILES: C/C(=C\C(=O)c1ccccc1)OC(=O)[C@H](CCCN/C(=N/C(=O)OCc1ccccc1)NC(=O)OCc1ccccc1)NC(=O)OC(C)(C)C]

(E)-4-oxo-4-phenylbut-2-en-2-yl (((9H-fluoren-9-yl)methoxy)carbonyl)-L-alanyl-L-phenylalaninate:

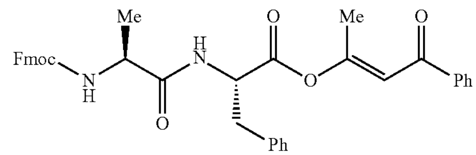

(E)-4-oxo-4-phenylbut-2-en-2-yl ((benzyloxy)carbonyl)-L-valyl-L-phenylalaninate:

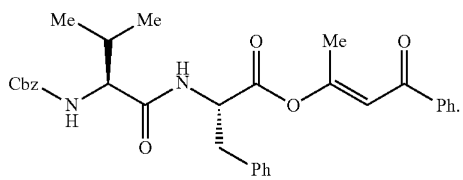 [SMILES: C/C(=C\C(=O)c1ccccc1)OC(=O)[C@H](Cc1ccccc1)NC(=O)[C@@H](NC(=O)OCc1ccccc1)C(C)C]

(E)-4-oxo-4-phenylbut-2-en-2-yl N-(((benzyloxy)carbonyl)-L-leucyl)-O-(tert-butyl)-L-serinate:

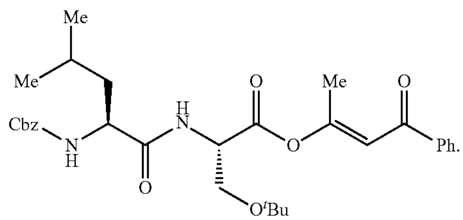 [SMILES: C/C(=C\C(=O)c1ccccc1)OC(=O)[C@H](COC(C)(C)C)NC(=O)[C@H](CC(C)C)NC(=O)OCc1ccccc1]

5. A method for preparing an α-carbonyl alkenyl ester having the general formula (I):

(I)

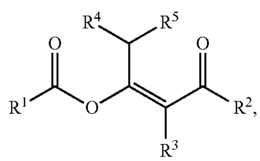

comprising the following steps:

A) reacting the allenone having the general formula (II) with the carboxylic acid having the general formula (III) in a solvent to obtain the target compound:

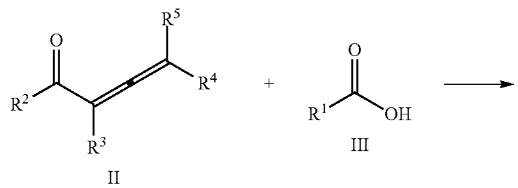

II III

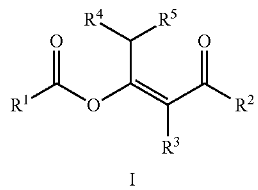

I wherein $R^1$ is selected from one of protected α-amino C1-C12 hydrocarbyl, protected β-amino C2-C20 hydrocarbyl, protected γ-amino C3-C20 hydrocarbyl, and protected polypeptide chain C1-C20 hydrocarbyl;

$R^2$ is selected from one of C1-C24 hydrocarbyl, C1-C24 hydrocarbyl substituted with a substituent(s), aryl, aryl substituted by a substituent(s), heteroaryl and heteroaryl substituted by a substituent(s); and $R^3$, $R^4$ and $R^5$ are the same or different, and are each independently selected from one of H, C1-C18 hydrocarbyl, C1-C18 hydrocarbyl substituted by a substituent(s), C1-C16 acyl, cyano, halogen or C1-C16 hydrocarbyloxy-carbonyl.

6. The method as claimed in claim 5, wherein for $R^3$, $R^4$ and $R^5$, the substituent(s) is selected from C1-C8 hydrocarbyloxy, C1-C8 halohydrocarbyloxy, C1-C8 hydrocarbylthio, C1-C8 halo hydrocarbylthio, C1-C8 acyl, C1-C8 haloacyl, C1-C8 acyloxy, C1-C8 haloacyloxy, halogen, nitro and/or cyano; and/or in $R^2$, the substituent(s) is selected from C1-C8 hydrocarbyl, C1-C8 halohydrocarbyl, C1-C8 hydrocarbyloxy, C1-C8 halohydrocarbyloxy, C1-C8 hydrocarbylthio, C1-C8 halo hydrocarbylthio, C1-C8 acyl, C1-C8 haloacyl, C1-C8 acyloxy, C1-C8 haloacyloxy, halogen, nitro and/or cyano.

7. The method as claimed in claim 5, wherein, in step A), the molar ratio of the allenone having the general formula (II) to the carboxylic acid having the general formula (III) is 1:1-2; and/or step A) comprises: adding the allenone having the general formula (II) and the solvent together into a reactor in proportion, and then adding the carboxylic acid having the general formula (III), reacting at 0-100° C. with stirring for 0.5-320 h, using TLC to monitor the end of the reaction, and obtaining the α-carbonyl alkenyl ester having the general formula (I) by column chromatography from the reaction mixture after the completion of the reaction.

8. A method for preparing the amides having the general formula (V) using α-carbonyl alkenyl ester as intermediates, comprising the following steps:

A) reacting the α-carbonyl alkenyl ester compound having the general formula (I) and the compound having the general formula (IV) in a solvent, and optionally separating the reaction products, to obtain the target compound (V):

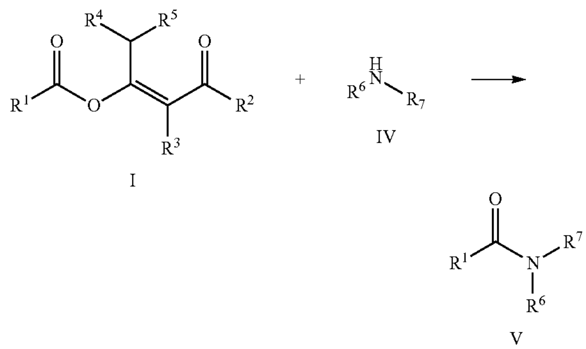

I IV V wherein $R^1$ is selected from one of protected α-amino C1-C20 hydrocarbyl, protected β-amino C2-C20 hydrocarbyl, protected γ-amino C3-C20 hydrocarbyl, and protected polypeptide chain C1-C20 hydrocarbyl;

$R^2$ is selected from one of C1-C24 hydrocarbyl, C1-C24 hydrocarbyl substituted by a substituent(s), aryl, aryl substituted by a substituent(s), heteroaryl and heteroaryl substituted by a substituent(s);

$R^3$, $R^4$, $R^5$ are the same or different, and are each independently selected from one of H, C1-C18 hydrocarbyl, C1-C18 hydrocarbyl substituted by a substituent(s), C1-C16 acyl, cyano, halogen or C1-C16 hydrocarbyloxy-carbonyl; and $R^6$ and $R^7$ are each independently selected from one of H, amino, C1-C24 hydrocarbyl, C1-C24 hydrocarbyl substituted by a substituent(s), or amino oligomers or amino polymers with primary and/or secondary amine group(s); or, $R^6$ and $R^7$ together with the N atom to which they are attached form a C3-C24 cyclic ring.

9. The method as claimed in claim 8, wherein: $R^2$ is selected from one of methyl, ethyl, propyl, isopropyl, butyl, tert-butyl, cyclopentyl, cyclohexyl, phenyl, 4-fluorophenyl, 4-chlorophenyl, 4-bromophenyl, 4-methylphenyl, 4-methoxyphenyl, 2-methylphenyl, 2-methoxyphenyl, 3,5-dimethoxyphenyl, 3-nitrophenyl, 4-nitrophenyl, 2,4-dinitrophenyl, 3,5-dinitrophenyl, pentafluorophenyl, 4-trifluoromethylphenyl, 3,5-dichlorophenyl, 1-naphthyl, 2-naphthyl, furanyl and thienyl; and/or $R^3$, $R^4$, $R^5$ are the same or different from each other, and are each independently selected from one of H, methyl, formyl, acetyl, propionyl, butyryl, cyano, methoxycarbonyl, ethoxycarbonyl, tert-butoxycarbonyl and benzyloxycarbonyl; and/or $R^6$ and $R^7$ are each independently selected from one of H, methyl, ethyl, propyl, isopropyl, butyl, tert-butyl, cyclopentyl, cyclohexyl, cycloheptyl, cyclooctyl, ethanolylphenyl, phenyl, phenethyl, naphthyl, 3-indoleethyl, α-acyl C1-C20 alkyl, β-acyl C2-C20 alkyl, γ-acyl C3-C20 alkyl, polypeptide chain C1-C20 alkyl.

10. The method as claimed in claim 8, wherein, in step A), the molar ratio of the α-carbonyl alkenyl ester having the general formula (I) to the compound having the general formula (IV) is 1:1-2; and/or step A) comprises: adding the α-carbonyl alkenyl ester having the general formula (I) and the solvent together in a molar proportion to a reactor, and then adding the compound having the general formula (IV), reacting at −40~100° C. with stirring for 0.05-24 h, using TLC to monitor the completion of the reaction, and obtaining the amide having the general formula (V) by column chromatography after the completion of the reaction.

11. A method for preparing an amide having the general formula (V), comprising:

A) reacting the allenone compound having the general formula (II) with the carboxylic acid having the general formula (III) in a first solvent, optionally separating the reaction product, and then obtaining the α-carbonylalkenyl ester; and B) reacting the α-carbonylalkenyl ester prepared in step A) with a compound having general formula (IV) in a second solvent, optionally separating the reaction product, to obtain an amide having the general formula (V):

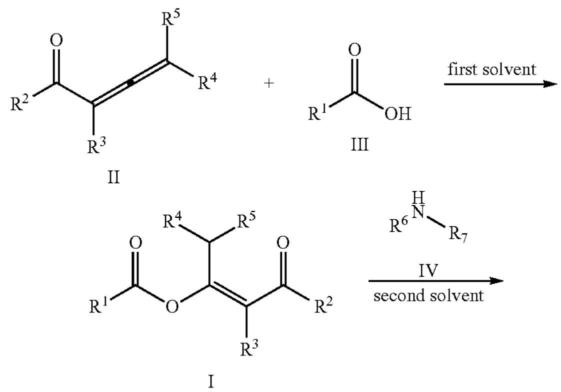

II III I

-continued

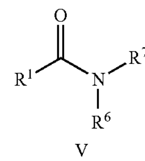
V wherein $R^1$ is selected from one of protected α-amino C1-C20 hydrocarbyl, protected β-amino C2-C20 hydrocarbyl, protected γ-amino C3-C20 hydrocarbyl, and protected polypeptide chain C1-C20 hydrocarbyl;

$R^2$ is selected from one of C1-C24 hydrocarbyl, C1-C24 hydrocarbyl substituted by a substituent(s), aryl, aryl substituted by a substituent(s), heteroaryl and heteroaryl substituted by a substituent(s);

$R^3$, $R^4$, $R^5$ are the same or different, and are each independently selected from one of H, C1-C18 hydrocarbyl, C1-C18 hydrocarbyl substituted by a substituent(s), C1-C16 acyl, cyano, halogen or C1-C16 hydrocarbyloxy-carbonyl; and $R^6$ and $R^7$ are each independently selected from one of H, amino, C1-C24 hydrocarbyl, C1-C24 hydrocarbyl substituted by a substituent(s), or amino oligomers or amino polymers with primary and/or secondary amines; or, $R^6$ and $R^7$ together with the N atom to which they are attached form a C3-C24 cyclic ring;

wherein the first solvent is the same or different from the second solvent.

12. The method as claimed in claim 11, wherein, $R^2$ is selected from one of methyl, ethyl, propyl, isopropyl, butyl, tert-butyl, cyclopentyl, cyclohexyl, phenyl, 4-fluorophenyl, 4-chlorophenyl, 4-bromophenyl, 4-methylphenyl, 4-methoxyphenyl, 2-methylphenyl, 2-methoxyphenyl, 3,5-dimethoxyphenyl, 3-nitrophenyl, 4-nitrophenyl, 2,4-dinitrophenyl, 3,5-dinitrophenyl, pentafluorophenyl, 4-trifluoromethylphenyl, 3,5-dichlorophenyl, 1-naphthyl, 2-naphthyl, furanyl and thienyl; and/or $R^3$, $R^4$, $R^5$ are the same or different from each other, and are each independently selected from one of H, methyl, formyl, acetyl, propionyl, butyryl, cyano, methoxycarbonyl, ethoxycarbonyl, tert-butoxycarbonyl and benzyloxycarbonyl; and/or $R^6$ and $R^7$ are each independently selected from one of H, methyl, ethyl, propyl, isopropyl, butyl, tert-butyl, cyclopentyl, cyclohexyl, cycloheptyl, cyclooctyl, ethanolylphenyl, phenyl, phenethyl, naphthyl, 3-indoleethyl, α-acyl C1-C20 alkyl, β-acyl C2-C20 alkyl, γ-acyl C3-C20 alkyl, polypeptide chain C1-C20 alkyl.

13. The solid-phase synthesis method of polypeptide chain using the α-carbonyl alkenyl ester having the general formula (I) described in claim 1, comprising:

1) Coupling a resin solid phase carrier with the terminal amino acid of the target polypeptide chain sequence or the α-carbonyl alkenyl ester corresponding to the terminal amino acid in a solvent in the presence of a base or a catalyst to obtain PG-AA-resin;

2) According to the sequence of the target polypeptide chain to be synthesized, sequentially adding the α-carbonyl alkenyl ester corresponding to the sequence amino acids and the catalyst or base, and coupling in a solvent to obtain the PG-AA-AA-resin;

3) Deprotecting and cleaving the PG-AA-AA-resin, and removing the side chain protecting group and the resin to obtain crude peptide;

4) purifying and freeze-drying the crude peptide to obtain the target polypeptide chain.

14. The method as claimed in claim 13, wherein, the resin solid phase carrier in step 1) is selected from one of Marrifield resin, Wang resin, 2-CTC resin, and MBHA resin; and/or the α-carbonyl alkenyl ester is selected from one or more of those having the general formula (I) and wherein $R^1$ is a protected α-aminoalkyl, a protected β-aminoalkyl, a protected γ-aminoalkyl, or a protected polypeptide chain alkyl; and/or the catalyst is selected from one of HOAt (1-hydroxy-7-azobenzotriazole), HOBt (1-hydroxybenzotriazole), HOOBt (3-hydroxy-1,2,3-benzotriazin-4 (3H)-one), HOSu (N-hydroxysuccinimide), COMU ((1-Cyano-2-ethoxy-2-oxoethylidenaminooxy)dimethylamino-morpholino-carbenium hexafluorophosphate) and HOPHT (N-hydroxyphthalimide); and/or the base is selected from one or more of 4-dimethylaminopyridine, pyridine, N-methylimidazole, N,N-diisopropylethylamine (DIEA).

15. The method as claimed in claim 13, wherein, in step 1), the amount of the catalyst used is 0.3-10 times the molar amount of the resin used as the solid support; and/or the amount of the allenone used is 1-10 times the molar amount of the PG-AA-resin; and/or in step 201), the amount of the deprotection reagent added is 1-100 times the molar amount of the PG-AA-resin; and/or the deprotection reagent is a solution of piperidine in N,N-dimethylformamide (DMF) or a solution of trifluoroacetic acid in dichloromethane (DCM); and/or in step 202), the amount of the α-carbonyl alkenyl ester is 1-10 times the molar amount of the PG-AA-resin; and/or the amount of the catalyst used is 0.3-10 times the molar amount of the PG-AA-resin; and/or the solvent is an aprotic organic solvent; the aprotic organic solvent is selected from one or two of N,N-dimethylformamide (DMF) and dimethylsulfoxide (DMSO); the mass ratio of the amount of the solvent to the amount of the PG-AA-resin is 10-300:1; and/or in step 4), the purification is carried out by reversed high performance liquid chromatography, the chromatography column is a C18 reversed silica gel column, and the mobile phase is water and acetonitrile.

16. The compound as claimed in claim 3, wherein, $R^2$ is selected from one of phenyl, 4-fluorophenyl, 4-chlorophenyl, 4-bromophenyl, 4-methylphenyl, 4-methoxyphenyl, 2-methylphenyl, 2-methoxyphenyl, 3,5-dimethoxyphenyl, 3-nitrophenyl, 4-nitrophenyl, 2,4-dinitrophenyl, 3,5-dinitrophenyl, pentafluorophenyl, 4-trifluoromethylphenyl, 3,5-dichlorophenyl, 1-naphthyl, 2-naphthyl, furanyl, thienyl, and pyridyl; and/or $R^3$, $R^4$, $R^5$ are each independently selected from one of H, methyl, formyl, acetyl, propionyl, butyryl, cyano, methoxycarbonyl, ethoxycarbonyl, tert-butoxycarbonyl and benzyloxycarbonyl.

17. The method as claimed in claim 5, wherein $R^2$ is selected from one of methyl, ethyl, propyl, isopropyl, butyl, tert-butyl, cyclopentyl, cyclohexyl, phenyl, 4-fluorophenyl, 4-chlorophenyl, 4-bromophenyl, 4-methylphenyl, 4-methoxyphenyl, 2-methylphenyl, 2-methoxyphenyl, 3,5-dimethoxyphenyl, 3-nitrophenyl, 4-nitrophenyl, 2,4-dinitrophenyl, 3,5-dinitrophenyl, pentafluorophenyl, 4-trifluoromethylphenyl, 3,5-dichlorophenyl, 1-naphthyl, 2-naphthyl, furanyl and thienyl; and/or $R^3$, $R^4$, $R^5$ are the same or different from each other, and are each independently selected from one of H, methyl, formyl, acetyl, propionyl, butyryl, cyano, methoxycarbonyl, ethoxycarbonyl, tert-butoxycarbonyl and benzyloxycarbonyl.

18. The method as claimed in claim 11, wherein, step 2) also includes:

201) using a deprotection reagent to remove the terminal protecting group on the PG-AA-resin to obtain H-AA-resin;

202) in the presence of a catalyst, adding α-carbonyl alkenyl ester corresponding to PG-AA-OH, and coupling in a solvent to obtain PG-AA-AA-resin;

203) according to the sequence of the target peptide chain, sequentially repeating step 201) and step 202) to carry out coupling and deprotecting process to extend the peptide chain.

* * * * *

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Crude peptide

<400> SEQUENCE: 1

Tyr Gly Gly Phe Leu
1               5


<210> SEQ ID NO 2
<211> LENGTH: 9
<212> TYPE: PRT
<213> ORGANISM: Artificial Sequence
<220> FEATURE:
<223> OTHER INFORMATION: Crude peptide

<400> SEQUENCE: 2

Cys Tyr Ile Gln Asn Cys Pro Leu Gly
1               5
```